(12) United States Patent
Stutzman-Engwall et al.

(10) Patent No.: US 8,008,078 B2
(45) Date of Patent: *Aug. 30, 2011

(54) STREPTOMYCES AVERMITILIS GENE DIRECTING THE RATIO OF B2:B1 AVERMECTINS

(75) Inventors: Kim J. Stutzman-Engwall, East Lyme, CT (US); Anke Krebber, Palo Alto, CA (US); Claes Gustafsson, Belmont, CA (US); Jeremy S. Minshull, Los Altos, CA (US); Sun Ai Raillard, Mountain View, CA (US); Seran Kim, Waukegan, IL (US); Yan Chen, Santa Clara, CA (US)

(73) Assignees: Pfizer Inc., New York, NY (US); Pfizer Products Inc., Groton, CT (US)

( * ) Notice: Subject to any disclaimer, the term of this patent is extended or adjusted under 35 U.S.C. 154(b) by 606 days.

This patent is subject to a terminal disclaimer.

(21) Appl. No.: 12/107,949

(22) Filed: Apr. 23, 2008

(65) Prior Publication Data

US 2009/0017508 A1    Jan. 15, 2009

Related U.S. Application Data

(62) Division of application No. 10/361,376, filed on Feb. 10, 2003, now Pat. No. 7,388,085.

(60) Provisional application No. 60/356,222, filed on Feb. 12, 2002.

(51) Int. Cl.
*C07H 21/04* (2006.01)
*C12P 19/60* (2006.01)
*C12N 15/74* (2006.01)

(52) U.S. Cl. ........ 435/471; 435/252.3; 435/76; 536/23.2

(58) Field of Classification Search ................. 536/23.2; 435/76, 252.3, 471
See application file for complete search history.

(56) References Cited

U.S. PATENT DOCUMENTS

| 4,310,519 A | 1/1982 | Albers-Schonberg et al. ............. 424/181 |
| 4,429,042 A | 1/1984 | Albers-Schonberg et al. ............. 435/119 |
| 5,252,474 A | 10/1993 | Gewain et al. ........... 435/172.3 |
| 5,605,793 A | 2/1997 | Stemmer ................ 435/6 |
| 5,811,238 A | 9/1998 | Stemmer et al. ............... 435/6 |
| 5,830,721 A | 11/1998 | Stemmer et al. ........... 435/172.1 |
| 5,837,458 A | 11/1998 | Minshull et al. ............... 435/6 |
| 6,197,591 B1 | 3/2001 | Stutzman-Engwall et al. ........................ 435/486 |
| 6,248,579 B1 | 6/2001 | Stutzman-Engwall et al. ....................... 435/253.5 |
| 6,632,673 B1 | 10/2003 | Stutzman-Engwall et al. ............................ 435/471 |
| 7,388,085 B2 | 6/2008 | Stutzmann-Engwall |

FOREIGN PATENT DOCUMENTS

| EP | 0276103 | 1/1988 |
| WO | 95/09863 | 4/1995 |
| WO | WO 9720078 | 6/1997 |
| WO | WO 9941389 | 8/1999 |
| WO | 01/12822 | 2/2001 |
| WO | WO 0112821 | 2/2001 |
| WO | 03/068955 | 8/2003 |

OTHER PUBLICATIONS

PCT International Search Report, PCT/IB03/00348.
Extended European Search Report, EP 09 15 0098.
Stemmer, Proc. Natl. Acad. Sci, 91, pp. 10747-10751, 1994.
Ikeda et al., Chem Rev, 97, pp. 2591-2609, 1997.
Hutchinson, Applied Biochemistry and Biotechnology, 16, pp. 169-190, 1987.
Banks et al., Royal Society of Chemistry, 147, pp. 16-26, 1994.
Stemmer, Nature, 370, pp. 389-391, 1994.
Hopp et al., Proc. Natl Acad Sci, 78(6), pp. 3824-3828, 1981.
Benton et al., Science, 19, pp. 180-182, 1977.
Stutzmann-Engwall et al., Journal of Bacteriology, 174(1), pp. 144-154, 1992.
Anzai et al., The Journal of Antibiotics, XLI(2), pp. 226-233, 1988.
Dutton et al., The Journal of Antibiotics, 44(3), pp. 357-365, 1991.
Vara et al., Journal of Bacteriology, 171(11), pp. 5872-5881, 1989.
Ikeda et al., The Journal of Antibiotics, 48(6), pp. 532-534, 1995.
Grunstein et al., Proc. Nat. Acad Sci, 72(10), pp. 3961-3965, 1975.
Engstroam, Biochem Exp Biol, 11, pp. 7-13, 1974.
Hopwood et al., Annu Rev Genet, 24, pp. 37-66, 1990.
Kieser et al., Methods in Enzymology, 204, pp. 430-458, 1991.

*Primary Examiner* — Chih-Min Kam
(74) *Attorney, Agent, or Firm* — Paul M. Misiak

(57) ABSTRACT

The present invention relates to polynucleotide molecules comprising nucleotide sequences encoding an aveC gene product, which polynucleotide molecules can be used to alter the ratio or amount of class 2:1 avermectins produced in fermentation cultures of *S. avermitilis*. The present invention further relates to vectors, host cells, and mutant strains of *S. avermitilis* in which the aveC gene has been inactivated, or mutated so as to change the ratio or amount of class 2:1 avermectins produced.

5 Claims, 18 Drawing Sheets

FIG. 1

```
1    TCACGAAACCGGACACCACCACACGAAGGTGAGACAGCGTGAAACCCATCCGAGCCTGCCCAACGAACGTGTAGTAGAGACCCGACCGTC
     ----+----|----+----|----+----|----+----|----+----|----+----|----+----|----+----|----+----  100
     CGATGCCACGCTCACCCGAGGCGCGGCCTGCCTCACTCCGTGATTTCCGGCTGCCGGTGGTGTGGGGCGGGGTGTCGGCCTG

101  CTGTTTCTGGCCCTGCAGGCGTACGTGTTCAGCCGCTGGGCGGCCGACGGTGGCTACCGGCTGATCGAGACAGGGGGCCAGGGTCAGGGCGGCAGCAAGG
     ----+----|----+----|----+----|----+----|----+----|----+----|----+----|----+----|----+----  200
         1-V V V W A G V G L
201  L F L A L Q A Y V F S R W A A D G G Y R L I E T A G Q G Q G G S K D
     ATACGGGGACTACCGATGTGGTCTATCCCGTGATTTCCGTCGTCTGCATCACCGCGGCGGCGGCGGGCGTGGGCTCTTCCGGAGGTGCCGTCGAACGACGGCT  300

301  T G T T D V V Y P V I S V V C I T A A A W L F R R C V E R R L
     GCTGTGTTGCGACGGCCCCTCTCTTCCTCGGCGGCTGCGCTGCCGAGCGTGGCAGAGCCGCCGTCATGAACTGGTTCCATTCCGTTCTCGTCTCCAACGCGAGTGTG  400

401  L F D A L L F L G L L F A S W Q S P L M N W F H S V L V S N A S V
     TGGGGCGGCGCGGTGGGGTTCCTGGGGTCCGCTATGTGCCCGGGCTGGCAGGGGCGGCGGCGGAGGCGGAAATGCCGCTCGGCCTCCGTCTGCA  500

501  W G A V G S W G P Y V P G W Q G A G P G A E E M P L A S A S V C M
     TGTCGGCTCTGATCGTCACCGTGCTGTGCAAGGCACTGGGGTGGATCAAGGCCCGGGCCGCTGCCGGAGGTGACCTTGTGGAGTGGC  600

601  S A L I V T V L C S K A L G W I K A R R P A W R T W R L V L A V F
     CTTCATCGGCATCGTCCTGTCCGAGCCGCTGCCGTCCGGCCTCGGAGCTGAGTGCATGCCGGATCAGCGTATGGCCCGAGGTGACCTGCCCAGAGCTG  700

701  F I G I V L G L S E P L P S A S G I S V W A R A L P E V T L W S G
     GAGTGGTACCAGTTCCCCGTGTATCAGGCGGTCGGTTCGGAGCCTGCTGCTGCATGCTGGGCTCGCTGCGCTTCTTCCGGACGAACGGCGATGAGTCGT  800

801  E W Y Q F P V Y Q A V G S G L V C C M L G S L R F F R D E R D E S W
     GGGTGGAACGGGAGCCTGGGCGTTGCCGCAACGGGCAGCAGGGAACTGGGCGCGTTCCTCCGCGGTCGTGGGGTGAATGCCGTGATGTTCCTCTACAC  900

901  V E R G A W R L P Q R A A N W A R F L A V V G G V N A V M F L Y T
     CTGTTTCCATATCCTCCTGTCCCTGGTCGGTGGGCAGCCGCCCCCGACCAGCGCCCTTCCAAGGCGCCGGCCGCTTACGTAGTTCAGGGCAGGTCG  1000

1001 C F H I L L S L V G G Q P P D Q L P D S F Q A P A A Y
     GAGGAGAACGGAGAAGGGGAGGCCGGAAGTTCGGTGCATCAGGGATGGAGACAGGGGGACATCCCCAGGCGGCGGCCTCCAGAC  1100

1101 GCACCACACTCCTCGGTTCAGCGGATCATG
     ----+----|----+----|----+ 1229
1201
```

| Plasmid | Mutations | [B2] | [B1] | B2/B1 |
|---|---|---|---|---|
| pSE501 | D48E, L136P, G179S, E238D | 52 | 184 | 0.28 |
| | (A132G), T317A, T580C, G708A, A887T, (A1124G) | | | |
| pSE502 | D48E, A89T, L136P, G179S, E238D | 42 | 204 | 0.20 |
| | T317A, G438A, T580C, G708A, A887T | | | |
| pSE503 | D48E, A89T, L136P, K154E, G179S, E238D | 32 | 172 | 0.19 |
| | T317A, G438A, (T497C), T580C, T633C, G708A, (C775T), A887T | | | |
| pSE504 | D25G, D48E, A89T, L136P, S138T, A139T, V141A, I159T, R163Q, G179S | 44 | 205 | 0.21 |
| | A247G, T317A, G438A, (T497C), T580C, T585A, G588A, T595C, T649C, G661A, G708A, (C884T) | | | |
| pSE505 | D48E, A89T, S138T, A139T, K154R, G179S, V196A, P289L | 35 | 178 | 0.20 |
| | T317A, G438A, T585A, G588A, A634G, G708A, T760C, A761C, C1039T | | | |
| pSE506 | D48E, A89T, S138T, A139F, G179S, V196A, E238D | 26 | 135 | 0.19 |
| | T317A, G438A, (T497C), T585A, G588T, G589T, G708A, T760C, A761C, A887C | | | |
| pSE507 | D48E, A61T, A89T, L136P, G179S, V196A, A198G, P289L | 18 | 88 | 0.20 |
| | T317A, G354A, G438A, (T497C), T580C, G708A, T760C, A761C, C766G, C1039T | | | |

FIG. 6A

| Plasmid | Mutations | [B2] | [B1] | B2/B1 |
|---|---|---|---|---|
| pSE508 | D48E, A89T, S90G, L136P, R163Q, G179S, E238D | 22 | 91 | 0.24 |
| | T317A, G438A, A441G, T580C, G661A, G708A, A887T, (A938G) | | | |
| pSE509 | D48E, A61T, S138T, A139F, G179S, G196A, E238D, P289L | 22 | 114 | 0.19 |
| | (G136A), T317A, G354A, (T497C), T585A, G588T, C589T, G708A, T760C, A761C, A887C, C1039T | | | |
| pSE510 | D48E, A61T, L136P, G179S, E238D | 64 | 211 | 0.30 |
| | T317A, G354A, (T497C), T580C, G708A, A887C | | | |
| pSE511 | D48E, A61T, A89T, G111V, S138T, A139T, G179S, E238D, P289L | 20 | 91 | 0.21 |
| | T317A, G354A, (T416C), G438A, G505T, T585A, G588A, G708A, (G775T), A887C, C1039T | | | |
| pSE512 | D48E, A61T, L136P, G179S | 55 | 88 | 0.29 |
| | T317A, G354A, (T497C), T580C, G708A | | | |
| pSE514 | D48E, A89T, L136P, G179S | 36 | 175 | 0.20 |
| | (T33A), T317A, G438A, (T497C), T580C, G708A | | | |
| PSE515 | D48E, A89T, V120A, L136P, G179S | 36 | 189 | 0.19 |
| | T317A, G438A, T532C, T580C, G708A, (T1031C) | | | |

FIG. 6B

| Plasmid | Mutations | [B2] | [B1] | B2/B1 |
|---|---|---|---|---|
| pSE517 | D48E, A61T, A89T, S138T, A139F, G179S, V196A, A198G, E238D | 20 | 99 | 0.20 |
| | T317A, G354A, G438A, (T497C), T585A, G588T, C589T, G708A, T760C, A761C, C766G, A887C | | | |
| pSE518 | D48E, A61T, A89T, G111V, S138T, A139F, G179S, V196A, E238D | 11 | 57 | 0.18 |
| | T317A, G354A, G438A, G505T, T585A, G588T, C589T, G708A, T760C, A761C, A887C | | | |
| pSE519 | D48E, A89T, S138T, A139T, G179S | 40 | 153 | 0.26 |
| | T317A, G438A, T585A, G588A, G708A | | | |
| pSE520 | D48E, A89T, S138T, A139T, G179S | 45 | 177 | 0.25 |
| | T317A, G438A, (T497C), T585C, G588A, G708A | | | |
| pSE523 | D48E, L136P, R163Q, G179S, S231L | 37 | 168 | 0.22 |
| | T317A, T580C, G661A, G708A, (T797C), C865T | | | |
| pSE524 | D48E, A89T, L136P, G179S, E238D | 25 | 137 | 0.18 |
| | T317A, G438A, (T497C), T580C, G708A, A887T | | | |
| pSE525 | D48E, A89T, L136P, G179S | 22 | 129 | 0.17 |
| | T317A, G438A, (T497C), T580C, G708A | | | |

FIG. 6C

| Plasmid | Mutations | [B2] | [B1] | B2/B1 |
|---|---|---|---|---|
| pSE526 | D48E, A61T, L136P, G179S, A198G, P202S, E238D, P289L, | 35 | 135 | 0.26 |
| | T317A, G354A, (T497C), T580C, G708A, C766G, C777T, A887C, C1039T | | | |
| pSE527 | D48E, L136P, S138T, A139F, G179S, V196A, E238D | 31 | 119 | 0.25 |
| | T317A, (T497C), T580C, T585A, G588T, C589T, G708A, T760C, A761C, A887C | | | |
| pSE528 | D48E, A61T, L136P, S138T, A139F, G179S, E238D, P289L | 50 | 160 | 0.30 |
| | T317A, G354A, (T497C), T580C, T585A, G588T, C589T, G708A, A887C, C1039T | | | |
| pSE529 | D48E, A61T, A89T, S138T, A139T, G179S, V196A, E238D, P289L | 26 | 150 | 0.17 |
| | T317A, G354A, G438A, (T497C), T585A, G588A, G708A, T760C, A761C, A887C, C1039T | | | |
| pSE530 | D48E, L136P, G179S, A198G, E238D, P289L | 37 | 136 | 0.27 |
| | (C97T), T317A, T580C, G708A, C766G, A887C, C1039T | | | |
| pSE531 | D48E, A61T, S138T, A139F, G179S, A198G, P289L | 27 | 101 | 0.27 |
| | T317A, G354A, (T497C), T585A, G588T, C589T, G708A, C766G, C1039T | | | |

FIG. 6D

| Plasmid | Mutations | [B2] | [B1] | B2/B1 |
|---|---|---|---|---|
| pSE532 | D48E, A61T, A89T, L136P, S138T, A139F, G179S, A198G, E238D | 19 | 91 | 0.20 |
| | T317A, G354A, G438A, (T497C), T580C, T585A, G588T, C589T, G708A, C766G, A887C | | | |
| pSE534 | D48E, L84P, G111V, S138T, A139T, G179S, A198G, P289L | 37 | 139 | 0.26 |
| | T317A, T424C, G505T, T585A, G588A, G708A, C766G, C1039T | | | |
| pSE535 | Y28C, D48E, A61T, A89T, S138T, A139T, G179S, E238D | 34 | 132 | 0.26 |
| | A256G, T317A, G354A, G438A, T585A, G588A, G708A, A887C | | | |
| pSE536 | D48E, A89T, S138T, A139F, G179S, A198G, V220A | 19 | 106 | 0.17 |
| | (G137T), T317A, G438A, (T497C), T585A, G588T, C589T, G708A, C766G, T832C | | | |
| pSE537 | D48E, A61T, A89T, S138T, A139T, G179S, V196A, E238D, R239H, P289L | 34 | 171 | 0.19 |
| | T317A, G354A, G438A, (T497C), T585A, G588A, G708A, T760C, A761C, A887C, G889A, C1039T | | | |
| pSE538 | D48E, A61T, A89T, S138T, A139T, G179S, A198G, P289L | 13 | 39 | 0.33 |
| | T317A, G354A, G438A, T585A, G588A, G708A, C766G, C1039T | | | |
| pSE539 | D48E, A61T, A89T, F99S, S138T, A139T, G179S, E238D | 43 | 179 | 0.24 |
| | T317A, G354A, G438A, G469C, (T497C), T585A, G588A, G708A, A887C, (C1094T) | | | |

FIG. 6E

| Plasmid | Mutations | [B2] | [B1] | B2/B1 |
|---|---|---|---|---|
| pSE540 | G35S, D48E, A89T, S138T, A139T, G179S, P289L | 42 | 180 | 0.23 |
| | G276A, T317A, G438A, (T497C), T585A, G588A, G708A,.C1039T | | | |
| pSE541 | D48E, A61T, A89T, L136P, G179S, P289L | 36 | 174 | 0.20 |
| | (C266T), T317A, G354A, G438A, (T497C), T580C, G708A, C1039T | | | |
| pSE542 | D48E, A61T, A107T, S108G, L136P, G179S, S192A, E238D, P289L | 50 | 175 | 0.29 |
| | T317A, G354A, G492A, A495G, (T497C), T580C, G708A, T747G, A887C, C1039T | | | |
| pSE543 | D48E, A61T, A89T, G111V, S138T, A139F, G179S, E238D, P289L | 17 | 67 | 0.25 |
| | T317A, G354A, G438A, G505T, T585A, G588T, C589T, G708A, A887C, C1039T | | | |
| pSE545 | D48E, L136P, G179S, R250W | 37 | 134 | 0.27 |
| | G317A, T580C, G708A, C921T | | | |
| pSE546 | D48E, L136P, G179S, E238D | 48 | 178 | 0.27 |
| | G317A, T580C, G708A, A887T | | | |
| pSE547 | D48E, A61T, A89T, S138T, A139T, G179S, V196A, E238D | 32 | 142 | 0.23 |
| | T317A, G354A, G438A, T585A, G588A, G708A, T760C, A761C, A887C | | | |

FIG. 6F

| Plasmid | Mutations | [B2] | [B1] | B2/B1 |
|---|---|---|---|---|
| pSE548 | D48E, A89T, S138T, A139T, R163Q, G179S | 41 | 157 | 0.26 |
| | (T114C), (T130C), T317A, G438A, T585A, G588A, G661A, G708A | | | |
| pSE549 | D48E, A89T, S138T, A139T, G179S, V196A, E238D, P289L | 24 | 141 | 0.17 |
| | G317A, G438A, (T497C), T585A, G588A, G708A, T760C, A761C, A887C, C1039T | | | |
| pSE550 | D48E, A89T, G111V, S138T, A139T, G179S, A198G, E238D | 19 | 76 | 0.25 |
| | T317A, G438A, G505T, T585A, G588A, G708A, C766G, A887C | | | |
| pSE551 | D48E, A61T, A89T, S138T, A139F, G179S, V196A, E238D | 24 | 141 | 0.17 |
| | T317A, G354A, G438A, (T497C), T585A, G588T, C589T, G708A, T760C, A761C, A887C | | | |
| pSE552 | D48E, L136P, G179S, A198G, P289L | 40 | 154 | 0.26 |
| | T317A, (T497C), T580C, G708A, C766G, C1039T | | | |
| pSE553 | D48E, A89T, S138T, A139T, G179S, V196A, E238D, P289L | 23 | 123 | 0.18 |
| | T317A, G438A, (T497C), T585A, G588A, G708A, T760C, A761C, A887C, C1039T | | | |
| pSE554 | D48E, A61T, A89T, S138T, A139T, G179S, V196A, E238D, P289L | 30 | 162 | 0.18 |
| | T317A, G354A, G438A, (T497C), T585A, G588A, G708A, T760C, A761C, A887C, C1039T | | | |

FIG. 6G

| Plasmid | Mutations | [B2] | [B1] | B2/B1 |
|---|---|---|---|---|
| PSE556 | D48E, S138T, A139T, G179S, E238D | 66 | 177 | 0.37 |
| | (T169C), T317A, T585A, G588A, G708A, A887T | | | |
| pSE557 | D48E, F78L, A89T, L136P, G179S | 57 | 219 | 0.26 |
| | A317A, T405C, G438A, T580C, G708A | | | |
| pSE558 | S41G, D48E, A89T, L136P, G179S | 51 | 215 | 0.24 |
| | (G87A), A294G, T317A, G438A, T580C, G708A | | | |
| pSE559 | G40S, D48E, L136P, G179S, E238D | 81 | 247 | 0.33 |
| | G291A, T317A, T580C, G708A, A887T | | | |
| PSE561 | Y28C, Q38R, D48E, L136P, G179S, E238D | 31 | 83 | 0.37 |
| | A256G, A286G, T317A, (T497C), T580C, G708A, A887T | | | |
| pSE563 | D48E, A89T, L136P, R163Q, G179S, P252S | 43 | 177 | 0.24 |
| | T317A, G438A, T580C, G661A, G708A, C927T | | | |
| pSE564 | D48E, A89T, S138T, A139T, G179S, E238D, F278L | 61 | 216 | 0.28 |
| | T317A, G438A, (T497C), T585A, G588A, G708A, A887T, T1005C | | | |
| pSE565 | D48E, A89T, S138T, A139T, G179S, E238D, F278L | 59 | 210 | 0.28 |
| | T317A, G438A, (T497C), T585A, G588A, G708A, A887T, T1005C | | | |

FIG. 6H

| Plasmid | Mutations | [B2] | [B1] | B2/B1 |
|---|---|---|---|---|
| pSE566 | D48E, A89T, L136P, G179S, F234S | 37 | 154 | 0.24 |
| | T317A, (C341T), G438A, (T497C), T580C, (C695T), G708A, T874C | | | |
| pSE567 | D48E, L136P, R163Q, G179S, | 60 | 192 | 0.31 |
| | T317A, T580C, G661A, G708A | | | |
| pSE568 | D48E, A89T, L136P, R163Q, G179S | 48 | 173 | 0.28 |
| | (T85C), T317A, G438A, (T497C), T580C, G661A, G708A, (C800T) | | | |
| PSE569 | D48E, S138T, A139T, G179S, E238D | 59 | 153 | 0.38 |
| | (T104C), T317A, (T497C), T585A, G588A, G708A, A887T | | | |
| pSE570 | D48E, L136P, R163Q, G179S, E238D | 73 | 221 | 0.33 |
| | T317A, T580C, G661A, G708A, A887T | | | |
| pSE571 | D48E, L136P, R163Q, G179S, A200G, E238D | 75 | 236 | 0.32 |
| | (T67C), T317A, T580C, G661A, G708A, C772G, A887T | | | |
| pSE572 | D48E, L136P, R163Q, G179S, E238D | 74 | 229 | 0.32 |
| | T317A, (T497C), T580C, G661A, G708A, A887T | | | |
| pSE573 | D48E, A89T, L136P, R163Q, G179S, E238D | 39 | 173 | 0.23 |
| | T317A, G438A, T580C, G661A, G708A, A887T | | | |

FIG. 61

| Plasmid | Mutations | [B2] | [B1] | B2/B1 |
|---|---|---|---|---|
| pSE574 | Q36R, D48E, A89T, L136P, G179S, E238D | 53 | 231 | 0.23 |
| | A280G, T317A, (G359A), G438A, T580C, G708A, (T836C), A887T | | | |
| pSE575 | D48E, A89T, L136P, R163Q, G179S | 49 | 217 | 0.23 |
| | T317A, G438A, T580C, G661A, (C704T), G708A, (G965A) | | | |
| pSE576 | D48E, A89T, L136P, R163Q, G179S | 44 | 197 | 0.22 |
| | T317A, G438A, T580C, G661A, G708A | | | |
| pSE577 | D48E, A89T, S138T, G179S | 36 | 140 | 0.25 |
| | T317A, G438A, (T497C), T585A, G708A | | | |
| pSE578 | D48E, A89T, L136P, R163Q, G179S, E238D | 45 | 193 | 0.23 |
| | T317A, G438A, (T497C), T580C, G661A, G708A, A887T | | | |

FIG. 6J

| Plasmid | Mutations | [B2] | [B1] | B2/B1 |
|---|---|---|---|---|
| pSE582 ca | V3L, L136M | 186 | 178 | 1.04 |
| pSE583 cb | G26A, D48Y, R75W, S93N | 94 | 88 | 1.07 |
| pSE584 cc | R71L | 314 | 293 | 1.07 |
| pSE585 cd | T47I, W110L, A139T | 168 | 189 | 0.89 |
| pSE586 ce | V104I, S138T, V220I, F234I | 150 | 138 | 1.10 |
| pSE587 cf | G45R, A64V, R69K | 182 | 192 | 0.95 |
| pSE588 cg | S90N | 251 | 243 | 1.03 |
| pSE589 ch | G26D, W110L, R233H | 97 | 107 | 0.91 |
| pSE590 ci | Q36R, V104I, P128S, C152W, T276A | 194 | 171 | 1.13 |
| pSE591 cj | S90N | 164 | 147 | 1.12 |
| pSE592 ck | C142Y, A302T | 152 | 133 | 1.14 |
| pSE593 cl | V2M, V56D | 117 | 121 | 0.97 |
| pSE594 cm | S41G, L87V, A139T, L206M, G209R, I280V | 122 | 212 | 0.58 |
| pSE595 cn | A62V, A139D | 150 | 122 | 1.23 |
| pSE596 co | F176C | 203 | 204 | 1.0 |
| pSE597 cp | T149S | 120 | 135 | 0.89 |
| pSE598 cq | A64T, C142Y | 105 | 90 | 1.17 |
| pSE599 cr | A130V, C142Y, L224M, E238V, L293M | 79 | 71 | 1.11 |
| pSE600 cs | A16T, K154M, L206F | 103 | 97 | 1.06 |

FIG. 6K

| Plasmid | Mutations | [B2] | [B1] | B2/B1 |
|---|---|---|---|---|
| PSE601 da | S41G, D48E, A61T, R71L, A89T, L136M, S138T, A139T, T149S, G179S, V196A, E238D, F278L, P289L | 17 | 137 | 0.12 |
| PSE602 db | S41G, D48E, A61T, R71L, A89T, L136M, S138T, A139T, T149S, F176C, G179S, V196A, E238D, P289L | 17 | 87 | 0.19 |
| PSE603 dc | D48E, R71L, A89T, L136P, T149S, F176C, G179S, E238D, I280V | 19 | 146 | 0.13 |
| PSE604 dd | D48E, A61T, R71L, W110L, T149S, G179S, V196A, L206M, E238D, V271A, I280V | 26 | 180 | 0.14 |
| PSE605 de | D48E, A61T, R71L, A89T, L136M, S138T, A139T, T149S, G179S, V196A, E238D, H279Q, P289L | 22 | 158 | 0.14 |
| PSE606 df | D48E, A61T, R71L, A89T, L136M, S138T, A139T, T149S, G179S, V196A, E238D, G287E, P289Q | 16 | 94 | 0.17 |
| PSE607 dg | D48E, A61T, R71L, A89T, L136M, S138T, A139T, T149S, G179S, V196A, E238D, P289L | 21 | 243 | 0.13 |
| PSE608 dh | D48E, A61T, R71L, A89T, A139T, T149S, F176C, G179S, V196A, E238D, V285G, P289L | 18 | 146 | 0.12 |
| PSE609 di | Q38R, D48E, A61T, R71L, L87V, A89T, L136M, S138T, A139T, T149S, G179S, V196A, E238D, P289L | 20 | 150 | 0.13 |
| PSE610 dj | D48E, A61T, L87V, A89T, W110L, S138T, A139T, T149S, G179S, V196A, E238D, P289L | 14 | 110 | 0.13 |
| PSE611 dk | D48E, A61T, R71L, A89T, L136M, S138T, A139T, T149S, G179S, V196A, E238D, P289L | 25 | 184 | 0.14 |
| PSE612 dl | D48E, A89T, L136P, K154E, G179S, S231L, E238D | 16 | 132 | 0.12 |

FIG. 6L

| Plasmid | Mutations | [B2] | [B1] | B2/B1 |
|---|---|---|---|---|
| pSE617 ea | D48E, A61T, R71L, A89T, L136P, T149S, F176C, G179S, V196A, E238D, I280V | 4 | 86 | 0.05 |
| pSE620 eb | D48E, R71L, A89T, L136P, T149S, F176C, G179S, E238D, I280V | 17 | 179 | 0.08 |
| pSE621 ec | Q36P, D48E, A61T, R71L, A89T, L136P, T149S, F176C, G179S, V196A, E238D, I280V | 12 | 204 | 0.06 |
| pSE622 ed | D48E, A61T, R71L, A89T, A139T, T149S, F176C, G179S, V196A, E238D, I280V | 16 | 226 | 0.07 |
| pSE639 ee | V2M, D48E, A61T, R71L, A89T, L136P, T149S, F176C, G179S, V196A, E238D, I280V | 15 | 225 | 0.07 |
| pSE643 ef | D48E, A61T, R71L, A89T, L136P, T149S, F176C, G179S, V196A, E238D, I280V, A302T | 19 | 247 | 0.08 |
| pSE646 eg | D48E, R71L, A89T, L136P, T149S, F176C, G179S, E238D, P289L | 7 | 100 | 0.06 |
| pSE655 eh | D48E, R71L, A89T, L136P, T149S, F176C, G179S, E238D, A302T | 10 | 139 | 0.07 |
| pSE657 ei | D48E, R71L, A89T, L136P, T149S, F176C, G179S, V196A, E238D, I280V | 9 | 157 | 0.06 |
| pSE659 ej | D48E, A61T, R71L, A89T, L136P, T149S, F176C, G179S, V196A, E238D | 7 | 105 | 0.06 |
| pSE670 ek | V2M, D48E, R71L, A89T, L136P, T149S, F176C, G179S, V196A, E238D, I280V | 7 | 104 | 0.07 |
| pSE682 el | D48E, A61T, R71L, A89T, L136P, T149S, R162H, F176C, G179S, V196A, E238D, I280V | 4 | 83 | 0.05 |
| pSE683 em | D48E, R71L, A89T, V120A, L136P, T149S, K154E, G179S, S231L, E238D | 8 | 154 | 0.05 |
| pSE684 en | D48E, R71L, A89T, V120A, L136P, T149S, F176C, G179S, S231L, E238D, I280V | 11 | 155 | 0.07 |
| pSE685 eo | D48E, A61T, R71L, L87V, A89T, S90N, A139T, T149S, F176C, G179S, V196A, E238D, V285G, P289L | 11 | 134 | 0.08 |
| pSE686 ep | D48E, A61T, R71L, L87V, A89T, A139T, T149S, F176C, G179S, V196A, E238D, V285G, P289L | 8 | 100 | 0.08 |
| pSE579 eq | D48E, R71L, A89T, L136P, K154E, G179S, S231L, E238D | 16 | 178 | 0.09 |
| pSE580 er | D48E, R71L, A89T, V120A, L136P, K154E, F176C, G179S, S231L, E238D | 14 | 149 | 0.09 |
| PSE581 es | D48E, R71L, A89T, V120A, L136P, T149S, K154E, F176C, G179S, S231L, E238D | 8 | 146 | 0.06 |

FIG. 6M

SEQUENCE LISTING

<160> NUMBER OF SEQ ID NOS: 16

<210> SEQ ID NO 1
<211> LENGTH: 1229
<212> TYPE: DNA

<213> ORGANISM: Streptomyces avermitilis
<220> FEATURE:
<221> NAME/KEY: CDS
<222> LOCATION: (174)..(1085)

<400> SEQUENCE: 1

```
tcacgaaacc ggacacacca cacacacgaa ggtgagacag cgtgaaccca tccgagccgc      60
tcggcctgcc caacgaacgt gtagtagaca cccgaccgtc cgatgccacg ctctcacccg     120
aggccggcct gaacaggtca ggagcgctgc ccgtgaact gctgtcgttg ccg gtg         176
                                                         Val
                                                         1 gtg gtg tgg gcc ggg gtc ggc ctg ctg ttt ctg gcc ctg cag gcg tac      224
Val Val Trp Ala Gly Val Gly Leu Leu Phe Leu Ala Leu Gln Ala Tyr
         5                  10                  15 gtg ttc agc cgc tgg gcg gcc gac ggt ggc tac cgg ctg atc gag acg      272
Val Phe Ser Arg Trp Ala Ala Asp Gly Gly Tyr Arg Leu Ile Glu Thr
         20                  25                  30 gcg ggc cag ggt cag ggc ggc agc aag gat acg ggg act acc gat gtg      320
Ala Gly Gln Gly Gln Gly Gly Ser Lys Asp Thr Gly Thr Thr Asp Val
 35                  40                  45 gtc tat ccc gtg att tcc gtc gtc tgc atc acc gcc gcg gcg gcg tgg      368
Val Tyr Pro Val Ile Ser Val Val Cys Ile Thr Ala Ala Ala Ala Trp
 50                  55                  60                  65 ctc ttc cgg agg tgc cgt gtc gaa cga cgg ctg ctg ttc gac gcc ctt      416
Leu Phe Arg Arg Cys Arg Val Glu Arg Arg Leu Leu Phe Asp Ala Leu
             70                  75                  80 ctc ttc ctc ggg ctg ctg ttc gcg agc tgg cag agc ccg ctc atg aac      464
Leu Phe Leu Gly Leu Leu Phe Ala Ser Trp Gln Ser Pro Leu Met Asn
         85                  90                  95 tgg ttc cat tcc gtt ctc gtc tcc aac gcg agt gtg tgg ggc gcg gtg      512
Trp Phe His Ser Val Leu Val Ser Asn Ala Ser Val Trp Gly Ala Val
         100                 105                 110 ggt tcc tgg ggt ccg tat gtg ccc ggc tgg cag ggg gcg ggc ccg ggt      560
Gly Ser Trp Gly Pro Tyr Val Pro Gly Trp Gln Gly Ala Gly Pro Gly
 115                 120                 125 gcg gag gcg gaa atg ccg ctg gcg tcg gcc tcc gtc tgc atg tcg gct      608
Ala Glu Ala Glu Met Pro Leu Ala Ser Ala Ser Val Cys Met Ser Ala
130                 135                 140                 145 ctg atc gtc acc gtg ctg tgc agc aag gca ctg ggg tgg atc aag gcc      656
Leu Ile Val Thr Val Leu Cys Ser Lys Ala Leu Gly Trp Ile Lys Ala
                 150                 155                 160 cgc cgg ccg gca tgg cgg acc tgg cgg ctg gtc ctg gcc gtg ttc ttc      704
Arg Arg Pro Ala Trp Arg Thr Trp Arg Leu Val Leu Ala Val Phe Phe
             165                 170                 175 atc ggc atc gtg ctc ggt ctg tcc gag ccg ctg ccg tcc gcc tcc ggg      752
Ile Gly Ile Val Leu Gly Leu Ser Glu Pro Leu Pro Ser Ala Ser Gly
         180                 185                 190 atc agc gta tgg gcc aga gcg ctg ccc gag gtg acc ttg tgg agt ggc      800
Ile Ser Val Trp Ala Arg Ala Leu Pro Glu Val Thr Leu Trp Ser Gly
 195                 200                 205 gag tgg tac cag ttc ccc gtg tat cag gcg gtc ggt tcc ggc ctg gtc      848
Glu Trp Tyr Gln Phe Pro Val Tyr Gln Ala Val Gly Ser Gly Leu Val
210                 215                 220                 225 tgc tgc atg ctg ggc tcg ctg cgc ttc ttc cgc gac gaa cgc gat gag      896
Cys Cys Met Leu Gly Ser Leu Arg Phe Phe Arg Asp Glu Arg Asp Glu
                 230                 235                 240 tcg tgg gtg gaa cgg gga gcc tgg cgg ttg ccg caa cgg gca gcg aac      944
Ser Trp Val Glu Arg Gly Ala Trp Arg Leu Pro Gln Arg Ala Ala Asn
             245                 250                 255 tgg gcg cgt ttc ctc gcc gtg gtc ggt ggg gtg aat gcc gtg atg ttc      992
Trp Ala Arg Phe Leu Ala Val Val Gly Gly Val Asn Ala Val Met Phe
```

-continued

```
                Trp Ala Arg Phe Leu Ala Val Val Gly Gly Val Asn Ala Val Met Phe
                    260                 265                 270 ctc tac acc tgt ttc cat atc ctc ctg tcc ctc gtc ggt gga cag ccg       1040
Leu Tyr Thr Cys Phe His Ile Leu Leu Ser Leu Val Gly Gly Gln Pro
    275                 280                 285 ccc gac caa ctg ccg gac tcc ttc caa gcg ccg gcc gct tac tga            1085
Pro Asp Gln Leu Pro Asp Ser Phe Gln Ala Pro Ala Ala Tyr
290                 295                 300 gttcagggca ggtcgagga  gacggagaag gggaggcgac cggagttccg gtcacctccc     1145
ctttgtgcat gggtggacgg ggatcacgct cccatggcgg cgggctcctc cagacgcacc     1205
acactcctcg gttcagcgat catg                                            1229
```

<210> SEQ ID NO 2
<211> LENGTH: 303
<212> TYPE: PRT
<213> ORGANISM: Streptomyces avermitilis

<400> SEQUENCE: 2

```
Val Val Val Trp Ala Gly Val Gly Leu Leu Phe Leu Ala Leu Gln Ala
  1               5                  10                  15

Tyr Val Phe Ser Arg Trp Ala Ala Asp Gly Gly Tyr Arg Leu Ile Glu
                 20                  25                  30

Thr Ala Gly Gln Gly Gln Gly Gly Ser Lys Asp Thr Gly Thr Thr Asp
             35                  40                  45

Val Val Tyr Pro Val Ile Ser Val Val Cys Ile Thr Ala Ala Ala Ala
         50                  55                  60

Trp Leu Phe Arg Arg Cys Arg Val Glu Arg Arg Leu Leu Phe Asp Ala
 65                  70                  75                  80

Leu Leu Phe Leu Gly Leu Leu Phe Ala Ser Trp Gln Ser Pro Leu Met
                 85                  90                  95

Asn Trp Phe His Ser Val Leu Val Ser Asn Ala Ser Val Trp Gly Ala
                100                 105                 110

Val Gly Ser Trp Gly Pro Tyr Val Pro Gly Trp Gln Gly Ala Gly Pro
            115                 120                 125

Gly Ala Glu Ala Glu Met Pro Leu Ala Ser Ala Ser Val Cys Met Ser
        130                 135                 140

Ala Leu Ile Val Thr Val Leu Cys Ser Lys Ala Leu Gly Trp Ile Lys
145                 150                 155                 160

Ala Arg Arg Pro Ala Trp Arg Thr Trp Arg Leu Val Leu Ala Val Phe
                165                 170                 175

Phe Ile Gly Ile Val Leu Gly Leu Ser Glu Pro Leu Pro Ser Ala Ser
            180                 185                 190

Gly Ile Ser Val Trp Ala Arg Ala Leu Pro Glu Val Thr Leu Trp Ser
        195                 200                 205

Gly Glu Trp Tyr Gln Phe Pro Val Tyr Gln Ala Val Gly Ser Gly Leu
    210                 215                 220

Val Cys Cys Met Leu Gly Ser Leu Arg Phe Phe Arg Asp Glu Arg Asp
225                 230                 235                 240

Glu Ser Trp Val Glu Arg Gly Ala Trp Arg Leu Pro Gln Arg Ala Ala
                245                 250                 255

Asn Trp Ala Arg Phe Leu Ala Val Val Gly Gly Val Asn Ala Val Met
            260                 265                 270

Phe Leu Tyr Thr Cys Phe His Ile Leu Leu Ser Leu Val Gly Gly Gln
        275                 280                 285

Pro Pro Asp Gln Leu Pro Asp Ser Phe Gln Ala Pro Ala Ala Tyr
    290                 295                 300
```

-continued

```
                       290                 295                 300

<210> SEQ ID NO 3
<211> LENGTH: 1150
<212> TYPE: DNA
<213> ORGANISM: Streptomyces hygroscopicus
<220> FEATURE:
<221> NAME/KEY: CDS
<222> LOCATION: (58)..(990)

<400> SEQUENCE: 3
gtcgacgaag accggccgga ggccgtcggc cgggccgata ccgtacgcgg cctgcgg              57 gtg ttc acc ctt ccc gta aca ctg tgg gcg tgt gtc ggc gcg ctg gtg           105
Val Phe Thr Leu Pro Val Thr Leu Trp Ala Cys Val Gly Ala Leu Val
 1               5                  10                  15 ctg gga ctt cag gtg tac gtg ttc gcc gcc tgg ctc gcc gac agc ggc           153
Leu Gly Leu Gln Val Tyr Val Phe Ala Ala Trp Leu Ala Asp Ser Gly
             20                  25                  30 tac cgc atc gag aag gcg tcc ccg gcc agg ggc ggt ggg gac tcg gag           201
Tyr Arg Ile Glu Lys Ala Ser Pro Ala Arg Gly Gly Gly Asp Ser Glu
         35                  40                  45 cgg atc gcc gat gtg ctg atc ccg ctg ctg tcc gtg gtg gga gcg gtg           249
Arg Ile Ala Asp Val Leu Ile Pro Leu Leu Ser Val Val Gly Ala Val
     50                  55                  60 gtc ctc gca gtg tgt ctg tac cgg agg tgt cgg gcc agg agg cgg ctg           297
Val Leu Ala Val Cys Leu Tyr Arg Arg Cys Arg Ala Arg Arg Arg Leu
 65                  70                  75                  80 acg ttc gac gcg tcg ctc ttc atc ggg ctg ctg tcg gcc agt tgg cag           345
Thr Phe Asp Ala Ser Leu Phe Ile Gly Leu Leu Ser Ala Ser Trp Gln
                 85                  90                  95 agt ccc ttg atg aac tgg atc aat ccg gtg ctc gcg tca aac gtc aat           393
Ser Pro Leu Met Asn Trp Ile Asn Pro Val Leu Ala Ser Asn Val Asn
            100                 105                 110 gtg ttc gga gcg gtg gcc tcg tgg ggg ccg tat gtg ccc ggt tgg cag           441
Val Phe Gly Ala Val Ala Ser Trp Gly Pro Tyr Val Pro Gly Trp Gln
        115                 120                 125 ggg gcg ggg gcg cac cag gag gcc gag ctg ccg ctg gcg acc ctg agc           489
Gly Ala Gly Ala His Gln Glu Ala Glu Leu Pro Leu Ala Thr Leu Ser
    130                 135                 140 atc tgt atg acg gcc atg atg gcc gcc gtg gcc tgc ggc aag ggc atg           537
Ile Cys Met Thr Ala Met Met Ala Ala Val Ala Cys Gly Lys Gly Met
145                 150                 155                 160 ggt ctt gcc gcc gcc cgg tgg ccg cgg ctg ggg ccg ctc cgg ctg atc           585
Gly Leu Ala Ala Ala Arg Trp Pro Arg Leu Gly Pro Leu Arg Leu Ile
                165                 170                 175 gcg ctc ggc ttt ctg ctc gtc gtg ctc ctc gac atc gcc gag ccg ctg           633
Ala Leu Gly Phe Leu Leu Val Val Leu Leu Asp Ile Ala Glu Pro Leu
            180                 185                 190 gtg tcc ttc gcg ggc gtc tcc gtg tgg acg cgg gca gtg ccc gag ctg           681
Val Ser Phe Ala Gly Val Ser Val Trp Thr Arg Ala Val Pro Glu Leu
        195                 200                 205 acc atc tgg agt ggg cac tgg tat cag ttc ccg ctg tat cag atg gtg           729
Thr Ile Trp Ser Gly His Trp Tyr Gln Phe Pro Leu Tyr Gln Met Val
    210                 215                 220 gct tcg gcg ctc ttc ggc gcc tct ttg ggg gcc gcg cgc cac ttt cgc           777
Ala Ser Ala Leu Phe Gly Ala Ser Leu Gly Ala Ala Arg His Phe Arg
225                 230                 235                 240 aac cgg cgc ggc gaa acg tgt ctg gag tcc ggg gcg gcc ctc cta ccg           825
Asn Arg Arg Gly Glu Thr Cys Leu Glu Ser Gly Ala Ala Leu Leu Pro
                245                 250                 255 gag ggc ccg agg cca tgg gtc cgg ctg ctg gcg gtg gtg ggc ggg gcc           873
```

-continued

```

Glu Gly Pro Arg Pro Trp Val Arg Leu Leu Ala Val Val Gly Gly Ala
            260                 265                 270 aac atc agc atc gcc ctc tac acc ggc gca cac ggc gca cac atc ctg    921
Asn Ile Ser Ile Ala Leu Tyr Thr Gly Ala His Gly Ala His Ile Leu
            275                 280                 285 ttc tcg ctg atg gac ggc gct ccc ccg gac cgg ctc ccc gaa ttc ttc    969
Phe Ser Leu Met Asp Gly Ala Pro Pro Asp Arg Leu Pro Glu Phe Phe
        290                 295                 300 cgt ccg gcg gcc ggc tac tga gaccgccggc accacccacg tacccgatgt      1020
Arg Pro Ala Ala Gly Tyr
305             310 gcgcgatgtg cctgatgcgc ctgatgtacc cggggtgtca tcggctcacc tgtggcgcct   1080
catgcggtga cgctccgcc tcgtccttgt tccggctcct gggctccacg accatacgga   1140
gcggccgggg                                                         1150

<210> SEQ ID NO 4
<211> LENGTH: 310
<212> TYPE: PRT
<213> ORGANISM: Streptomyces hygroscopicus

<400> SEQUENCE: 4

Val Phe Thr Leu Pro Val Thr Leu Trp Ala Cys Val Gly Ala Leu Val
  1               5                  10                  15

Leu Gly Leu Gln Val Tyr Val Phe Ala Ala Trp Leu Ala Asp Ser Gly
             20                  25                  30

Tyr Arg Ile Glu Lys Ala Ser Pro Ala Arg Gly Gly Gly Asp Ser Glu
         35                  40                  45

Arg Ile Ala Asp Val Leu Ile Pro Leu Leu Ser Val Val Gly Ala Val
     50                  55                  60

Val Leu Ala Val Cys Leu Tyr Arg Arg Cys Arg Ala Arg Arg Arg Leu
 65                  70                  75                  80

Thr Phe Asp Ala Ser Leu Phe Ile Gly Leu Leu Ser Ala Ser Trp Gln
                 85                  90                  95

Ser Pro Leu Met Asn Trp Ile Asn Pro Val Leu Ala Ser Asn Val Asn
            100                 105                 110

Val Phe Gly Ala Val Ala Ser Trp Gly Pro Tyr Val Pro Gly Trp Gln
        115                 120                 125

Gly Ala Gly Ala His Gln Glu Ala Glu Leu Pro Leu Ala Thr Leu Ser
    130                 135                 140

Ile Cys Met Thr Ala Met Met Ala Ala Val Ala Cys Gly Lys Gly Met
145                 150                 155                 160

Gly Leu Ala Ala Ala Arg Trp Pro Arg Leu Gly Pro Leu Arg Leu Ile
                165                 170                 175

Ala Leu Gly Phe Leu Leu Val Val Leu Leu Asp Ile Ala Glu Pro Leu
            180                 185                 190

Val Ser Phe Ala Gly Val Ser Val Trp Thr Arg Ala Val Pro Glu Leu
        195                 200                 205

Thr Ile Trp Ser Gly His Trp Tyr Gln Phe Pro Leu Tyr Gln Met Val
    210                 215                 220

Ala Ser Ala Leu Phe Gly Ala Ser Leu Gly Ala Ala Arg His Phe Arg
225                 230                 235                 240

Asn Arg Arg Gly Glu Thr Cys Leu Glu Ser Gly Ala Ala Leu Leu Pro
                245                 250                 255

Glu Gly Pro Arg Pro Trp Val Arg Leu Leu Ala Val Val Gly Gly Ala
            260                 265                 270
```

Asn Ile Ser Ile Ala Leu Tyr Thr Gly Ala His Gly Ala His Ile Leu
    275                 280                 285

Phe Ser Leu Met Asp Gly Ala Pro Pro Asp Arg Leu Pro Glu Phe Phe
    290                 295                 300

Arg Pro Ala Ala Gly Tyr
305                 310

<210> SEQ ID NO 5
<211> LENGTH: 215
<212> TYPE: PRT
<213> ORGANISM: Streptomyces griseochromogenes

<400> SEQUENCE: 5

Val Ile Gly Trp Ala Ala Leu Gly Ala Val Phe Leu Val Leu Gln Val
 1               5                  10                  15

Tyr Val Phe Ala Arg Trp Thr Ala Asp Gly Gly Tyr His Leu Ala Asp
                20                  25                  30

Val Ser Gly Pro Asp Gly Arg Glu Pro Gly His Arg Arg Ile Ile Asp
            35                  40                  45

Val Leu Leu Pro Ala Leu Ser Met Ala Gly Val Gly Leu Ala Phe
        50                  55                  60

Trp Leu Val Arg Arg Trp Arg Ala Glu Arg Arg Leu Ser Phe Asp Ala
 65                  70                  75                  80

Leu Leu Phe Thr Gly Val Leu Phe Ala Gly Trp Leu Ser Pro Leu Met
                85                  90                  95

Asn Trp Phe His Pro Val Leu Met Ala Asn Thr His Val Trp Gly Ala
                100                 105                 110

Val Gly Ser Trp Gly Pro Tyr Val Pro Gly Trp Arg Gly Leu Pro Pro
            115                 120                 125

Gly Lys Glu Ala Glu Leu Pro Leu Val Thr Phe Ser Leu Gly Ser Thr
130                 135                 140

Val Leu Leu Gly Val Leu Gly Cys Cys Gln Val Met Ser Arg Val Arg
145                 150                 155                 160

Glu Arg Trp Pro Gly Val Arg Pro Trp Gln Leu Val Gly Leu Ala Phe
                165                 170                 175

Leu Thr Ala Val Ala Phe Asp Leu Ser Glu Pro Phe Ile Ser Phe Ala
                180                 185                 190

Gly Val Ser Val Trp Ala Arg Ala Leu Pro Thr Val Thr Leu Trp Arg
            195                 200                 205

Gly Ala Trp Tyr Arg Ala Arg
210                 215

<210> SEQ ID NO 6
<211> LENGTH: 18
<212> TYPE: DNA
<213> ORGANISM: Streptomyces avermitilis

<400> SEQUENCE: 6
tcacgaaacc ggacacac                                                       18

<210> SEQ ID NO 7
<211> LENGTH: 18
<212> TYPE: DNA
<213> ORGANISM: Streptomyces avermitilis

<400> SEQUENCE: 7
catgatcgct gaaccgag                                                       18

```
<210> SEQ ID NO 8
<211> LENGTH: 20
<212> TYPE: DNA
<213> ORGANISM: Streptomyces avermitilis

<400> SEQUENCE: 8
ggttccggat gccgttctcg                                              20

<210> SEQ ID NO 9
<211> LENGTH: 21
<212> TYPE: DNA
<213> ORGANISM: Streptomyces avermitilis

<400> SEQUENCE: 9
aactccggtc gactcccctt c                                            21

<210> SEQ ID NO 10
<211> LENGTH: 19
<212> TYPE: DNA
<213> ORGANISM: Streptomyces avermitilis

<400> SEQUENCE: 10
gcaaggatac ggggactac                                               19

<210> SEQ ID NO 11
<211> LENGTH: 18
<212> TYPE: DNA
<213> ORGANISM: Streptomyces avermitilis

<400> SEQUENCE: 11
gaaccgaccg cctgatac                                                18

<210> SEQ ID NO 12
<211> LENGTH: 43
<212> TYPE: DNA
<213> ORGANISM: Streptomyces avermitilis

<400> SEQUENCE: 12
gggggcgggc ccgggtgcgg aggcggaaat gcccctggcg acg                    43

<210> SEQ ID NO 13
<211> LENGTH: 20
<212> TYPE: DNA
<213> ORGANISM: Streptomyces avermitilis

<400> SEQUENCE: 13
ggaaccgacc gcctgataca                                              20

<210> SEQ ID NO 14
<211> LENGTH: 46
<212> TYPE: DNA
<213> ORGANISM: Streptomyces avermitilis

<400> SEQUENCE: 14
gggggcgggc ccgggtgcgg aggcggaaat gccgctggcg acgacc                 46

<210> SEQ ID NO 15
<211> LENGTH: 20
<212> TYPE: DNA
<213> ORGANISM: Streptomyces avermitilis

<400> SEQUENCE: 15
ggaacatcac ggcattcacc                                              20
```

```
<210> SEQ ID NO 16
<211> LENGTH: 46
<212> TYPE: DNA
<213> ORGANISM: Streptomyces avermitilis

<400> SEQUENCE: 16
gggggcgggc ccgggtgcgg aggcggaaat gccgctggcg acgttc          46
```

STREPTOMYCES AVERMITILIS GENE DIRECTING THE RATIO OF B2:B1 AVERMECTINS

This application is a Divisional Application of U.S. Ser. No. 10/361,376, now granted as U.S. Pat. No. 7,388,085 B2, filed Feb. 10, 2003, which claims priority to U.S. Provisional Application No. 60/356,222, filed Feb. 12, 2002.

FIELD OF THE INVENTION

The present invention is directed to compositions and methods for the efficient production of avermectins such as "doramectin", which are primarily useful in the field of animal health. More particularly, the present invention relates to polynucleotide molecules comprising nucleotide sequences encoding an AveC gene product, which can be used to modulate the ratio of class 2:1 avermectins produced by fermentation cultures of Streptomyces avermitilis. The present invention further relates to vectors, transformed host cells, and novel mutant strains of S. avermitilis in which the aveC gene has been mutated so as to modulate the ratio of class 2:1 avermectins produced.

BACKGROUND OF THE INVENTION

2.1. Avermectins

Streptomyces species produce a wide variety of secondary metabolites, including the avermectins, which comprise a series of eight related sixteen-membered macrocyclic lactones having potent anthelmintic and insecticidal activity. The eight distinct but closely related compounds are referred to as A1a, A1b, A2a, A2b, B1a, B1 b, B2a and B2b. The "a" series of compounds refers to the natural avermectin where the substituent at the C25 position is (S)-sec-butyl, and the "b" series refers to those compounds where the substituent at the C25 position is isopropyl. The designations "A" and "B" refer to avermectins where the substituent at the C5 position is methoxy and hydroxy, respectively. The numeral "1" refers to avermectins where a double bond is present at the C22, 23 position, and the numeral "2" refers to avermectins having a hydrogen at the C22 position and a hydroxy at the C23 position. Among the related avermectins, the B1 type of avermectin, such as doramectin, is recognized as having the most effective antiparasitic and pesticidal activity, and is therefore the most commercially desirable avermectin.

The avermectins and their production by aerobic fermentation of strains of S. avermitilis are described in U.S. Pat. Nos. 4,310,519 and 4,429,042. The biosynthesis of natural avermectins is believed to be initiated endogenously from the CoA thioester analogs of isobutyric acid and S-(+)-2-methyl butyric acid.

A combination of both strain improvement through random mutagenesis and the use of exogenously supplied fatty acids has led to the efficient production of avermectin analogs. Mutants of S. avermitilis that are deficient in branched-chain 2-oxo acid dehydrogenase (bkd deficient mutants) can only produce avermectins when fermentations are supplemented with fatty acids. Screening and isolation of mutants deficient in branched-chain dehydrogenase activity (e.g., S. avermitilis, ATCC 53567) are described in European Patent (EP) 276103. Fermentation of such mutants in the presence of exogenously supplied fatty acids results in production of only the four avermectins corresponding to the fatty acid employed. Thus, supplementing fermentations of S. avermitilis (ATCC 53567) with S-(+)-2-methylbutyric acid results in production of the natural avermectins A1a, A2a, B1a and B2a; supplementing fermentations with isobutyric acid results in production of the natural avermectins A1b, A2b, B1b, and B2b; and supplementing fermentations with cyclopentanecarboxylic acid results in the production of the four novel cyclopentylavermectins A1, A2, B1, and B2.

If supplemented with other fatty acids, novel avermectins are produced. By screening over 800 potential precursors, more than 60 other novel avermectins have been identified. (See, e.g., Dutton et al, 1991, J. Antibiot. 44:357-365; and Banks et al, 1994, Roy. Soc. Chem. 147:16-26). In addition, mutants of S. avermitilis deficient in 5-O-methyltransferase activity produce essentially only the B analog avermectins. Consequently, S. avermitilis mutants lacking both branched-chain 2-oxo acid dehydrogenase and 5-O-methyltransferase activity produce only the B avermectins corresponding to the fatty acid employed to supplement the fermentation. Thus, supplementing such double mutants with S-(+)-2-methylbutyric acid results in production of only the natural avermectins B1a and B2a, while supplementing with isobutyric acid or cyclopentanecarboxylic acid results in production of the natural avermectins B1b and B2b or the novel cyclopentyl B1 and B2 avermectins, respectively. Supplementation of the double mutant strain with cyclohexane carboxylic acid is a preferred method for producing the commercially important novel avermectin, cyclohexylavermectin B1 (doramectin). The isolation and characteristics of such double mutants, e.g., S. avermitilis (ATCC 53692), is described in EP 276103.

2.2. Genes Involved In Avermectin Biosynthesis

In many cases, genes involved in production of secondary metabolites and genes encoding a particular antibiotic are found clustered together on the chromosome. Such is the case with the Streptomyces polyketide synthase gene cluster (PKS) (see Hopwood and Sherman, 1990, Ann. Rev. Genet. 24:37-66). Thus, one strategy for cloning genes in a biosynthetic pathway has been to isolate a drug resistance gene and then test adjacent regions of the chromosome for other genes related to the biosynthesis of that particular antibiotic. Another strategy for cloning genes involved in the biosynthesis of important metabolites has been complementation of mutants. For example, portions of a DNA library from an organism capable of producing a particular metabolite are introduced into a non-producing mutant and transformants screened for production of the metabolite. Additionally, hybridization of a library using probes derived from other Streptomyces species has been used to identify and clone genes in biosynthetic pathways.

Genes involved in avermectin biosynthesis (ave genes), like the genes required for biosynthesis of other Streptomyces secondary metabolites (e.g., PKS), are found clustered on the chromosome. A number of ave genes have been successfully cloned using vectors to complement S. avermitilis mutants blocked in avermectin biosynthesis. The cloning of such genes is described in U.S. Pat. No. 5,252,474. In addition, Ikeda et al., 1995, J. Antibiot. 48:532-534, describes the localization of a chromosomal region involving the C22,23 dehydration step (aveC) to a 4.82 Kb BamHI fragment of S. avermitilis, as well as mutations in the aveC gene that result in the production of a single component B2a producer. Since ivermectin, a potent anthelmintic compound, can be produced chemically from avermectin B2a, such a single component producer of avermectin B2a is considered particularly useful for commercial production of ivermectin.

U.S. Pat. No. 6,248,579 to Stutzman-Engwall et al., issued Jun. 19, 2001, describes certain mutations to the aveC gene of

*Streptomyces avermitilis* leading to a reduction in the ratio of cyclohexyl B2:cyclohexyl B1 ratio to about 0.75:1.

PCT Publication WO 01/12821 by Pfizer Products Inc., published Feb. 22, 2001, describes certain additional mutations to the aveC gene of *Streptomyces avermitilis* leading to further reductions in the ratio of cyclohexyl B2:cyclohexyl B1 ratio down to 0.40:1.

Identification of additional mutations or combinations of mutations in the aveC gene that further minimize the complexity of avermectin production, such as, e.g., mutations that further decrease the B2:B1 ratio of avermectins, would simplify production and purification of commercially important avermectins.

SUMMARY OF THE INVENTION

The present invention provides a polynucleotide molecule comprising a nucleotide sequence that is otherwise the same as the *Streptomyces avermitilis* aveC allele, the *S. avermitilis* AveC gene product-encoding sequence of plasmid pSE186 (ATCC 209604) or the nucleotide sequence of the aveC ORF of *S. avermitilis* as presented in FIG. 1 (SEQ ID NO:1), or a degenerate variant thereof, but which nucleotide sequence further comprises mutations encoding a combination of amino acid substitutions at amino acid residues corresponding to the amino acid positions of SEQ ID NO:2, such that cells of *S. avermitilis* strain ATCC 53692 in which the wild-type aveC allele has been inactivated and that express the polynucleotide molecule comprising the mutated nucleotide sequence are capable of producing a class 2:1 ratio of avermectins that is reduced compared to the ratio produced by cells of *S. avermitilis* strain ATCC 53692 that instead express only the wild-type aveC allele, wherein when the class 2:1 avermectins are cyclohexyl B2:cyclohexyl B1 avermectins, the ratio of class 2:1 avermectins is 0.35:1 or less.

In a more preferred embodiment, the ratio of cyclohexyl B2:cyclohexyl B1 avermectins is about 0.30:1 or less.

In a more preferred embodiment, the ratio of cyclohexyl B2:cyclohexyl B1 avermectins is about 0.25:1 or less.

In a more preferred embodiment, the ratio of cyclohexyl B2:cyclohexyl B1 avermectins is about 0.20:1 or less.

In a more preferred embodiment, the ratio of cyclohexyl B2:cyclohexyl B1 avermectins is about 0.10 or less.

In a particular embodiment thereof, the combination of amino acid substitutions comprises a combination selected from the group consisting of:
(a) D48E, A61T, A89T, S138T, A139T, G179S, A198G, P289L;
(b) G40S, D48E, L136P, G179S, E238D;
(c) D48E, L136P, R163Q, G179S;
(d) D48E, L136P, R163Q, G179S, E238D;
(e) D48E, L136P, R163Q, G179S, A200G, E238D;
(f) D48E, L136P, G179S, E238D;
(g) D48E, A61T, L136P, G179S, E238D;
(h) D48E, A61T, L136P, G179S;
(i) D48E, A89T, S138T, A139T, G179S;
(j) D48E, A61T, L136P, G179S, A198G, P202S, E238D, P289L;
(k) D48E, A61T, L136P, S138T, A139F, G179S, E238D, P289L;
(l) D48E, L136P, G179S, A198G, E238D, P289L;
(m) D48E, A61T, S138T, A139F, G179S, A198G, P289L;
(n) D48E, L84P, G111V, S138T, A139T, G179S, A198G, P289L;
(o) Y28C, D48E, A61T, A89T, S138T, A139T, G179S, E238D;
(p) D48E, A61T, A107T, S108G, L136P, G179S, S192A, E238D, P289L;
(q) D48E, L136P, G179S, R250W;
(r) D48E, A89T, S138T, A139T, R163Q, G179S;
(s) D48E, L136P, G179S, A198G, P289L;
(t) D48E, F78L, A89T, L136P, G179S;
(u) D48E, A89T, S138T, A139T, G179S, E238D, F278L;
(v) D48E, A89T, L136P, R163Q, G179S;
(w) D48E, A61T, A89T, G111V, S138T, A139F, G179S, E238D, P289L;
(x) D25G, D48E, A89T, L136P, S138T, A139T, V141A, I159T, R163Q, G179S;
(y) D48E, A89T, S90G, L136P, R163Q, G179S, E238D;
(z) D48E, A61T, A89T, G 111V, S138T, A139T, G179S, E238D, P289L;
(aa) D48E, A89T, S138T, A139T, G179S;
(ab) D48E, L136P, R163Q, G179S, S231L;
(ac) D48E, L136P, S138T, A139F, G179S, V196A, E238D;
(ad) D48E, A61T, A89T, F99S, S138T, A139T, G179S, E238D;
(ae) G35S, D48E, A89T, S138T, A139T, G179S, P289L;
(af) D48E, A61T, A89T, S138T, A139T, G179S, V196A, E238D;
(ag) D48E, A89T, G111V, S138T, A139T, G179S, A198G, E238D;
(ah) S41G, D48E, A89T, L136P, G179S;
(ai) D48E, A89T, L136P, R163Q, G179S, P252S;
(aj) D48E, A89T, L136P, G179S, F234S;
(ak) D48E, A89T, L136P, R163Q, G179S, E238D;
(al) Q36R, D48E, A89T, L136P, G179S, E238D;
(am) D48E, A89T, L136P, R163Q, G179S;
(an) D48E, A89T, S138T, G179S;
(ao) D48E, A89T, L136P, G179S, E238D;
(ap) D48E, A89T, L136P, K154E, G179S, E238D;
(aq) D48E, A89T, S138T, A139T, K154R, G179S, V196A, P289L;
(ar) D48E, A89T, S138T, A139F, G179S, V196A, E238D;
(as) D48E, A61T, A89T, L136P, G179S, V196A, A198G, P289L;
(at) D48E, A61T, S138T. A139F, G179S, G196A, E238D, P289L;
(au) D48E, A89T, L136P, G179S;
(av) D48E, A89T, V120A, L136P, G179S;
(aw) D48E, A61T, A89T, S138T, A139F, G179S, V196A, A198G, E238D;
(ax) D48E, A61T, A89T, G111V, S138T, A139F, G179S, V196A, E238D;
(ay) D48E, A61T, A89T, S138T, A139T, G179S, V196A, E238D, P289L;
(az) D48E, A61T, A89T, L136P, S138T, A139F, G179S, A198G, E238D;
(ba) D48E, A89T, S138T, A139F, G179S, A198G, V220A;
(bb) D48E, A61T, A89T, S138T, A139T, G179S, V196A, E238D, R239H, P289L;
(bc) D48E, A61T, A89T, L136P, G179S, P289L;
(bd) D48E, A89T, S138T, A139T, G179S, V196A, E238D, P289L;
(be) D48E, A61T, A89T, S138T, A139F, G179S, V196A, E238D;
(da) S41G, D48E, A61T, R71L, A89T, L136M, S138T, A139T, T149S, G179S, V196A, E238D, F278L, P289L;
(db) S41G, D48E, A61T, R71L, A89T, L136M, S138T, A139T, T149S, F176C, G179S, V196A, E238D, P289L;
(dc) D48E, R71L, A89T, L136P, T149S, F176C, G179S, E238D, I280V;

(dd) D48E, A61T, R71L, W110L, T149S, G179S, V196A, L206M, E238D, V271A, I280V;
(de) D48E, A61T, R71L, A89T, L136M, S138T, A139T, T149S, G179S, V196A, E238D, H279Q, P289L;
(df) D48E, A61T, R71L, A89T, L136M, S138T, A139T, T149S, G179S, V196A, E238D, G287E, P289Q;
(dg) D48E, A61T, R71L, A89T, L136M, S138T, A139T, T149S, G179S, V196A, E238D, P289L;
(dh) D48E, A61T, R71L, A89T, A139T, T149S, F176C, G179S, V196A, E238D, V285G, P289L;
(di) Q38R, D48E, A61T, R71L, L87V, A89T, L136M, S138T, A139T, T149S, G179S, V196A, E238D, P289L;

non-limiting embodiment, the mutated aveC allele or degenerate variant thereof encodes an AveC gene product comprising a combination of amino acid substitutions selected from the group consisting of (f) through (be) and (da) through (es) listed above.

In a more preferred embodiment thereof, the ratio of cyclohexyl B2:cyclohexyl B1 avermectins is about 0.25:1 or less. In a non-limiting embodiment, the mutated aveC allele or degenerate variant thereof encodes an AveC gene product comprising a combination of amino acid substitutions selected from the group consisting of (w) through (be) and (da) through (es) listed above.

In a more preferred embodiment thereof, the ratio of cyclohexyl B2:cyclohexyl B1 avermectins is about 0.20:1 or less. In a non-limiting embodiment, the mutated aveC allele or degenerate variant thereof encodes an AveC gene product comprising a combination of amino acid substitutions selected from the group consisting of (ao) through (be) and (da) through (es) listed above.

In a more preferred embodiment thereof, the ratio of cyclohexyl B2:cyclohexyl B1 avermectins is about 0.10:1 or less. In a non-limiting embodiment, the mutated aveC allele or degenerate variant thereof encodes an AveC gene product comprising a combination of amino acid substitutions selected from the group consisting of (ea) through (es) listed above.

The present invention further provides a method for making a novel strain of Streptomyces avermitilis, comprising (i) mutating the aveC allele in a cell of a strain of S. avermitilis, which mutation results in a combination of amino acid substitutions in the AveC gene product, or (ii) introducing into a cell of a strain of S. avermitilis a mutated aveC allele or degenerate variant thereof encoding an AveC gene product comprising a combination of amino acid substitutions, wherein the combination of amino acid substitutions is selected from the group consisting of (bf), (bg) and (ca) through (cs) listed above.

In a preferred embodiment thereof, cells of S. avermitilis comprising such a mutated aveC allele or degenerate variant are capable of producing cyclohexyl B2:cyclohexyl B1 avermectins in a ratio of about 1.17:1 or less.

The present invention further provides a cell of a Streptomyces species that comprises a mutated S. avermitilis aveC allele or degenerate variant thereof encoding an AveC gene product comprising a combination of amino acid substitutions selected from (a) through (es) listed above. In a preferred embodiment thereof, the species of Streptomyces is S. avermitilis.

The present invention further provides a cell of Streptomyces avermitilis capable of producing cyclohexyl B2:cyclohexyl B1 avermectins in a ratio of 0.35:1 or less. In a non-limiting embodiment thereof, the cell comprises a mutated aveC allele or degenerate variant thereof encoding an AveC gene product comprising a combination of amino acid substitutions selected from the group consisting of (a) through (be) and (da) through (es) listed above.

In a preferred embodiment thereof, the ratio of cyclohexyl B2:cyclohexyl B1 avermectins is about 0.30:1 or less. In a non-limiting embodiment thereof, the cells comprise a mutated aveC allele or degenerate variant thereof encoding an AveC gene product comprising a combination of amino acid substitutions selected from the group consisting of (f) through (be) and (da) through (es) listed above.

In a more preferred embodiment thereof, the ratio of cyclohexyl B2:cyclohexyl B1 avermectins is about 0.25:1 or less. In a non-limiting embodiment thereof, the cells comprise a mutated aveC allele or degenerate variant thereof encoding an AveC gene product comprising a combination of amino acid substitutions selected from the group consisting of (w) through (be) and (da) through (es) listed above.

In a more preferred embodiment thereof, the ratio of cyclohexyl B2:cyclohexyl B1 avermectins is about 0.20:1 or less. In a non-limiting embodiment thereof, the cells comprise a mutated aveC allele or degenerate variant thereof encoding an AveC gene product comprising a combination of amino acid substitutions selected from the group consisting of (ao) through (be) and (da) through (es) listed above.

In a more preferred embodiment thereof, the ratio of cyclohexyl B2:cyclohexyl B1 avermectins is about 0.10:1 or less. In a non-limiting embodiment thereof, the cells comprise a mutated aveC allele or degenerate variant thereof encoding an AveC gene product comprising a combination of amino acid substitutions selected from the group consisting of (ea) through (es) listed above.

The present invention further provides a cell of a Streptomyces species, comprising a mutated S. avermitilis aveC allele or degenerate variant thereof encoding an AveC gene product comprising a combination of amino acid substitutions selected from the group consisting of (bf), (bg), and (ca) through (cs) listed above. In a preferred embodiment thereof, the species of Streptomyces is S. avermitilis. In a more preferred embodiment, the cell is a cell of S. avermitilis capable of producing cyclohexyl B2:cyclohexyl B1 avermectins in a ratio of about 1.17:1 or less.

The present invention further provides a process for producing avermectins, comprising culturing a strain of Streptomyces avermitilis cells of the present invention in culture media under conditions that permit or induce the production of avermectins therefrom, and recovering said avermectins from the culture.

The present invention further provides a composition of cyclohexyl B2:cyclohexyl B1 avermectins produced by cells of Streptomyces avermitilis, comprising the cyclohexyl B2:cyclohexyl B1 avermectins present in a culture medium in which the cells have been cultured, wherein the ratio of the cyclohexyl B2:cyclohexyl B1 avermectins present in the culture medium is 0.35:1 or less, preferably about 0.30:1 or less, more preferably about 0.25:1 or less, more preferably about 0.20:1 or less and more preferably about 0.10:1 or less.

In a particular embodiment, the composition of cyclohexyl B2:cyclohexyl B1 avermectins is produced by cells of a strain of S. avermitilis that express a mutated aveC allele or degenerate variant thereof which encodes a gene product that results in the reduction of the class 2:1 ratio of cyclohexyl B2:cyclohexyl B1 avermectins produced by the cells compared to cells of the same strain of S. avermitilis that do not express the mutated aveC allele but instead express only the wild-type aveC allele.

In a preferred embodiment thereof, where the composition is cyclohexyl B2:cyclohexyl B1 avermectins in a ratio of 0.35:1 or less, the composition is produced by cells comprising a mutated aveC allele or degenerate variant thereof encoding an AveC gene product comprising a combination of amino acid substitutions selected from the group consisting of (a) through (be) and (da) through (es) listed above.

In a further preferred embodiment thereof, where the composition is cyclohexyl B2:cyclohexyl B1 avermectins in a ratio of about 0.30:1 or less, the composition is produced by cells comprising a mutated aveC allele or degenerate variant thereof encoding an AveC gene product comprising a combination of amino acid substitutions selected from the group consisting of (f) through (be) and (da) through (es) listed above.

In a further preferred embodiment thereof where the composition is cyclohexyl B2:cyclohexyl B1 avermectins in a ratio of about 0.25:1 or less, the composition is produced by cells comprising a mutated aveC allele or degenerate variant thereof encoding an AveC gene product comprising a combination of amino acid substitutions selected from the group consisting of (w) through (be) and (da) through (es) listed above.

In a further preferred embodiment thereof, where the composition is cyclohexyl B2:cyclohexyl B1 avermectins in a ratio of about 0.20:1 or less, the composition is produced by cells comprising a mutated aveC allele or degenerate variant thereof encoding an AveC gene product comprising a combination of amino acid substitutions selected from the group consisting of (ao) through (be) and (da) through (es) listed above.

In a further preferred embodiment thereof, where the composition is cyclohexyl B2:cyclohexyl B1 avermectins in a ratio of about 0.10:1 or less, the composition is produced by cells comprising a mutated aveC allele or degenerate variant thereof encoding an AveC gene product comprising a combination of amino acid substitutions selected from the group consisting of (ea) through (es) listed above The present invention further provides a composition of cyclohexyl B2:cyclohexyl B1 avermectins produced by cells of *Streptomyces avermitilis*, comprising the cyclohexyl B2:cyclohexyl B1 avermectins present in a culture medium in which the cells have been cultured, wherein the ratio of the cyclohexyl B2:cyclohexyl B1 avermectins present in the culture medium is about 1.17:1 or less, and produced by cells comprising a mutated aveC allele or degenerate variant thereof encoding an AveC gene product comprising a combination of amino acid substitutions selected from the group consisting of (bf) and (bg) and (ca) through (cs) listed above.

BRIEF DESCRIPTION OF THE FIGURES

FIG. 1. DNA sequence (SEQ ID NO:1) comprising the *S. avermitilis* aveC ORF, and deduced amino acid sequence (SEQ ID NO:2).

FIG. 5. HPLC analysis of fermentation products produced by *S. avermitilis* strains. Peak quantitation was performed by comparison to standard quantities of cyclohexyl B1. Cyclohexyl B2 retention time was 7.4-7.7 min; cyclohexyl B1 retention time was 11.9-12.3 min.

FIG. 6A-M. Compiled list of combinations of amino acid substitutions encoded by mutations to the aveC allele as identified by a second round of "gene shuffling", and their effects on the ratio of cyclohexyl B2:cyclohexyl B1 production. For each plasmid, in the column entitled "Mutations", the upper box lists the amino acid substitutions, and the lower box lists the nucleotide base changes resulting in those amino acid substitutions. Nucleotide base changes in parentheses are silent changes, i.e., they do not result in changes to the amino acid sequence.

DETAILED DESCRIPTION OF THE INVENTION

Figure 2:
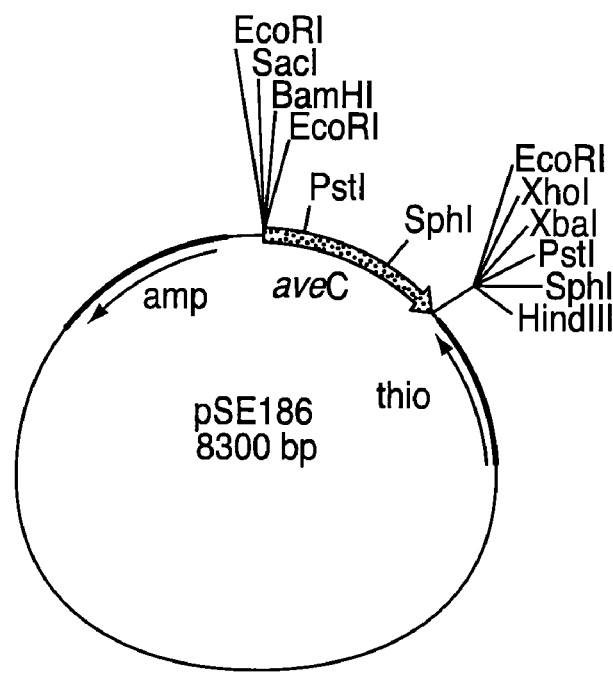
FIG. 2. Plasmid vector pSE186 (ATCC 209604) comprising the entire ORF of the aveC gene of *S. avermitilis*.

The present invention relates to the identification and characterization of polynucleotide molecules having nucleotide sequences that encode the AveC gene product from *Streptomyces avermitilis*, the construction of novel strains of *S. avermitilis* that can be used to screen mutated AveC gene products for their effect on avermectin production, and the discovery that certain mutated AveC gene products can reduce the ratio of B2:B1 avermectins produced by *S. avermitilis*. By way of example, the invention is described in the sections below for a polynucleotide molecule having either a nucleotide sequence that is the same as the *S. avermitilis* AveC gene product-encoding sequence of plasmid pSE186 (ATCC 209604), or the nucleotide sequence of the ORF of FIG. 1 (SEQ ID NO:1), and for polynucleotides molecules having mutated nucleotide sequences derived therefrom and degenerate variants thereof. However, the principles set forth in the present invention can be analogously applied to other polynucleotide molecules, including aveC homolog genes from other *Streptomyces* species including, e.g., *S. hygroscopicus* and *S. griseochromogenes*, among others.

5.1. Polynucleotide Molecules Encoding the *S. avermitilis* AveC Gene Product

The present invention provides an isolated polynucleotide molecule comprising the complete aveC ORF of *S. avermitilis* or a substantial portion thereof, which isolated polynucleotide molecule lacks the next complete ORF that is located downstream from the aveC ORF in situ in the *S. avermitilis* chromosome.

The isolated polynucleotide molecule of the present invention preferably comprises a nucleotide sequence that is the same as the *S. avermitilis* AveC gene product-encoding sequence of plasmid pSE186 (ATCC 209604), or that is the same as the nucleotide sequence of the ORF of FIG. 1 (SEQ ID NO:1) or substantial portion thereof. As used herein, a "substantial portion" of an isolated polynucleotide molecule comprising a nucleotide sequence encoding the *S. avermitilis* AveC gene product means an isolated polynucleotide molecule comprising at least about 70% of the complete aveC ORF sequence shown in FIG. 1 (SEQ ID NO:1), and that encodes a functionally equivalent AveC gene product. In this regard, a "functionally equivalent" AveC gene product is defined as a gene product that, when expressed in *S. avermitilis* strain ATCC 53692 in which the native aveC allele has been inactivated, results in the production of substantially the same ratio and amount of avermectins as produced by *S. avermitilis* strain ATCC 53692 which instead expresses only the wild-type, functional aveC allele native to *S. avermitilis* strain ATCC 53692.

In addition to the nucleotide sequence of the aveC ORF, the isolated polynucleotide molecule of the present invention can further comprise nucleotide sequences that naturally flank the aveC gene in situ in *S. avermitilis*, such as those flanking nucleotide sequences shown in FIG. 1 (SEQ ID NO:1).

The present invention further provides an isolated polynucleotide molecule comprising the nucleotide sequence of SEQ ID NO:1 or a degenerate variant thereof, as based on the known degeneracy of the genetic code.

As used herein, the terms "polynucleotide molecule," "polynucleotide sequence," "coding sequence," "open-reading frame," and "ORF" are intended to refer to both DNA and RNA molecules, which can either be single-stranded or double-stranded, and that can be transcribed and translated (DNA), or translated (RNA), into an AveC gene product, or into a polypeptide that is homologous to an AveC gene product in an appropriate host cell expression system when placed under the control of appropriate regulatory elements. A coding sequence can include but is not limited to prokaryotic sequences, cDNA sequences, genomic DNA sequences, and chemically synthesized DNA and RNA sequences.

The nucleotide sequence shown in FIG. 1 (SEQ ID NO:1) comprises four different GTG codons at bp positions 42, 174, 177 and 180. As previously described in U.S. Pat. No. 6,248, 579, multiple deletions of the 5' region of the aveC ORF (FIG. 1; SEQ ID NO:1) were constructed to help define which of these codons could function in the aveC ORF as start sites for protein expression. Deletion of the first GTG site at bp 42 did not eliminate AveC activity. Additional deletion of all of the GTG codons at bp positions 174, 177 and 180 together eliminated AveC activity, indicating that this region is necessary for protein expression. The present invention thus encompasses variable length aveC ORFs.

The present invention further provides a polynucleotide molecule having a nucleotide sequence that is homologous to the S. avermitilis AveC gene product-encoding sequence of plasmid pSE186 (ATCC 209604), or to the nucleotide sequence of the aveC ORF presented in FIG. 1 (SEQ ID NO:1) or substantial portion thereof. The term "homologous" when used to refer to a polynucleotide molecule that is homologous to an S. avermitilis AveC gene product-encoding sequence means a polynucleotide molecule having a nucleotide sequence: (a) that encodes the same AveC gene product as the S. avermitilis AveC gene product-encoding sequence of plasmid pSE186 (ATCC 209604), or that encodes the same AveC gene product as the nucleotide sequence of the aveC ORF presented in FIG. 1 (SEQ ID NO:1), but that includes one or more silent changes to the nucleotide sequence according to the degeneracy of the genetic code (i.e., a degenerate variant); or (b) that hybridizes to the complement of a polynucleotide molecule having a nucleotide sequence that encodes the amino acid sequence encoded by the AveC gene product-encoding sequence of plasmid pSE186 (ATCC 209604) or that encodes the amino acid sequence shown in FIG. 1 (SEQ ID NO:2) under moderately stringent conditions, i.e., hybridization to filter-bound DNA in 0.5 M NaHPO$_4$, 7% sodium dodecyl sulfate (SDS), 1 mM EDTA at 65° C., and washing in 0.2×SSC/0.1% SDS at 42° C. (see Ausubel et al (eds.), 1989, Current Protocols in Molecular Biology, Vol. I, Green Publishing Associates, Inc., and John Wiley & Sons, Inc., New York, at p. 2.10.3), and encodes a functionally equivalent AveC gene product as defined above. In a preferred embodiment, the homologous polynucleotide molecule hybridizes to the complement of the AveC gene product-encoding nucleotide sequence of plasmid pSE186 (ATCC 209604) or to the complement of the nucleotide sequence of the aveC ORF presented in FIG. 1 (SEQ ID NO:1) or substantial portion thereof under highly stringent conditions, i.e., hybridization to filter-bound DNA in 0.5 M NaHPO$_4$, 7% SDS, 1 mM EDTA at 65° C., and washing in 0.1×SSC/0.1% SDS at 68° C. (Ausubel et al., 1989, above), and encodes a functionally equivalent AveC gene product as defined above.

The activity of an AveC gene product and potential functional equivalents thereof can be determined through HPLC analysis of fermentation products, as described in the examples below. Polynucleotide molecules having nucleotide sequences that encode functional equivalents of the S. avermitilis AveC gene product may include naturally occurring aveC genes present in other strains of S. avermitilis, aveC homolog genes present in other species of Streptomyces, and mutated aveC alleles, whether naturally occurring or engineered.

The present invention further provides a polynucleotide molecule comprising a nucleotide sequence that encodes a polypeptide having an amino acid sequence that is homologous to the amino acid sequence encoded by the AveC gene product-encoding sequence of plasmid pSE186 (ATCC 209604), or the amino acid sequence of FIG. 1 (SEQ ID NO:2) or substantial portion thereof. As used herein, a "substantial portion" of the amino acid sequence of FIG. 1 (SEQ ID NO:2) means a polypeptide comprising at least about 70% of the amino acid sequence shown in FIG. 1 (SEQ ID NO:2), and that constitutes a functionally equivalent AveC gene product, as defined above.

As used herein to refer to amino acid sequences that are homologous to the amino acid sequence of an AveC gene product from S. avermitilis, the term "homologous" refers to a polypeptide which otherwise has the amino acid sequence of FIG. 1 (SEQ ID NO:2), but in which one or more amino acid residues has been conservatively substituted with a different amino acid residue, wherein said amino acid sequence has at least about 70%, more preferably at least about 80%, and most preferably at least about 90% amino acid sequence identity to the polypeptide encoded by the AveC gene product-encoding sequence of plasmid pSE186 (ATCC 209604) or the amino acid sequence of FIG. 1 (SEQ ID NO:2) as determined by any standard amino acid sequence identity algorithm, such as the BLASTP algorithm (GENBANK, NCBI), and where such conservative substitution results in a functionally equivalent gene product, as defined above. Conservative amino acid substitutions are well known in the art. Rules for making such substitutions include those described by Dayhof, M.D., 1978, Nat. Biomed. Res. Found., Washington, D.C., Vol. 5, Sup. 3, among others. More specifically, conservative amino acid substitutions are those that generally take place within a family of amino acids that are related in the acidity or polarity. Genetically encoded amino acids are generally divided into four groups: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan and tyrosine are also jointly classified as aromatic amino acids. One or more replacements within any particular group, e.g., of a leucine with an isoleucine or valine, or of an aspartate with a glutamate, or of a threonine with a serine, or of any other amino acid residue with a structurally related amino acid residue, e.g., an amino acid residue with similar acidity or polarity, or with similarity in some combination thereof, will generally have an insignificant effect on the function of the polypeptide.

Production and manipulation of the polynucleotide molecules disclosed herein are within the skill in the art and can be carried out according to recombinant techniques described, e.g., in Maniatis, et al., 1989, Molecular Cloning, A Laboratory Manual, Cold Spring Harbor Laboratory Press, Cold Spring Harbor, N.Y.; Ausubel, et al., 1989, Current Protocols In Molecular Biology, Greene Publishing Associates & Wiley Interscience, NY; Sambrook, et al., 1989, Molecular Cloning: A Laboratory Manual, 2d ad., Cold Spring Harbor Laboratory Press, Cold Spring Harbor, N.Y.; Innis et al. (ads), 1995, PCR Strategies, Academic Press, Inc., San Diego; and Erlich (ed), 1992, PCR Technology, Oxford University Press, New York, all of which are incorporated herein by reference. Polynucleotide clones encoding AveC gene products or AveC homolog gene products can be identified using any method known in the art, including but not limited to the methods set forth in Section 7, below. Genomic DNA libraries can be screened for aveC and aveC homolog coding sequences using techniques such as the methods set forth in Benton and Davis, 1977, Science 196:180, for bacteriophage libraries, and in Grunstein and Hogness, 1975, Proc. Natl. Acad. Sci. USA, 72:3961-3965, for plasmid libraries. Polynucleotide molecules having nucleotide sequences known to include the aveC ORF, as present, e.g., in plasmid pSE186 (ATCC 209604), or in plasmid pSE119 (described in Section 7, below), can be used as probes in these screening experiments. Alternatively, oligonucleotide probes can be synthesized that correspond to nucleotide sequences deduced from partial or complete amino acid sequences of the purified AveC homolog gene product.

5.2. Recombinant Systems

5.2.1. Cloning And Expression Vectors

The present invention further provides recombinant cloning vectors and expression vectors which are useful in cloning or expressing polynucleotide molecules of the present invention comprising, e.g., the aveC ORF of *S. avermitilis* or any aveC homolog ORFs. In a non-limiting embodiment, the present invention provides plasmid pSE186 (ATCC 209604), which comprises the complete ORF of the aveC gene of *S. avermitilis*.

All of the following description regarding the aveC ORF from *S. avermitilis*, or a polynucleotide molecule comprising the aveC ORF from *S. avermitilis* or portion thereof, or an *S. avermitilis* AveC gene product, also refers to mutated aveC alleles as described below, unless indicated explicitly or by context.

A variety of different vectors have been developed for specific use in *Streptomyces*, including phage, high copy number plasmids, low copy number plasmids, and *E. coli-Streptomyces* shuttle vectors, among others, and any of these can be used to practice the present invention. A number of drug resistance genes have also been cloned from *Streptomyces*, and several of these genes have been incorporated into vectors as selectable markers. Examples of current vectors for use in *Streptomyces* are presented, among other places, in Hutchinson, 1980, Applied Biochem. Biotech. 16:169-190.

Recombinant vectors of the present invention, particularly expression vectors, are preferably constructed so that the coding sequence for the polynucleotide molecule of the invention is in operative association with one or more regulatory elements necessary for transcription and translation of the coding sequence to produce a polypeptide. As used herein, the term "regulatory element" includes but is not limited to nucleotide sequences that encode inducible and non-inducible promoters, enhancers, operators and other elements known in the art that serve to drive and/or regulate expression of polynucleotide coding sequences. Also, as used herein, the coding sequence is in "operative association" with one or more regulatory elements where the regulatory elements effectively regulate and allow for the transcription of the coding sequence or the translation of its mRNA, or both.

Typical plasmid vectors that can be engineered to contain a polynucleotide molecule of the present invention include pCR-Blunt, pCR2.1 (Invitrogen), pGEM3Zf (Promega), and the shuttle vector pWHM3 (Vara et al., 1989, J. Bact. 171: 5872-5881), among many others.

Methods are well-known in the art for constructing recombinant vectors containing particular coding sequences in operative association with appropriate regulatory elements, and these can be used to practice the present invention. These methods include in vitro recombinant techniques, synthetic techniques, and in vivo genetic recombination. See, e.g., the techniques described in Maniatis et al., 1989, above; Ausubel et al., 1989, above; Sambrook et al., 1989, above; Innis et al., 1995, above; and Erlich, 1992, above.

The regulatory elements of these vectors can vary in their strength and specificities. Depending on the host/vector system utilized, any of a number of suitable transcription and translation elements can be used. Non-limiting examples of transcriptional regulatory regions or promoters for bacteria include the β-gal promoter, the T7 promoter, the TAC promoter, λ left and right promoters, trp and lac promoters, trp-lac fusion promoters and, more specifically for *Streptomyces*, the promoters ermE, melC, and tipA, etc. In a specific embodiment, an expression vector can be generated that contains the aveC ORF or mutated ORF thereof cloned adjacent to a strong constitutive promoter, such as the ermE promoter from *Saccharopolyspora erythraea*. As described in U.S. Pat. No. 6,248,579, a vector comprising the ermE promoter was transformed into *S. avermitilis*, and subsequent HPLC analysis of fermentation products indicated an increased titer of avermectins produced compared to production by the same strain which instead expresses only the wild-type aveC allele.

Fusion protein expression vectors can be used to express an AveC gene product-fusion protein. The purified fusion protein can be used to raise antisera against the AveC gene product, to study the biochemical properties of the AveC gene product, to engineer AveC fusion proteins with different biochemical activities, or to aid in the identification or purification of the expressed AveC gene product. Possible fusion protein expression vectors include but are not limited to vectors incorporating sequences that encode β-galactosidase and trpE fusions, maltose-binding protein fusions, glutathione-S-transferase fusions and polyhistidine fusions (carrier regions). In an alternative embodiment, an AveC gene product or a portion thereof can be fused to an AveC homolog gene product, or portion thereof, derived from another species or strain of *Streptomyces*, such as, e.g., *S. hygroscopicus* or *S. griseochromogenes*. Such hybrid vectors can be transformed into *S. avermitilis* cells and tested to determine their effect, e.g., on the ratio of class 2:1 avermectin produced.

AveC fusion proteins can be engineered to comprise a region useful for purification. For example, AveC-maltose-binding protein fusions can be purified using amylose resin; AveC-glutathione-S-transferase fusion proteins can be purified using glutathione-agarose beads; and AveC-polyhistidine fusions can be purified using divalent nickel resin. Alternatively, antibodies against a carrier protein or peptide can be used for affinity chromatography purification of the fusion protein. For example, a nucleotide sequence coding for the target epitope of a monoclonal antibody can be engineered into the expression vector in operative association with the regulatory elements and situated so that the expressed epitope is fused to the AveC polypeptide. For example, a nucleotide sequence coding for the FLAG™ epitope tag (International Biotechnologies Inc.), which is a hydrophilic marker peptide, can be inserted by standard techniques into the expression vector at a point corresponding, e.g., to the carboxyl terminus of the AveC polypeptide. The expressed AveC polypeptide-FLAG™ epitope fusion product can then be detected and affinity-purified using commercially available anti-FLAG™ antibodies.

The expression vector encoding the AveC fusion protein can also be engineered to contain polylinker sequences that encode specific protease cleavage sites so that the expressed AveC polypeptide can be released from the carrier region or fusion partner by treatment with a specific protease. For example, the fusion protein vector can include DNA sequences encoding thrombin or factor Xa cleavage sites, among others.

A signal sequence upstream from, and in reading frame with, the aveC ORF can be engineered into the expression vector by known methods to direct the trafficking and secretion of the expressed gene product. Non-limiting examples of signal sequences include those from α-factor, immunoglobulins, outer membrane proteins, penicillinase, and T-cell receptors, among others.

To aid in the selection of host cells transformed or transfected with cloning or expression vectors of the present invention, the vector can be engineered to further comprise a coding sequence for a reporter gene product or other selectable marker. Such a coding sequence is preferably in operative association with the regulatory element coding sequences, as described above. Reporter genes that are useful in the invention are well-known in the art and include those encoding green fluorescent protein, luciferase, xylE, and tyrosinase, among others. Nucleotide sequences encoding selectable markers are well known in the art, and include those that encode gene products conferring resistance to antibiotics or anti-metabolites, or that supply an auxotrophic requirement. Examples of such sequences include those that encode resistance to erythromycin, thiostrepton or kanamycin, among many others.

5.2.2. Transformation of Host Cells

The present invention further provides transformed host cells comprising a polynucleotide molecule or recombinant vector of the invention, and novel strains or cell lines derived therefrom. Host cells useful in the practice of the invention are preferably *Streptomyces* cells, although other prokaryotic cells or eukaryotic cells can also be used. Such transformed host cells typically include but are not limited to microorganisms, such as bacteria transformed with recombinant bacteriophage DNA, plasmid DNA or cosmid DNA vectors, or yeast transformed with recombinant vectors, among others.

The polynucleotide molecules of the present invention are intended to function in *Streptomyces* cells, but can also be transformed into other bacterial or eukaryotic cells, e.g., for cloning or expression purposes. A strain of *E. coli* can typically be used, such as, e.g., the DH5α strain, available from the American Type Culture Collection (ATCC), Rockville, Md., USA (Accession No. 31343), and from commercial sources (Stratagene). Preferred eukaryotic host cells include yeast cells, although mammalian cells or insect cells can also be utilized effectively.

The recombinant expression vector of the invention is preferably introduced, e.g., transformed or transfected, into one or more host cells of a substantially homogeneous culture of cells. The expression vector is generally introduced into host cells in accordance with known techniques, such as, e.g., by protoplast transformation, calcium phosphate precipitation, calcium chloride treatment, microinjection, electroporation, transfection by contact with a recombined virus, liposome-mediated transfection, DEAE-dextran transfection, transduction, conjugation, or microprojectile bombardment. Selection of transformants can be conducted by standard procedures, such as by selecting for cells expressing a selectable marker, e.g., antibiotic resistance, associated with the recombinant vector, as described above.

Once the expression vector is introduced into the host cell, the integration and maintenance of the aveC coding sequence either in the host cell chromosome or episomally can be confirmed by standard techniques, e.g., by Southern hybridization analysis, restriction enzyme analysis, PCR analysis, including reverse transcriptase PCR (rt-PCR), or by immunological assay to detect the expected gene product. Host cells containing and/or expressing the recombinant aveC coding sequence can be identified by any of at least four general approaches which are well-known in the art, including: (i) DNA-DNA, DNA-RNA, or RNA-antisense RNA hybridization; (ii) detecting the presence of "marker" gene functions; (iii) assessing the level of transcription as measured by the expression of aveC-specific mRNA transcripts in the host cell; and (iv) detecting the presence of mature polypeptide product as measured, e.g., by immunoassay or by the presence of AveC biological activity (e.g., the production of specific ratios and amounts of avermectins indicative of AveC activity in, e.g., *S. avermitilis* host cells).

5.2.3. Expression And Characterization of a Recombinant AveC Gene Product

Once the native or mutated aveC coding sequence has been stably introduced into an appropriate host cell, the transformed host cell is clonally propagated, and the resulting cells can be grown under conditions conducive to the maximum production of the native or mutated AveC gene product. Such conditions typically include growing cells to high density. Where the expression vector comprises an inducible promoter, appropriate induction conditions such as, e.g., temperature shift, exhaustion of nutrients, addition of gratuitous inducers (e.g., analogs of carbohydrates, such as isopropyl-β-D-thiogalactopyranoside (IPTG)), accumulation of excess metabolic by-products, or the like, are employed as needed to induce expression.

Where the expressed AveC gene product is retained inside the host cells, the cells are harvested and lysed, and the product isolated and purified from the lysate under extraction conditions known in the art to minimize protein degradation such as, e.g., at 4° C., or in the presence of protease inhibitors, or both. Where the expressed AveC gene product is secreted from the host cells, the exhausted nutrient medium can simply be collected and the product isolated therefrom.

The expressed AveC gene product can be isolated or substantially purified from cell lysates or culture medium, as appropriate, using standard methods, including but not limited to any combination of the following methods: ammonium sulfate precipitation, size fractionation, ion exchange chromatography, HPLC, density centrifugation, and affinity chromatography. Where the expressed AveC gene product exhibits biological activity, increasing purity of the preparation can be monitored at each step of the purification procedure by use of an appropriate assay. Whether or not the expressed AveC gene product exhibits biological activity, it can be detected as based, e.g., on size, or reactivity with an antibody otherwise specific for AveC, or by the presence of a fusion tag. As used herein, an AveC gene product is "substantially purified" where the product constitutes more than about 20 wt % of the protein in a particular preparation. Also, as used herein, an AveC gene product is "isolated" where the product constitutes at least about 80 wt % of the protein in a particular preparation.

The present invention thus provides a recombinantly-expressed isolated or substantially purified *S. avermitilis* AveC gene product comprising the amino acid sequence encoded by the AveC gene product-encoding sequence of plasmid pSE186 (ATCC 209604), or the amino acid sequence of FIG. 1 (SEQ ID NO:2) or a substantial portion thereof, and mutated versions and degenerate variants thereof.

The present invention further provides a method for producing an AveC gene product, comprising culturing a host cell transformed with a recombinant expression vector, said vector comprising a polynucleotide molecule having a nucleotide sequence encoding the AveC gene product, which polynucleotide molecule is in operative association with one or more regulatory elements that control expression of the polynucleotide molecule in the host cell, under conditions conducive to the production of the recombinant AveC gene product, and recovering the AveC gene product from the cell culture.

The recombinantly expressed *S. avermitilis* AveC gene product is useful for a variety of purposes, including for screening compounds that alter AveC gene product function and thereby modulate avermectin biosynthesis, and for raising antibodies directed against the AveC gene product.

Once an AveC gene product of sufficient purity has been obtained, it can be characterized by standard methods, including by SDS-PAGE, size exclusion chromatography, amino acid sequence analysis, biological activity in producing appropriate products in the avermectin biosynthetic pathway, etc. For example, the amino acid sequence of the AveC gene product can be determined using standard peptide sequencing techniques. The AveC gene product can be further characterized using hydrophilicity analysis (see, e.g., Hopp and Woods, 1981, Proc. Natl. Acad. Sci. USA 78:3824), or analogous software algorithms, to identify hydrophobic and hydrophilic regions of the AveC gene product. Structural analysis can be carried out to identify regions of the AveC gene product that assume specific secondary structures. Biophysical methods such as X-ray crystallography (Engstrom, 1974, Biochem. Exp. Biol. 11: 7-13), computer modelling (Fletterick and Zoller (eds), 1986, in: *Current Communications in Molecular Biology*, Cold Spring Harbor Laboratory, Cold Spring Harbor, N.Y.), and nuclear magnetic resonance (NMR) can be used to map and study sites of interaction between the AveC gene product and its substrate. Information obtained from these studies can be used to select new sites for mutation in the aveC ORF to help develop new strains of *S. avermitilis* having more desirable avermectin production characteristics.

5.3. Construction and Use of AveC Mutants

A primary objective of the present invention is to identify novel mutations in the aveC allele of *S. avermitilis* that result in a change, and most preferably a reduction, in the ratio of B2:B1 avermectins. The present invention thus provides polynucleotide molecules useful to produce novel strains of *S. avermitilis* cells that exhibit a detectable change in avermectin production compared to cells of the same strain but which instead express only the wild-type aveC allele. In a preferred embodiment, such polynucleotide molecules are useful to produce novel strains of *S. avermitilis* cells that produce avermectins in a reduced class 2:1 ratio compared to cells of the same strain which instead express only the wild-type aveC allele. The cells of such strains can also comprise additional mutations to produce an increased amount of avermectins compared to cells of the same strain that instead express only a single wild-type aveC allele.

Mutations to the aveC allele or coding sequence include any mutations that introduce one or more amino acid substitutions, deletions and/or additions into the AveC gene product, or that result in truncation of the AveC gene product, or any combination thereof, and that produce the desired result. Such mutated aveC allele sequences are intended to include any degenerate variants thereof. For example, the present invention provides a polynucleotide molecule comprising the nucleotide sequence of the aveC allele or a degenerate variant thereof, or the AveC gene product-encoding sequence of plasmid pSE186 (ATCC 209604) or a degenerate variant thereof, or the nucleotide sequence of the aveC ORF of *S. avermitilis* as present in FIG. 1 (SEQ ID NO:1) or a degenerate variant thereof, but that further comprises mutations that encode a combination of amino acid substitutions at selected positions in the AveC gene product.

In a non-limiting embodiment, such substitutions occur at one or more amino acid positions of the AveC gene product corresponding to amino acid positions 2, 25, 28, 35, 36, 38, 40, 41, 48, 55, 61, 71, 78, 84, 89, 90, 99, 107, 108, 111, 120, 123, 136, 138, 139, 141, 149, 154, 159, 162, 163, 176, 179, 192, 196, 198, 200, 202, 220, 228, 229, 230, 231, 234, 238, 239, 250, 252, 266, 275, 278, 280, 289 or 298 of SEQ ID NO:2. Preferred combinations of amino acid positions to be substituted comprise one or more of amino acid residues D48, A61, R71, A89, L136, S138, A139, T149, R163, F176, G179, V196, A198, E238 and P289. Specifically preferred combinations of amino acid substitutions comprise substitutions at both D48 and G179, and more specifically D48E and G179S. Specific examples of combinations of amino acid substitutions that result in a reduction in cyclohexyl B:cyclohexyl B1 ratios are listed in FIG. 6A-M.

The present invention thus provides a polynucleotide molecule comprising a nucleotide sequence that is otherwise the same as the *Streptomyces avermitilis* aveC allele, the *S. avermitilis* AveC gene product-encoding sequence of plasmid pSE186 (ATCC 209604) or the nucleotide sequence of the aveC ORF of *S. avermitilis* as presented in FIG. 1 (SEQ ID NO:1), or a degenerate variant thereof, but which nucleotide sequence further comprises mutations encoding a combination of amino acid substitutions at amino acid residues corresponding to the amino acid positions of SEQ ID NO:2, such that cells of *S. avermitilis* strain ATCC 53692 in which the wild-type aveC allele has been inactivated and that express the polynucleotide molecule comprising the mutated nucleotide sequence are capable of producing a class 2:1 ratio of avermectins that is reduced compared to the ratio produced by cells of *S. avermitilis* strain ATCC 53692 that instead express only the wild-type aveC allele, wherein when the class 2:1 avermectins are cyclohexyl B2:cyclohexyl B1 avermectins, the ratio of class 2:1 avermectins is 0.35:1 or less. In a more preferred embodiment, the ratio of cyclohexyl B2:cyclohexyl B1 avermectins is about 0.30:1 or less. In a more preferred embodiment, the ratio of cyclohexyl B2:cyclohexyl B1 avermectins is about 0.25:1 or less. In a more preferred embodiment, the ratio of cyclohexyl B2:cyclohexyl B1 avermectins is about 0.20:1 or less. In a more preferred embodiment, the ratio of cyclohexyl B2:cyclohexyl B1 avermectins is about 0.10:1 or less.

In a particular embodiment thereof, the combination of amino acid substitutions comprises the combination of group (a): D48E, A61T, A89T, S138T, A139T, G179S, A198G, P289L. A non-limiting example of a plasmid encoding these amino acid substitutions is pSE538 (see FIG. 6).

In another particular embodiment thereof, the combination of amino acid substitutions comprises the combination of group (b): G40S, D48E, L136P, G179S, E238D. A non-limiting example of a plasmid encoding these amino acid substitutions is pSE559.

In another particular embodiment thereof, the combination of amino acid substitutions comprises the combination of group (c): D48E, L136P, R163Q, G179S. A non-limiting example of a plasmid encoding these amino acid substitutions is pSE567.

In another particular embodiment thereof, the combination of amino acid substitutions comprises the combination of group (d): D48E, L136P, R163Q, G179S, E238D. Non-limiting examples of plasmids encoding these amino acid substitutions are pSE570 and pSE572.

In another particular embodiment thereof, the combination of amino acid substitutions comprises the combination of group (e): D48E, L136P, R163Q, G179S, A200G, E238D. A non-limiting example of a plasmid encoding these amino acid substitutions is pSE571.

In a particular embodiment thereof, the combination of amino acid substitutions comprises the combination of group (f): D48E, L136P, G179S, E238D. Non-limiting examples of plasmids encoding these amino acid substitutions are pSE501 and pSE546.

In another particular embodiment thereof, the combination of amino acid substitutions comprises the combination of group (g): D48E, A61T, L136P, G179S, E238D. A non-limiting example of a plasmid encoding these amino acid substitutions is pSE510.

In another particular embodiment thereof, the combination of amino acid substitutions comprises the combination of group (h): D48E, A61T, L136P, G179S. A non-limiting example of a plasmid encoding these amino acid substitutions is pSE512.

In another particular embodiment thereof, the combination of amino acid substitutions comprises the combination of group (i): D48E, A89T, S138T, A139T, G179S. A non-limiting example of a plasmid encoding these amino acid substitutions is pSE519.

In another particular embodiment thereof, the combination of amino acid substitutions comprises the combination of group (j): D48E, A61 T, L136P, G179S, A198G, P202S, E238D, P289L. A non-limiting example of a plasmid encoding these amino acid substitutions is pSE526.

In another particular embodiment thereof, the combination of amino acid substitutions comprises the combination of group (k): D48E, A61T, L136P, S138T, A139F, G179S, E238D, P289L. A non-limiting example of a plasmid encoding these amino acid substitutions is pSE528.

In another particular embodiment thereof, the combination of amino acid substitutions comprises the combination of group (l): D48E, L136P, G179S, A198G, E238D, P289L. A non-limiting example of a plasmid encoding these amino acid substitutions is pSE530.

In another particular embodiment thereof, the combination of amino acid substitutions comprises the combination of group (m): D48E, A61T, S138T, A139F, G179S, A198G, P289L. A non-limiting example of a plasmid encoding these amino acid substitutions is pSE531.

In another particular embodiment thereof the combination of amino acid substitutions comprises the combination of group (n): D48E, L84P, G111V, S138T, A139T, G179S, A198G, P289L. A non-limiting example of a plasmid encoding these amino acid substitutions is pSE534.

In another particular embodiment thereof, the combination of amino acid substitutions comprises the combination of group (O): Y28C, D48E, A61T, A89T, S138T, A139T, G179S, E238D. A non-limiting example of a plasmid encoding these amino acid substitutions is pSE535.

In another particular embodiment thereof, the combination of amino acid substitutions comprises the combination of group (p): D48E, A61T, A107T, S108G, L136P, G179S, S192A, E238D, P289L. A non-limiting example of a plasmid encoding these amino acid substitutions is pSE542.

In another particular embodiment thereof, the combination of amino acid substitutions comprises the combination of group (q): D48E, L136P, G179S, R250W. A non-limiting example of a plasmid encoding these amino acid substitutions is pSE545.

In another particular embodiment thereof, the combination of amino acid substitutions comprises the combination of group (r): D48E, A89T, S138T, A139T, R163Q, G179S. A non-limiting example of a plasmid encoding these amino acid substitutions is pSE548.

In another particular embodiment thereof, the combination of amino acid substitutions comprises the combination of group (s): D48E, L136P, G179S, A198G, P289L. A non-limiting example of a plasmid encoding these amino acid substitutions is pSE552.

In another particular embodiment thereof, the combination of amino acid substitutions comprises the combination of group (t): D48E, F78L, A89T, L136P, G179S. A non-limiting example of a plasmid encoding these amino acid substitutions is pSE557.

In another particular embodiment thereof, the combination of amino acid substitutions comprises the combination of group (u): D48E, A89T, S138T, A139T, G179S, E238D, F278L. Non-limiting examples of plasmids encoding these amino acid substitutions are pSE564 and pSE565.

In another particular embodiment thereof, the combination of amino acid substitutions comprises the combination of group (v): D48E, A89T, L136P, R163Q, G179S. A non-limiting example of a plasmid encoding these amino acid substitutions is pSE568.

In another particular embodiment thereof, the combination of amino acid substitutions comprises the combination of group (w): D48E, A61T, A89T, G111V, S138T, A139F, G179S, E238D, P289L. A non-limiting example of a plasmid encoding these amino acid substitutions is pSE543.

In a particular embodiment thereof, the combination of amino acid substitutions comprises the combination of group (x): D25G, D48E, A89T, L136P, S138T, A139T, V141A, I159T, R163Q, G179S. A non-limiting example of a plasmid encoding these amino acid substitutions is pSE504.

In another particular embodiment thereof, the combination of amino acid substitutions comprises the combination of group (y): D48E, A89T, S90G, L136P, R163Q, G179S, E238D. A non-limiting example of a plasmid encoding these amino acid substitutions is pSE508.

In another particular embodiment thereof the combination of amino acid substitutions comprises the combination of group (z): D48E, A61T, A89T, G111V, S138T, A139T, G179S, E238D, P289L. A non-limiting example of a plasmid encoding these amino acid substitutions is pSE511.

In another particular embodiment thereof, the combination of amino acid substitutions comprises the combination of group (aa): D48E, A89T, S138T, A139T, G179S. A non-limiting example of a plasmid encoding these amino acid substitutions is pSE520.

In another particular embodiment thereof, the combination of amino acid substitutions comprises the combination of group (ab): D48E, L136P, R163Q, G179S, S231L. A non-limiting example of a plasmid encoding these amino acid substitutions is pSE523.

In another particular embodiment thereof, the combination of amino acid substitutions comprises the combination of group (ac): D48E, L136P, S138T, A139F, G179S, V196A, E238D. A non-limiting example of a plasmid encoding these amino acid substitutions is pSE527.

In another particular embodiment thereof, the combination of amino acid substitutions comprises the combination of group (ad): D48E, A61T, A89T, F99S, S138T, A139T, G179S, E238D. A non-limiting example of a plasmid encoding these amino acid substitutions is pSE539.

In another particular embodiment thereof, the combination of amino acid substitutions comprises the combination of group (ae): G35S, D48E, A89T, S138T, A139T, G179S, P289L. A non-limiting example of a plasmid encoding these amino acid substitutions is pSE540.

In another particular embodiment thereof, the combination of amino acid substitutions comprises the combination of group (af): D48E, A61T, A89T, S138T, A139T, G179S, V196A, E238D. A non-limiting example of a plasmid encoding these amino acid substitutions is pSE547.

In another particular embodiment thereof, the combination of amino acid substitutions comprises the combination of group (ag): D48E, A89T, G111V, S138T, A139T, G179S, A198G, E238D. A non-limiting example of a plasmid encoding these amino acid substitutions is pSE550.

In another particular embodiment thereof, the combination of amino acid substitutions comprises the combination of group (ah): S41G, D48E, A89T, L136P, G179S. A non-limiting example of a plasmid encoding these amino acid substitutions is pSE558.

In another particular embodiment thereof, the combination of amino acid substitutions comprises the combination of group (ai): D48E, A89T, L136P, R163Q, G179S, P252S. A non-limiting example of a plasmid encoding these amino acid substitutions is pSE563.

In another particular embodiment thereof, the combination of amino acid substitutions comprises the combination of group (aj): D48E, A89T, L136P, G179S, F234S. A non-limiting example of a plasmid encoding these amino acid substitutions is pSE566.

In another particular embodiment thereof, the combination of amino acid substitutions comprises the combination of group (ak): D48E, A89T, L136P, R163Q, G179S, E238D. Non-limiting examples of plasmids encoding these amino acid substitutions are pSE573 and pSE578.

In another particular embodiment thereof, the combination of amino acid substitutions comprises the combination of group (al): Q36R, D48E, A89T, L136P, G179S, E238D. A non-limiting example of a plasmid encoding these amino acid substitutions is pSE574.

In another particular embodiment thereof, the combination of amino acid substitutions comprises the combination of group (am): D48E, A89T, L136P, R163Q, G179S, Non-limiting examples of plasmids encoding these amino acid substitutions are pSE575 and pSE576.

In another particular embodiment, the combination of amino acid substitutions comprises the combination of group (an): D48E, A89T, S138T, G179S. A non-limiting example of a plasmid encoding these amino acid substitutions is pSE577.

In a particular embodiment thereof, the combination of amino acid substitutions comprises the combination of group (ao): D48E, A89T, L136P, G179S, E238D. Non-limiting examples of plasmids encoding these amino acid substitutions are pSE502 and pSE524.

In another particular embodiment thereof, the combination of amino acid substitutions comprises the combination of group (ap): D48E, A89T, L136P, K154E, G179S, E238D. A non-limiting example of a plasmid encoding these amino acid substitutions is pSE503.

In another particular embodiment thereof, the combination of amino acid substitutions comprises the combination of group (aq): D48E, A89T, S138T, A139T, K154R, G179S, V196A, P289L. A non-limiting example of a plasmid encoding these amino acid substitutions is pSE505.

In another particular embodiment thereof, the combination of amino acid substitutions comprises the combination of group (ar): D48E, A89T, S138T, A139F, G179S, V196A, E238D. A non-limiting example of a plasmid encoding these amino acid substitutions is pSE506.

In another particular embodiment thereof, the combination of amino acid substitutions comprises the combination of group (as): D48E, A61T, A89T, L136P, G179S, V196A, A198G, P289L. A non-limiting example of a plasmid encoding these amino acid substitutions is pSE507.

In another particular embodiment thereof, the combination of amino acid substitutions comprises the combination of group (at): D48E, A61T, S138T, A139F, G179S, G196A, E238D, P289L. A non-limiting example of a plasmid encoding these amino acid substitutions is pSE509.

In another particular embodiment thereof, the combination of amino acid substitutions comprises the combination of group (au): D48E, A89T, L136P, G179S, Non-limiting examples of plasmids encoding these amino acid substitutions are pSE514 and pSE525.

In another particular embodiment thereof, the combination of amino acid substitutions comprises the combination of group (av): D48E, A89T, V120A, L136P, G179S. A non-limiting example of a plasmid encoding these amino acid substitutions is pSE515.

In another particular embodiment thereof the combination of amino acid substitutions comprises the combination of group (aw): D48E, A61T, A89T, S138T, A139F, G179S, V196A, A198G, E238D. A non-limiting example of a plasmid encoding these amino acid substitutions is pSE517.

In another particular embodiment thereof, the combination of amino acid substitutions comprises the combination of group (ax): D48E, A61T, A89T, G11V, S138T, A139F, G179S, V196A, E238D. A non-limiting example of a plasmid encoding these amino acid substitutions is pSE518.

In another particular embodiment thereof, the combination of amino acid substitutions comprises the combination of group (ay): D48E, A61T, A89T, S138T, A139T, G179S, V196A, E238D, P289L. Non-limiting examples of plasmids encoding these amino acid substitutions are pSE529 and pSE554.

In another particular embodiment thereof, the combination of amino acid substitutions comprises the combination of group (az): D48E, A61T, A89T, L136P, S138T, A139F, G179S, A198G, E238D. A non-limiting example of a plasmid encoding these amino acid substitutions is pSE532.

In another particular embodiment thereof, the combination of amino acid substitutions comprises the combination of group (ba) D48E, A89T, S138T, A139F, G179S, A198G, V220A. A non-limiting example of a plasmid encoding these amino acid substitutions is pSE536.

In another particular embodiment thereof, the combination of amino acid substitutions comprises the combination of group (bb): D48E, A61T, A89T, S138T, A139T, G179S, V196A, E238D, R239H, P289L. A non-limiting example of a plasmid encoding these amino acid substitutions is pSE537.

In another particular embodiment thereof, the combination of amino acid substitutions comprises the combination of group (bc): D48E, A61T, A89T, L136P, G179S, P289L. A non-limiting example of a plasmid encoding these amino acid substitutions is pSE541.

In another particular embodiment thereof, the combination of amino acid substitutions comprises the combination of group (bd): D4BE, A89T, S138T, A139T, G179S, V196A, E238D, P289L. Non-limiting examples of plasmids encoding these amino acid substitutions are pSE549 and pSE553.

In another particular embodiment thereof, the combination of amino acid substitutions comprises the combination of group (be): D48E, A61T, A89T, S138T, A139F, G179S, V196A, E238D. A non-limiting example of a plasmid encoding these amino acid substitutions is pSE551.

In another particular embodiment thereof the combination of amino acid substitutions comprises the combination of groups (da) through (dl): FIG. 6L. A non-limiting example of a plasmid encoding these amino acid substitutions is PSE601.

In another particular embodiment thereof, the combination of amino acid substitutions comprises the combination of groups (ea) through (es): FIG. 6M. A non-limiting example of a plasmid encoding these amino acid substitutions is pSE617.

The present invention further provides a polynucleotide molecule comprising a nucleotide sequence that is otherwise the same as the *Streptomyces avermitilis* aveC allele, the *S. avermitilis* AveC gene product-encoding sequence of plasmid pSE186 (ATCC 209604) or the nucleotide sequence of the aveC ORF of *S. avermitilis* as presented in FIG. 1 (SEQ ID NO:1), or a degenerate variant thereof, but which nucleotide sequence further comprises mutations encoding a combination of amino acid substitutions at amino acid residues corresponding to the amino acid positions of SEQ ID NO:2, such that cells of *S. avermitilis* strain ATCC 53692 in which the wild-type aveC allele has been inactivated and that express a polynucleotide molecule comprising the mutated nucleotide sequence are capable of producing a class 2:1 ratio of avermectins that is reduced compared to the ratio produced by cells of *S. avermitilis* strain ATCC 53692 that instead express only the wild-type aveC allele, wherein when the class 2:1 avermectins are cyclohexyl B2:cyclohexyl B1 avermectins, the ratio of class 2:1 avermectins is reduced to about 0.40:1 or less, and wherein the combination of amino acid substitutions comprises a combination selected from the group consisting of:

(bf) D48E, S138T, A139T, G179S, E238D; and
(bg) Y28C, Q38R, D48E, L136P, G179S, E238D.

Non-limiting examples of a plasmid encoding the amino acid substitutions of group (bf) are pSE556 and pSE569. A non-limiting example of a plasmid encoding the amino acid substitutions of group (bg) is pSE561.

In another particular embodiment thereof, the combination of amino acid substitutions comprises the combination of groups (ca) through (cs): FIG. 6K. A non-limiting example of a plasmid encoding these amino acid substitutions is pSE582.

The present invention contemplates that any of the aforementioned amino acid substitutions can be accomplished by any modification to the nucleotide sequence of the aveC allele or a degenerate variant thereof that results in such substitutions. For example, it is possible to effect most of the amino acid substitutions described herein by changing a native codon sequence or a degenerate variant thereof to any one of several alternative codons that encode the same amino acid substitution. The various possible sequences that can encode the aforementioned amino acid substitutions will be readily apparent to a person of skill in the art in view of the present disclosure and the known degeneracy of the genetic code. In a non-limiting embodiment for each particular combination recited above, the amino acid substitutions are achieved by the non-silent nucleotide changes set forth in FIG. 6.

As used herein, the phrase "the combination of amino acid substitutions comprises the combination of group . . . ", and the like, means that the amino acid substitutions in the AveC gene product according to the present invention include at least those substitutions that are specifically recited, and may include other amino acid substitutions, or amino acid deletions, or amino acid additions, or some combination thereof, wherein the expression of the resulting AveC gene product in the *S. avermitilis* cell yields a desirable reduction in the ratio of B2:B1 avermectins.

Mutations to the aveC allele or degenerate variant thereof can be carried out by any of a variety of known methods, including by use of error-prone PCR, or by cassette mutagenesis. For example, oligonucleotide-directed mutagenesis can be employed to alter the sequence of the aveC allele or ORF in a defined way such as, e.g., to introduce one or more restriction sites, or a termination codon, into specific regions within the aveC allele or ORF. Methods such as those described in U.S. Pat. No. 5,605,793, U.S. Pat. No. 5,830,721 and U.S. Pat. No. 5,837,458, which involve random fragmentation, repeated cycles of mutagenesis, and nucleotide shuffling, can also be used to generate large libraries of polynucleotides having nucleotide sequences encoding aveC mutations.

Targeted mutations can be useful, particularly where they serve to alter one or more conserved amino acid residues in the AveC gene product. For example, a comparison of the deduced amino acid sequence of the AveC gene product of *S. avermitilis* (SEQ ID NO:2) with AveC homolog gene products from *S. griseochromogenes* (SEQ ID NO:5) and *S. hygroscopicus* (SEQ ID NO:4), as described in U.S. Pat. No. 6,248,579, indicates sites of significant conservation of amino acid residues between these species. Targeted mutagenesis that leads to a change in one or more of these conserved amino acid residues may be effective in producing novel mutant strains that exhibit desirable alterations in avermectin production.

Random mutagenesis can also be useful, and can be carried out by exposing cells of *S. avermitilis* to ultraviolet radiation or x-rays, or to chemical mutagens such as N-methyl-N'-nitrosoguanidine, ethyl methane sulfonate, nitrous acid or nitrogen mustards. See, e.g., Ausubel, 1989, above, for a review of mutagenesis techniques.

Once mutated polynucleotide molecules are generated, they are screened to determine whether they can modulate avermectin biosynthesis in *S. avermitilis*. In a preferred embodiment, a polynucleotide molecule having a mutated nucleotide sequence is tested by complementing a strain of *S. avermitilis* in which the aveC gene has been inactivated to give an aveC negative (aveC) background. In a non-limiting method, the mutated polynucleotide molecule is spliced into an expression plasmid in operative association with one or more regulatory elements, which plasmid also preferably comprises one or more drug resistance genes to allow for selection of transformed cells. This vector is then transformed into aveC host cells using known techniques, and transformed cells are selected and cultured in appropriate fermentation media under conditions that permit or induce avermectin production, for example, by including appropriate starter subunits in the medium, and culturing under optimal conditions for avermectin production as known in the art. Fermentation products are then analyzed by HPLC to determine the ability of the mutated polynucleotide molecule to complement the host cell. Several plasmid vectors bearing mutated polynucleotide molecules capable of reducing the B2:B1 ratio of avermectins, including pSE188, pSE199, pSE231, pSE239, and pSE290 through pSE297, are exemplified in Section 8.3, below. Other examples of such plasmid vectors are recited in FIG. 6.

Any of the aforementioned methods of the present invention can be carried out using fermentation culture media preferably supplemented with cyclohexane carboxylic acid, although other appropriate fatty acid precursors, such as any one of the fatty acid precursors listed in TABLE 1, or methylthiolactic acid, can also used.

Once a mutated polynucleotide molecule that modulates avermectin production in a desirable direction has been identified, the location of the mutation in the nucleotide sequence can be determined. For example, a polynucleotide molecule having a nucleotide sequence encoding a mutated AveC gene product can be isolated by PCR and subjected to DNA sequence analysis using known methods. By comparing the DNA sequence of the mutated aveC allele to that of the wild-type aveC allele, the mutation(s) responsible for the alteration in avermectin production can be determined. For example, S. avermitilis AveC gene products comprising either single amino acid substitutions at any of residues 55 (S55F), 138 (S138T), 139 (A139T), or 230 (G230D), or double substitutions at positions 138 (S138T) and 139 (A139T or A139F), yielded changes in AveC gene product function such that the ratio of class 2:1 avermectins produced was altered (see Section 8, below), wherein the recited amino acid positions correspond to those presented in FIG. 1 (SEQ ID NO:2). In addition, the following seven combinations of mutations have each been shown to effectively reduce the class 2:1 ratio of avermectins: (1) D48E/A89T; (2) S138T/A139T/G179S; (3) Q38P/L136P/E238D; (4) F99S/S138T/A139T/G179S; (5) A139T/M228T; (6) G111V/P289L; (7) A139T/K154E/Q298H; (8) D48E/A61T/R71 L/A89T/L136P/T149S/F176C/G179S/N196A/E238D/I280V. The present invention provides one hundred eight (108) additional combinations of mutations that are shown to reduce the cyclohexyl B2:cyclohexyl B1 ratio of avermectins, and these are presented in FIG. 6 and recited in the appended claims.

As used herein, the aforementioned designations, such as A139T, indicate the original amino acid residue by single letter designation, which in this example is alanine (A), at the indicated position, which in this example is position 139 (referring to SEQ ID NO:2) of the polypeptide, followed by the amino acid residue which replaces the original amino acid residue, which in this example is threonine (T).

As used herein, where an amino acid residue encoded by an aveC allele in the S. avermitilis chromosome, or in a vector or isolated polynucleotide molecule of the present invention is referred to as "corresponding to" a particular amino acid residue of SEQ ID NO:2, or where an amino acid substitution is referred to as occurring at a particular position "corresponding to" that of a specific numbered amino acid residue of SEQ ID NO:2, this is intended to refer to the amino acid residue at the same relative location in the AveC gene product, which the skilled artisan can quickly determine by reference to the amino acid sequence presented herein as SEQ ID NO:2.

As used herein, where specific mutations in the aveC allele encoding particular mutations are recited as base changes at specific nucleotide positions in the aveC allele "corresponding to" particular nucleotide positions as shown in SEQ ID NO:1, or where a nucleotide position in the aveC allele is otherwise referred to as "corresponding to" a particular nucleotide position in SEQ ID NO:1, this is intended to refer to the nucleotide at the same relative location in the aveC nucleotide sequence or a degenerate variant thereof which the skilled artisan can quickly determine by reference to the nucleotide sequence presented herein as SEQ ID NO:1.

As used herein to refer to ratios of cyclohexyl B2:cyclohexyl B1 avermectins, the term "about" refers to the specifically stated numerical value plus or minus 10% of that stated value.

A polynucleotide molecule of the present invention may be "isolated", which means either that it is: (i) purified to the extent that it is substantially free of other polynucleotide molecules having different nucleotide sequences, or (ii) present in an environment in which it would not naturally occur, e.g., where an aveC allele from S. avermitilis, or a mutated version thereof, is present in a cell other than a cell of S. avermitilis, or (iii) present in a form in which it would not naturally occur, e.g., as a shorter piece of DNA, such as a restriction fragment digested out of a bacterial chromosome, comprising predominantly the aveC coding region or a mutated version thereof, with or without any associated regulatory sequences thereof, or as subsequently integrated into a heterologous piece of DNA, such as the chromosome of a bacterial cell (other than a cell of S. avermitilis) or the DNA of a vector such as a plasmid or phage, or integrated into the S. avermitilis chromosome at a locus other than that of the native aveC allele.

The present invention further provides a recombinant vector comprising a polynucleotide molecule of the present invention. Such a recombinant vector can be used to target any of the polynucleotide molecules comprising mutated nucleotide sequences of the present invention to the site of the aveC allele of the S. avermitilis chromosome to either insert into or replace the aveC ORF or a portion thereof, e.g., by homologous recombination. According to the present invention, however, a polynucleotide molecule comprising a mutated nucleotide sequence of the present invention provided herewith can also function to modulate avermectin biosynthesis when inserted into the S. avermitilis chromosome at a site other than at the aveC allele, or when maintained episomally in S. avermitilis cells. Thus, the present invention further provides vectors comprising a polynucleotide molecule comprising a mutated nucleotide sequence of the present invention, which vectors can be used to insert the polynucleotide molecule at a site in the S. avermitilis chromosome other than at the aveC gene, or to be maintained episomally.

In a non-limiting embodiment, the vector is a gene replacement vector that can be used to insert a mutated aveC allele or degenerate variant thereof according to the present invention into cells of a strain of S. avermitilis, thereby generating novel strains of S. avermitilis, the cells of which can produce avermectins in a reduced class 2:1 ratio compared to cells of the same strain which instead express only the wild-type aveC allele. Such gene replacement vectors can be constructed using mutated polynucleotide molecules present in expression vectors provided herewith, such as those expression vectors exemplified in Section 8 below.

The present invention further provides vectors that can be used to insert a mutated aveC allele or degenerate variant thereof into cells of a strain of S. avermitilis to generate novel strains of cells that produce altered amounts of avermectins compared to cells of the same strain which instead express only the wild-type aveC allele. In a preferred embodiment, the amount of avermectins produced by the cells is increased. In a specific though non-limiting embodiment, such a vector comprises a strong promoter as known in the art, such as, e.g., the strong constitutive ermE promoter from Saccharopolyspora erythraea, that is situated upstream from, and in operative association with, the aveC ORF. Such vectors can be constructed using the mutated aveC allele of plasmid pSE189, and according to methods described in U.S. Pat. No. 6,248,579.

Figure 3:
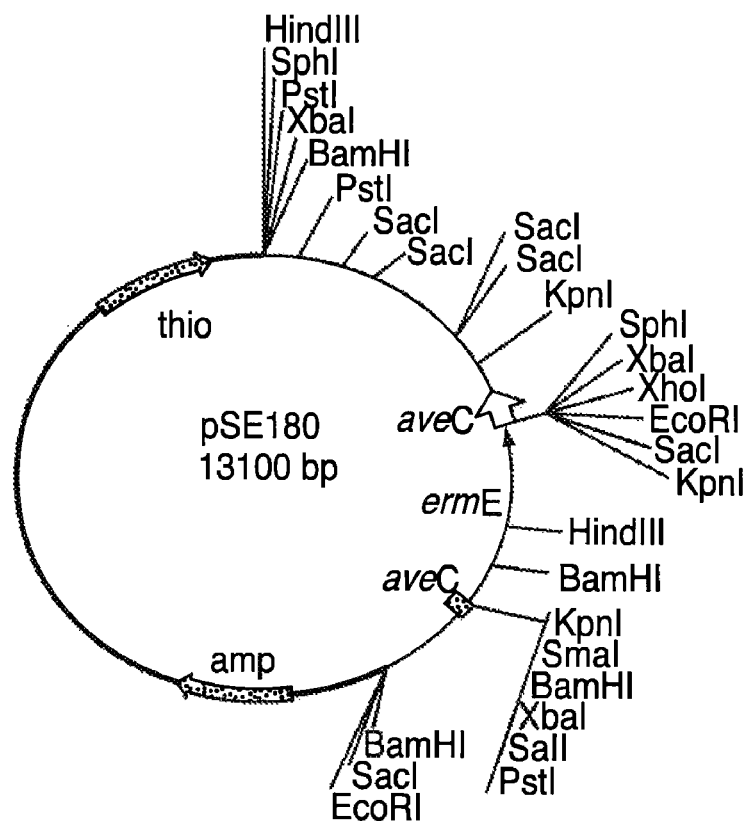
FIG. 3. Gene replacement vector pSE180 (ATCC 209605) comprising the ermE gene of *Sacc. erythraea* inserted into the aveC ORF of *S. avermitilis*.

The present invention provides gene replacement vectors that are useful to inactivate the aveC gene in a wild-type strain of S. avermitilis. In a non-limiting embodiment, such gene replacement vectors can be constructed using the mutated polynucleotide molecule present in plasmid pSE180 (ATCC 209605), which is exemplified in Section 8.1, below (FIG. 3). The present invention further provides gene replacement vectors that comprise a polynucleotide molecule comprising or consisting of nucleotide sequences that naturally flank the aveC gene in situ in the S. avermitilis chromosome, including, e.g., those flanking nucleotide sequences shown in FIG. 1 (SEQ ID NO:1), which vectors can be used to delete the S. avermitilis aveC ORF.

The present invention further provides a host cell comprising a polynucleotide molecule or recombinant vector of the present invention. The host cell can be any prokaryotic or eukaryotic cell capable of use as a host for the polynucleotide molecule or recombinant vector. In a preferred embodiment, the host cell is a bacterial cell. In a more preferred embodiment, the host cell is a Streptomyces cell. In a more preferred embodiment, the host cell is a cell of Streptomyces avermitilis.

The present invention further provides a method for making a novel strain of Streptomyces avermitilis, comprising (i) mutating the aveC allele in a cell of a strain of S. avermitilis, which mutation results in a combination of amino acid substitutions in the AveC gene product, or (ii) introducing into a cell of a strain of S. avermitilis a mutated aveC allele or degenerate variant thereof encoding an AveC gene product comprising a combination of amino acid substitutions, wherein the combination of amino acid substitutions is selected from (a) through (es) listed above.

The present invention further provides a method for making a novel strain of S. avermitilis, comprising (i) mutating the aveC allele in a cell of a strain of S. avermitilis, which mutation results in a combination of amino acid substitutions in the AveC gene product, or (ii) introducing into a cell of a strain of S. avermitilis a mutated aveC allele or degenerate variant thereof encoding an AveC gene product comprising a combination of amino acid substitutions, wherein cells comprising the mutated aveC allele or degenerate variant are capable of producing cyclohexyl B2:cyclohexyl B1 avermectins in a ratio of 0.35:1 or less. In a non-limiting embodiment thereof the mutated aveC allele or degenerate variant thereof encodes an AveC gene product comprising a combination of amino acid substitutions selected from the group consisting of (a) through (be) and (da) through (es) listed above.

In a preferred embodiment thereof, the ratio of cyclohexyl B2:cyclohexyl B1 avermectins is about 0.30:1 or less. In a non-limiting embodiment thereof, the mutated aveC allele or degenerate variant thereof encodes an AveC gene product comprising a combination of amino acid substitutions selected from the group consisting of (f) through (be) and (da) through (es) listed above.

In a more preferred embodiment thereof, the ratio of cyclohexyl B2:cyclohexyl B1 avermectins is about 0.25:1 or less. In a non-limiting embodiment thereof, the mutated aveC allele or degenerate variant thereof encodes an AveC gene product comprising a combination of amino acid substitutions selected from the group consisting of (w) through (be) and (da) through (es) listed above.

In a more preferred embodiment thereof, the ratio of cyclohexyl B2:cyclohexyl B1 avermectins is about 0.20:1 or less. In a non-limiting embodiment thereof, the mutated aveC allele or degenerate variant thereof encodes an AveC gene product comprising a combination of amino acid substitutions selected from the group consisting of (ao) through (be) and (da) through (es) listed above.

In a more preferred embodiment thereof, the ratio of cyclohexyl B2:cyclohexyl B1 avermectins is about 0.10:1 or less. In a non-limiting embodiment thereof, the mutated aveC allele or degenerate variant thereof encodes an AveC gene product comprising a combination of amino acid substitutions selected from the group consisting of (ea) through (es) listed above.

The present invention further provides a method for making a novel strain of Streptomyces avermitilis, comprising (i) mutating the aveC allele in a cell of a strain of S. avermitilis, which mutation results in a combination of amino acid substitutions in the AveC gene product, or (ii) introducing into a cell of a strain of S. avermitilis a mutated aveC allele or degenerate variant thereof encoding an AveC gene product comprising a combination of amino acid substitutions, wherein the combination of amino acid substitutions is selected from the group consisting of (bf) and (bg). In a preferred embodiment thereof, cells of S. avermitilis comprising such a mutated aveC allele or degenerate variant are capable of producing cyclohexyl B2:cyclohexyl B1 avermectins in a ratio of about 0.40:1 or less.

By so mutating the aveC allele, or by so introducing a mutated aveC allele or degenerate variant thereof, according to the above-recited steps, a new strain of S avermitilis is made.

The present invention further provides a cell of a Streptomyces species that comprises a mutated aveC allele or degenerate variant thereof encoding an AveC gene product comprising a combination of amino acid substitutions selected from (a) through (es) listed above. In a preferred embodiment thereof, the species of Streptomyces is S. avermitilis.

The present invention further provides a cell of S. avermitilis capable of producing cyclohexyl B2:cyclohexyl B1 avermectins in a ratio of 0.35:1 or less. In a non-limiting embodiment thereof, the cell comprises a mutated aveC allele or degenerate variant thereof encoding an AveC gene product comprising a combination of amino acid substitutions selected from the group consisting of (a) through (be) and (da) through (es) listed above.

In a preferred embodiment thereof, the ratio of cyclohexyl B2:cyclohexyl B1 avermectins is about 0.30:1 or less. In a non-limiting embodiment thereof, the cell comprises a mutated aveC allele or degenerate variant thereof encoding an AveC gene product comprising a combination of amino acid substitutions selected from the group consisting of (f) through (be) and (da) through (es) listed above.

In a more preferred embodiment thereof, the ratio of cyclohexyl B2:cyclohexyl B1 avermectins is about 0.25:1 or less. In a non-limiting embodiment thereof, the cell comprises a mutated aveC allele or degenerate variant thereof encoding an AveC gene product comprising a combination of amino acid substitutions selected from the group consisting of (w) through (be) and (da) through (es) listed above.

In a more preferred embodiment thereof, the ratio of cyclohexyl B2:cyclohexyl B1 avermectins is about 0.20:1 or less. In a non-limiting embodiment thereof, the cell comprises a mutated aveC allele or degenerate variant thereof encoding an AveC gene product comprising a combination of amino acid substitutions selected from the group consisting of (ao) through (be) and (da) through (es) listed above.

In a more preferred embodiment thereof, the ratio of cyclohexyl B2:cyclohexyl B1 avermectins is about 0.10:1 or less. In a non-limiting embodiment thereof, the cell comprises a mutated aveC allele or degenerate variant thereof encoding an AveC gene product comprising a combination of amino acid substitutions selected from the group consisting of (ea) through (es) listed above.

The present invention further provides a cell of a *Streptomyces* species, comprising a mutated aveC allele or degenerate variant thereof encoding an AveC gene product comprising a combination of amino acid substitutions selected from the group consisting of (bf) and (bg) listed above. In a preferred embodiment thereof, the species of *Streptomyces* is *S. avermitilis*. In a more preferred embodiment thereof, the cell is a cell of *S. avermitilis* capable of producing cyclohexyl B2:cyclohexyl B1 avermectins in a ratio of about 0.40:1 or less.

Although any of the recited mutations can be present in cells of the present invention on an extrachromosomal element such as a plasmid, it is preferred that such mutations are present in an aveC coding sequence integrated into the *S. avermitilis* chromosome, and preferably, though not necessarily, at the site of the native aveC allele.

Such novel strains of cells are useful in the large-scale production of commercially desirable avermectins such as doramectin.

The present invention further provides a process for producing avermectins, comprising culturing the *S. avermitilis* cells of the present invention in culture media under conditions that permit or induce the production of avermectins therefrom, and recovering said avermectins from the culture. In a preferred embodiment, the cells used in the process produce cyclohexyl B2:cyclohexyl B1 avermectins in a ratio of 0.35:1 or less, more preferably in a ratio of about 0.30:1 or less, more preferably in a ratio of about 0.25:1 or less, more preferably in a ratio of about 0.20:1 or less, and more preferably in a ratio of about 0.10 or less.

In a preferred embodiment thereof, cells producing cyclohexyl B2:cyclohexyl B1 avermectins in a ratio of 0.35:1 or less comprise a mutated aveC allele or degenerate variant thereof encoding an AveC gene product comprising a combination of amino acid substitutions selected from the group consisting of (a) through (be) and (da) through (es) listed above.

In a further preferred embodiment thereof, cells producing cyclohexyl B2:cyclohexyl B1 avermectins in a ratio of about 0.30:1 or less comprise a mutated aveC allele or degenerate variant thereof encoding an AveC gene product comprising a combination of amino acid substitutions selected from the group consisting of (f) through (be) and (da) through (es) listed above.

In a further preferred embodiment thereof, cells producing cyclohexyl B2:cyclohexyl B1 avermectins in a ratio of about 0.25:1 or less comprise a mutated aveC allele or degenerate variant thereof encoding an AveC gene product comprising a combination of amino acid substitutions selected from the group consisting of (w) through (be) and (da) through (es) listed above.

In a further preferred embodiment thereof, cells producing cyclohexyl B2:cyclohexyl B1 avermectins in a ratio of about 0.20:1 or less comprise a mutated aveC allele or degenerate variant thereof encoding an AveC gene product comprising a combination of amino acid substitutions selected from the group consisting of (ao) through (be) and (da) through (es) listed above.

In a further preferred embodiment thereof, cells producing cyclohexyl B2:cyclohexyl B1 avermectins in a ratio of about 0.10:1 or less comprise a mutated aveC allele or degenerate variant thereof encoding an AveC gene product comprising a combination of amino acid substitutions selected from the group consisting of (ea) through (es) listed above.

In another embodiment, the cells produce cyclohexyl B2:cyclohexyl B1 avermectins in a ratio of about 0.40:1 or less and comprise a mutated aveC allele or degenerate variant thereof encoding an AveC gene product comprising a combination of amino acid substitutions selected from the group consisting of (bf) and (bg) listed above.

The process of the invention provides increased efficiency in the production of commercially valuable avermectins such as doramectin.

The present invention further provides a composition of cyclohexyl B2:cyclohexyl B1 avermectins produced by cells of *Streptomyces avermitilis*, comprising the cyclohexyl B2:cyclohexyl B1 avermectins present in a culture medium in which the cells have been cultured, wherein the ratio of the cyclohexyl B2:cyclohexyl B1 avermectins present in the culture medium is 0.35:1 or less, preferably about 0.30:1 or less, more preferably about 0.25:1 or less, more preferably about 0.20:1 or less, and more preferably about 0.10 and less. In a particular embodiment, the composition of cyclohexyl B2:cyclohexyl B1 avermectins is produced by cells of a strain of *S. avermitilis* that express a mutated aveC allele or degenerate variant thereof which encodes a gene product that results in the reduction in the ratio of cyclohexyl B2:cyclohexyl B1 avermectins produced by the cells compared to cells of the same strain of *S. avermitilis* that do not express the mutated aveC allele but instead express only the wild-type aveC allele.

In a preferred embodiment thereof, where the composition is cyclohexyl B2:cyclohexyl B1 avermectins in a ratio of 0.35:1 or less, the composition is produced by cells comprising a mutated aveC allele or degenerate variant thereof encoding an AveC gene product comprising a combination of amino acid substitutions selected from the group consisting of (a) through (be) and (da) through (es) listed above.

In a further preferred embodiment thereof, where the composition is cyclohexyl B2:cyclohexyl B1 avermectins in a ratio of about 0.30:1 or less, the composition is produced by cells comprising a mutated aveC allele or degenerate variant thereof encoding an AveC gene product comprising a combination of amino acid substitutions selected from the group consisting of (f) through (be) and (da) through (es) listed above.

In a further preferred embodiment thereof, where the composition is cyclohexyl B2:cyclohexyl B1 avermectins in a ratio of about 0.25:1 or less, the composition is produced by cells comprising a mutated aveC allele or degenerate variant thereof encoding an AveC gene product comprising a combination of amino acid substitutions selected from the group consisting of (w) through (be) and (da) through (es) listed above.

In a further preferred embodiment thereof, where the composition is cyclohexyl B2:cyclohexyl B1 avermectins in a ratio of about 0.20:1 or less, the composition is produced by cells comprising a mutated aveC allele or degenerate variant thereof encoding an AveC gene product comprising a combination of amino acid substitutions selected from the group consisting of (so) through (be) and (da) through (es) listed above.

In a further preferred embodiment thereof, where the composition is cyclohexyl B2:cyclohexyl B1 avermectins in a ratio of about 0.10:1 or less, the composition is produced by cells comprising a mutated aveC allele or degenerate variant thereof encoding an AveC gene product comprising a combination of amino acid substitutions selected from the group consisting of (ea) through (es) listed above.

The present invention further provides a composition of cyclohexyl B2:cyclohexyl B1 avermectins produced by cells of *Streptomyces avermitilis*, comprising the cyclohexyl B2:cyclohexyl B1 avermectins present in a culture medium in which the cells have been cultured, wherein the ratio of the cyclohexyl B2:cyclohexyl B1 avermectins present in the culture medium is about 0.40:1 or less, and which is produced by cells comprising a mutated aveC allele or degenerate variant thereof encoding an AveC gene product comprising a combination of amino acid substitutions selected from the group consisting of (bf) and (bg) listed above.

Although it is preferred that the novel avermectin composition is present in a culture medium in which the cells have been cultured, e.g., in partially or totally exhausted fermentation culture fluid, the avermectin composition may alternatively be partially or substantially purified from the culture fluid by known biochemical techniques of purification, such as by ammonium sulfate precipitation, dialysis, size fractionation, ion exchange chromatography, HPLC, etc.

In addition to making novel strains of *S. avermitilis* comprising cells that are capable of producing reduced ratios of cyclohexyl B2:cyclohexyl B1 as described above, the present invention contemplates that additional mutations can be incorporated into cells of *S. avermitilis* to further improve characteristics of avermectin production. In a non-limiting embodiment, cells of the present invention can further comprise modifications to increase the production level of avermectins. In one embodiment, such cells can be prepared by (i) mutating the aveC allele in a cell of *S. avermitilis*, or (ii) introducing a mutated aveC allele or degenerate variant thereof into cells of a strain of *S. avermitilis*, wherein the expression of the mutated allele results in an increase in the amount of avermectins produced by cells of a strain of *S. avermitilis* expressing the mutated aveC allele compared to cells of the same strain that instead express only a single wild-type aveC allele, and selecting transformed cells that produce avermectins in an increased amount compared to the amount of avermectins produced by cells of the strain that instead express only the single wild-type aveC allele. For example, the aveC allele can be modified so that it comprises a strong promoter, such as the strong constitutive ermE promoter from *Saccharopolyspora erythraea*, inserted upstream from and in operative association with the aveC ORF. In another embodiment, one or more mutations can be introduced into the aveR1 and/or aveR2 genes of *S. avermitilis*, thereby increasing the level of avermectin production as described in U.S. Pat. No. 6,197,591 to Stutzman-Engwall et al., issued Mar. 6, 2001.

5.4. Uses of Avermectins

Avermectins are highly active antiparasitic agents having particular utility as anthelmintics, ectoparasiticides, insecticides and acaricides. Avermectin compounds produced according to the methods of the present invention are useful for any of these purposes. For example, avermectin compounds produced according to the present invention are useful to treat various diseases or conditions in humans, particularly where those diseases or conditions are caused by parasitic infections, as known in the art. See, e.g., Ikeda and Omura, 1997, Chem. Rev. 97(7):2591-2609. More particularly, avermectin compounds produced according to the present invention are effective in treating a variety of diseases or conditions caused by endoparasites, such as parasitic nematodes, which can infect humans, domestic animals, swine, sheep, poultry, horses or cattle.

More specifically, avermectin compounds produced according to the present invention are effective against nematodes that infect humans, as well as those that infect various species of animals. Such nematodes include gastrointestinal parasites such as *Ancylostoma, Necator, Ascaris, Strongyloides, Trichinella, Capillaria, Trichuris, Enterobius, Diroflaria*, and parasites that are found in the blood or other tissues or organs, such as filarial worms and the extract intestinal states of *Strongyloides* and *Trichinella*.

The avermectin compounds produced according to the present invention are also useful in treating ectoparasitic infections including, e.g., arthropod infestations of mammals and birds, caused by ticks, mites, lice, fleas, blowflies, biting insects, or migrating dipterous larvae that can affect cattle and horses, among others.

The avermectin compounds produced according to the present invention are also useful as insecticides against household pests such as, e.g., the cockroach, clothes moth, carpet beetle and the housefly among others, as well as insect pests of stored grain and of agricultural plants, which pests include spider mites, aphids, caterpillars, and orthopterans such as locusts, among others.

Animals that can be treated with the avermectin compounds produced according to the present invention include sheep, cattle, horses, deer, goats, swine, birds including poultry, and dogs and cats.

An avermectin compound produced according to the present invention is administered in a formulation appropriate to the specific intended use, the particular species of host animal being treated, and the parasite or insect involved. For use as a parasiticide, an avermectin compound produced according to the present invention can be administered orally in the form of a capsule, bolus, tablet or liquid drench or, alternatively, can be administered as a pour-on, or by injection, or as an implant. Such formulations are prepared in a conventional manner in accordance with standard veterinary practice. Thus, capsules, boluses or tablets can be prepared by mixing the active ingredient with a suitable finely divided diluent or carrier additionally containing a disintegrating agent and/or binder such as starch, lactose, talc, magnesium stearate, etc. A drench formulation can be prepared by dispersing the active ingredient in an aqueous solution together with a dispersing or wetting agent, etc. Injectable formulations can be prepared in the form of a sterile solution, which can contain other substances such as, e.g., sufficient salts and/or glucose to make the solution isotonic with blood.

Such formulations will vary with regard to the weight of active compound depending on the patient, or species of host animal to be treated, the severity and type of infection, and the body weight of the host. Generally, for oral administration a dose of active compound of from about 0.001 to 10 mg per kg of patient or animal body weight given as a single dose or in divided doses for a period of from 1 to 5 days will be satisfactory. However, there can be instances where higher or lower dosage ranges are indicated, as determined, e.g., by a physician or veterinarian, as based on clinical symptoms.

As an alternative, an avermectin compound produced according to the present invention can be administered in combination with animal feedstuff, and for this purpose a concentrated feed additive or premix can be prepared for mixing with the normal animal feed.

For use as an insecticide, and for treating agricultural pests, an avermectin compound produced according to the present invention can be applied as a spray, dust, emulsion and the like in accordance with standard agricultural practice.

6. Example

Fermentation of *Streptomyces*

Avermitilis and B2:B1 Avermectin Analysis

Strains lacking both branched-chain 2-oxo acid dehydrogenase and 5-O-methyltransferase activities produce no avermectins if the fermentation medium is not supplemented with fatty acids. This example demonstrates that in such mutants a wide range of B2:B1 ratios of avermectins can be obtained when biosynthesis is initiated in the presence of different fatty acids.

6.1. Materials And Methods

*Streptomyces avermitilis* ATCC 53692 was stored at −70° C. as a whole broth prepared in seed medium consisting of: Starch (Nadex, Laing National)-20 g; Pharmamedia (Trader's Protein, Memphis, Tenn.)-15 g; Ardamine pH (Yeast Products Inc.)-5 g; calcium carbonate—1 g. Final volume was adjusted to 1 liter with tap water, pH was adjusted to 7.2, and the medium was autoclaved at 121° C. for 25 min.

Two ml of a thawed suspension of the above preparation was used to inoculate a flask containing 50 ml of the same medium. After 48 hrs incubation at 28° C. on a rotary shaker at 180 rpm, 2 ml of the broth was used to inoculate a flask containing 50 ml of a production medium consisting of: Starch—80 g; calcium carbonate—7 g; Pharmamedia—5 g; dipotassium hydrogen phosphate—1 g; magnesium sulfate—1 g; glutamic acid—0.6 g; ferrous sulfate heptahydrate—0.01 g; zinc sulfate—0.001 g; manganous sulfate—0.001 g. Final volume was adjusted to 1 liter with tap water, pH was adjusted to 7.2, and the medium was autoclaved at 121° C. for 25 min.

Various carboxylic acid substrates (see TABLE 1) were dissolved in methanol and added to the fermentation broth 24 hrs after inoculation to give a final concentration of 0.2 g/liter. The fermentation broth was incubated for 14 days at 28° C., then the broth was centrifuged (2,500 rpm for 2 min) and the supernatant discarded. The mycelial pellet was extracted with acetone (15 ml), then with dichloromethane (30 ml), and the organic phase separated, filtered, then evaporated to dryness. The residue was taken up in methanol (1 ml) and analyzed by HPLC with a Hewlett-Packard 1090A liquid chromatograph equipped with a scanning diode-array detector set at 240 nm. The column used was a Beckman Ultrasphere C-18, 5 μm, 4.6 mm×25 cm column maintained at 40° C. Twenty-five μl of the above methanol solution was injected onto the column. Elution was performed with a linear gradient of methanol-water from 80:20 to 95:5 over 40 min at 0.85/ml min. Two standard concentrations of cyclohexyl B1 were used to calibrate the detector response, and the area under the curves for B2 and B1 avermectins was measured.

6.2. Results

The HPLC retention times observed for the B2 and B1 avermectins, and the 2:1 ratios, are shown in TABLE 1.

TABLE 1

| Substrate | HPLC Retention Time (min) | | Ratio |
| | B2 | B1 | B2:B1 |
| --- | --- | --- | --- |
| 4-Tetrahydropyran carboxylic acid | 8.1 | 14.5 | 0.25 |
| Isobutyric acid | 10.8 | 18.9 | 0.5 |
| 3-Furoic acid | 7.6 | 14.6 | 0.62 |
| S-(+)-2-methylbutyric acid | 12.8 | 21.6 | 1.0 |
| Cyclohexanecarboxylic acid | 16.9 | 26.0 | 1.6 |
| 3-Thiophenecarboxylic acid | 8.8 | 16.0 | 1.8 |
| Cyclopentanecarboxylic acid | 14.2 | 23.0 | 2.0 |
| 3-Trifluoromethylbutyric acid | 10.9 | 18.8 | 3.9 |
| 2-Methylpentanoic acid | 14.5 | 24.9 | 4.2 |
| Cycloheptanecarboxylic acid | 18.6 | 29.0 | 15.0 |

The data presented in TABLE 1 demonstrates an extremely wide range of B2:B1 avermectin product ratios, indicating a considerable difference in the results of dehydrative conversion of class 2 compounds to class 1 compounds, depending on the nature of the fatty acid side chain starter unit supplied. This indicates that changes in B2:B1 ratios resulting from alterations to the AveC protein may be specific to particular substrates. Consequently, screening for mutants exhibiting changes in the B2:B1 ratio obtained with a particular substrate needs to be done in the presence of that substrate. The subsequent examples described below use cyclohexanecarboxylic acid as the screening substrate. However, this substrate is used merely to exemplify the potential, and is not intended to limit the applicability, of the present invention.

7. Example

Isolation of the aveC Gene

This example describes the isolation and characterization of a region of the *Streptomyces avermitilis* chromosome that encodes the AveC gene product. As demonstrated below, the aveC gene was identified as capable of modifying the ratio of cyclohexyl-B2 to cyclohexyl-B1 (B2:B1) avermectins produced.

7.1. Materials and Methods

7.1.1. Growth of *Streptomyces* for DNA Isolation

The following method was followed for growing *Streptomyces*. Single colonies of *S. avermitilis* ATCC 31272 (single colony isolate #2) were isolated on ½ strength YPD-6 containing: Difco Yeast Extract—5 g; Difco Bacto-peptone—5 g; dextrose—2.5 g; MOPS—5 g; Difco Bacto agar—15 g. Final volume was adjusted to 1 liter with dH$_2$O, pH was adjusted to 7.0, and the medium was autoclaved at 121° C. for 25 min.

The mycelia grown in the above medium were used to inoculate 10 ml of TSB medium (Difco Tryptic Soy Broth—30 g, in 1 liter dH$_2$O, autoclaved at 121° C. for 25 min) in a 25 mm×150 mm tube which was maintained with shaking (300 rpm) at 28° C. for 48-72 hrs.

7.1.2. Chromosomal DNA Isolation from *Streptomyces*

Aliquots (0.25 ml or 0.5 ml) of mycelia grown as described above were placed in 1.5 ml microcentrifuge tubes and the cells concentrated by centrifugation at 12,000×g for 60 sec. The supernatant was discarded and the cells were resuspended in 0.25 ml TSE buffer (20 ml 1.5 M sucrose, 2.5 ml 1 M Tris-HCl, pH 8.0, 2.5 ml 1 M EDTA, pH 8.0, and 75 ml $dH_2O$) containing 2 mg/ml lysozyme. The samples were incubated at 37° C. for 20 min with shaking, loaded into an AutoGen 540™ automated nucleic acid isolation instrument (Integrated Separation Systems, Natick, Mass.), and genomic DNA isolated using Cycle 159 (equipment software) according to manufacturer's instructions.

Alternatively, 5 ml of mycelia were placed in a 17 mm×100 mm tube, the cells concentrated by centrifugation at 3,000 rpm for 5 min, and the supernatant removed. Cells were resuspended in 1 ml TSE buffer, concentrated by centrifugation at 3,000 rpm for 5 min, and the supernatant removed. Cells were resuspended in 1 ml TSE buffer containing 2 mg/ml lysozyme, and incubated at 37° C. with shaking for 30-60 min. After incubation, 0.5 ml 10% sodium dodecyl sulfate (SDS) was added and the cells incubated at 37° C. until lysis was complete. The lysate was incubated at 65° C. for 10 min, cooled to rm temp, split into two 1.5 ml Eppendorf tubes, and extracted 1× with 0.5 ml phenol/chloroform (50% phenol previously equilibrated with 0.5 M Tris, pH 8.0; 50% chloroform). The aqueous phase was removed and extracted 2 to 5× with chloroform:isoamyl alcohol (24:1). The DNA was precipitated by adding 1/10 volume 3M sodium acetate, pH 4.8, incubating the mixture on ice for 10 min, centrifuging the mixture at 15,000 rpm at 5° C. for 10 min, and removing the supernatant to a clean tube to which 1 volume of isopropanol was added. The supernatant plus isopropanol mixture was then incubated on ice for 20 min, centrifuged at 15,000 rpm for 20 min at 5° C., the supernatant removed, and the DNA pellet washed 1× with 70% ethanol. After the pellet was dry, the DNA was resuspended in TE buffer (10 mM Tris, 1 mM EDTA, pH 8.0).

7.1.3. Plasmid DNA Isolation From *Streptomyces*

An aliquot (1.0 ml) of mycelia was placed in 1.5 ml microcentrifuge tubes and the cells concentrated by centrifugation at 12,000×g for 60 sec. The supernatant was discarded, the cells were resuspended in 1.0 ml 10.3% sucrose and concentrated by centrifugation at 12,000×g for 60 sec, and the supernatant discarded. The cells were then resuspended in 0.25 ml TSE buffer containing 2 mg/ml lysozyme, and incubated at 37° C. for 20 min with shaking and loaded into the AutoGen 540™ automated nucleic acid isolation instrument. Plasmid DNA was isolated using Cycle 106 (equipment software) according to manufacturer's instructions.

Alternatively, 1.5 ml of mycelia were placed in 1.5 ml microcentrifuge tubes and the cells concentrated by centrifugation at 12,000×g for 60 sec. The supernatant was discarded, the cells were resuspended in 1.0 ml 10.3% sucrose and concentrated by centrifugation at 12,000×g for 60 sec, and the supernatant discarded. The cells were resuspended in 0.5 ml TSE buffer containing 2 mg/ml lysozyme, and incubated at 37° C. for 15-30 min. After incubation, 0.25 ml alkaline SDS (0.3N NaOH, 2% SDS) was added and the cells incubated at 55° C. for 15-30 min or until the solution was clear. Sodium acetate (0.1 ml, 3M, pH 4.8) was added to the DNA solution, which was then incubated on ice for 10 min. The DNA samples were centrifuged at 14,000 rpm for 10 min at 5° C. The supernatant was removed to a clean tube, and 0.2 ml phenol:chloroform (50% phenol:50% chloroform) was added and gently mixed. The DNA solution was centrifuged at 14,000 rpm for 10 min at 5° C. and the upper layer removed to a clean Eppendorf tube. Isopropanol (0.75 ml) was added, and the solution was gently mixed and then incubated at rm temp for 20 min. The DNA solution was centrifuged at 14,000 rpm for 15 min at 5° C., the supernatant removed, and the DNA pellet was washed with 70% ethanol, dried, and resuspended in TE buffer.

7.1.4. Plasmid DNA Isolation From *E. coli*

A single transformed *E. coli* colony was inoculated into 5 ml Luria-Bertanl (LB) medium (Bacto-Tryptone—10 g, Bacto-yeast extract—5 g, and NaCl—10 g in 1 liter $dH_2O$, pH 7.0, autoclaved at 121° C. for 25 min, and supplemented with 100 µg/ml ampicillin). The culture was incubated overnight, and a 1 ml aliquot placed in a 1.5 ml microcentrifuge tube. The culture samples were loaded into the AutoGen 540% automated nucleic acid isolation instrument and plasmid DNA was isolated using Cycle 3 (equipment software) according to manufacturer's instructions.

7.1.5. Preparation and Transformation of *S. avermitilis* Proloplasts

Single colonies of *S. avermitilis* were isolated on ½ strength YPD-6. The mycelia were used to inoculate 10 ml of TSB medium in a 25 mm×150 mm tube, which was then incubated with shaking (300 rpm) at 28° C. for 48 hrs. One ml of mycelia was used to inoculate 50 ml YEME medium. YEME medium contains per liter: Difco Yeast Extract—3 g; Difco Bacto-peptone—5 g; Difco Malt Extract—3 g; Sucrose—300 g. After autoclaving at 121° C. for 25 min, the following were added: 2.5 M $MgCl_2$ $6H_2O$ (separately autoclaved at 121° C. for 25 min)-2 ml; and glycine (20%) (filter-sterilized)-25 ml.

The mycelia were grown at 30° C. for 48-72 hrs and harvested by centrifugation in a 50 ml centrifuge tube (Falcon) at 3,000 rpm for 20 min. The supernatant was discarded and the mycelia were resuspended in P buffer, which contains: sucrose—205 g; $K_2SO_4$—0.25 g; $MgCl_2.6H_2O$—2.02 g; $H_2O$—600 ml; $K_2PO_4$ (0.5%)—10 ml; trace element solution—20 ml; $CaCl_2.2H_2O$ (3.68%)—100 ml; and MES buffer (1.0 M, pH 6.5)—10 ml. (*Trace element solution contains per liter: $ZnCl_2$—40 mg; $FeCl_3$ $6H_2O$—200 mg; $CuCl_2.2H_2O$—10 mg; $MnCl_2$. $4H_2O$—10 mg; $Na_2B_4O_7.10H_2O$—10 mg; $(NH_4)_6$ $Mo_7O_{24}.4H_2O$—10 mg). The pH was adjusted to 6.5, final volume was adjusted to 1 liter, and the medium was filtered hot through a 0.45 micron filter.

The mycelia were pelleted at 3,000 rpm for 20 min, the supernatant was discarded, and the mycelia were resuspended in 20 ml P buffer containing 2 mg/ml lysozyme. The mycelia were incubated at 35° C. for 15 min with shaking, and checked microscopically to determine extent of protoplast formation. When protoplast formation was complete, the protoplasts were centrifuged at 8,000 rpm for 10 min. The supernatant was removed and the protoplasts were resuspended in 10 ml P buffer. The protoplasts were centrifuged at 8,000 rpm for 10 min, the supernatant was removed, the protoplasts were resuspended in 2 ml P buffer, and approximately $1 \times 10^9$ protoplasts were distributed to 2.0 ml cryogenic vials (Nalgene).

A vial containing $1 \times 10^9$ protoplasts was centrifuged at 8,000 rpm for 10 min, the supernatant was removed, and the protoplasts were resuspended in 0.1 ml P buffer. Two to 5 µg of transforming DNA were added to the protoplasts, immediately followed by the addition of 0.5 ml working T buffer. T buffer base contains: PEG-1000 (Sigma)—25 g; sucrose—2.5 g; $H_2O$—83 ml. The pH was adjusted to 8.8 with 1 N NaOH (filter sterilized), and the T buffer base was filter-sterilized and stored at 4° C. Working T buffer, made the same day used, was T buffer base—8.3 ml; $K_2PO_4$ (4 mM)-1.0 ml; $CaCl_2$ $2H_2O$ (5 M)-0.2 ml; and TES (1 M, pH 8)-0.5 ml. Each component of the working T buffer was individually filter-sterilized.

Within 20 sec of adding T buffer to the protoplasts, 1.0 ml P buffer was also added and the protoplasts were centrifuged at 8,000 rpm for 10 min. The supernatant was discarded and the protoplasts were resuspended in 0.1 ml P buffer. The protoplasts were then plated on RM14 media, which contains: sucrose—205 g; $K_2SO_4$—0.25 g; $MgCl_2.6H_2O$—10.12 g; glucose—10 g; Difco Casamino Acids—0.1 g; Difco Yeast Extract—5 g; Difco Oatmeal Agar—3 g; Difco Bacto Agar—22 g; $dH_2O$—800 ml. The solution was autoclaved at 121° C. for 25 min. After autoclaving, sterile stocks of the following were added: $K_2PO_4$ (0.5%)-10 ml; $CaCl_2$ $2H_2O$ (5 M)-5 ml; L-proline (20%)-15 ml; MES buffer (1.0 M, pH 6.5)-10 ml; trace element solution (same as above)-2 ml; cycloheximide stock (25 mg/ml)-40 ml; and 1N NaOH—2 ml. Twenty-five ml of RM14 medium were aliquoted per plate, and plates dried for 24 hr before use.

The protoplasts were incubated in 95% humidity at 30° C. for 20-24 hrs. To select thiostrepton resistant transformants, 1 ml of overlay buffer containing 125 μg per ml thiostrepton was spread evenly over the RM14 regeneration plates. Overlay buffer contains per 100 ml: sucrose—10.3 g; trace element solution (same as above)—0.2 ml; and MES (1 M, pH 6.5)—1 ml. The protoplasts were incubated in 95% humidity at 30° C. for 7-14 days until thiostrepton resistant ($Thio^r$) colonies were visible.

7.1.6. Transformation of *Streptomyces lividans* Protoplasts

*S. lividans* TK64 (provided by the John Innes Institute, Norwich, U.K) was used for transformations in some cases. Methods and compositions for growing, protoplasting, and transforming *S. lividans* are described in Hopwood et al., 1985, *Genetic Manipulation of Strentomyces, A Laboratory Manual*, John Innes Foundation, Norwich, U.K., and performed as described therein. Plasmid DNA was isolated from *S. lividans* transformants as described in Section 7.1.3, above.

7.1.7. Fermentation Analysis of *S. avermitilis* Strains

*S. avermitilis* mycelia grown on ½ strength YPD-6 for 4-7 days were inoculated into 1×6 inch tubes containing 8 ml of preform medium and two 5 mm glass beads. Preform medium contains: soluble starch (either thin boiled starch or KOSO, Japan Corn Starch Co., Nagoya)—20 g/L; Pharmamedia—15 g/L; Ardamine pH—5 g/L (Champlain Ind., Clifton, N.J.); $CaCO_3$—2 g/L; 2× bcfa ("bcfa" refers to branched chain fatty acids) containing a final concentration in the medium of 50 ppm 2-(+/−)-methyl butyric acid, 60 ppm isobutyric acid, and 20 ppm isovaleric acid. The pH was adjusted to 7.2, and the medium was autoclaved at 121° C. for 25 min.

The tube was shaken at a 17° angle at 215 rpm at 29° C. for 3 days. A 2-ml aliquot of the seed culture was used to inoculate a 300 ml Erlenmeyer flask containing 25 ml of production medium which contains: starch (either thin boiled starch or KOSO)-160 g/L; Nutrisoy (Archer Daniels Midland, Decatur, Ill.)—10 g/L; Ardamine pH—10 g/L; $K_2HPO_4$—2 g/L; $MgSO_4.4H_2O$—2 g/L; $FeSO_4.7H_2O$—0.02 g/L; $MnCl_2$—0.002 g/L; $ZnSO_4.7H_2O$—0.002 g/L; $CaCO_3$—14 g/L; 2× bcfa (as above); and cyclohexane carboxylic acid (CHC) (made up as a 20% solution at pH 7.0)—800 ppm. The pH was adjusted to 6.9, and the medium was autoclaved at 121° C. for 25 min. (As explained above, starter units other than CHC can be utilized instead (see, e.g., Table 1)).

After inoculation, the flask was incubated at 29° C. for 12 days with shaking at 200 rpm. After incubation, a 2 ml sample was withdrawn from the flask, diluted with 8 ml of methanol, mixed, and the mixture centrifuged at 1,250×g for 10 min to pellet debris. The supernatant was then assayed by HPLC using a Beckman Ultrasphere ODS column (25 cm×4.6 mm ID) with a flow rate of 0.75 ml/min and detection by absorbance at 240 nm. The mobile phase was 86/8.9/5.1 methanol/water/acetonitrile.

7.1.8. Isolation of *S. avermitilis* PKS Genes

A cosmid library of *S. avermitilis* (ATCC 31272, SC-2) chromosomal DNA was prepared and hybridized with a keto-synthase (KS) probe made from a fragment of the *Saccharopolyspora erythraea* polyketide synthase (PKS) gene. A detailed description of the preparation of cosmid libraries can be found in Sambrook et al., 1989, above. A detailed description of the preparation of *Streptomyces* chromosomal DNA libraries is presented in Hopwood et al., 1985, above. Cosmid clones containing ketosynthase-hybridizing regions were identified by hybridization to a 2.7 Kb NdeI/Eco47III fragment from pEX26 (kindly supplied by Dr. P. Leadlay, Cambridge, UK). Approximately 5 ng of pEX26 were digested using NdeI and Eco47III. The reaction mixture was loaded on a 0.8% SeaPlaque GTG agarose gel (FMC BioProducts, Rockland, Me.). The 2.7 Kb NdeI/Eco47III fragment was excised from the gel after electrophoresis and the DNA recovered from the gel using GELase™ from Epicentre Technologies using the Fast Protocol. The 2.7 Kb NdeI/Eco47III fragment was labeled with [α-$^{32}$P]dCTP (deoxycytidine 5'-triphosphate, tetra (triethylammonium) salt, [alpha-$^{32}$P]-) (NEN-Dupont, Boston, Mass.) using the BRL Nick Translation System (BRL Life Technologies, Inc., Gaithersburg, Md.) following the supplier's instructions. A typical reaction was performed in 0.05 ml volume. After addition of 5 μl Stop buffer, the labeled DNA was separated from unincorporated nucleotides using a G-25 Sephadex Quick Spin™ Column (Boehringer Mannheim) following supplier's instructions.

Figure 4:
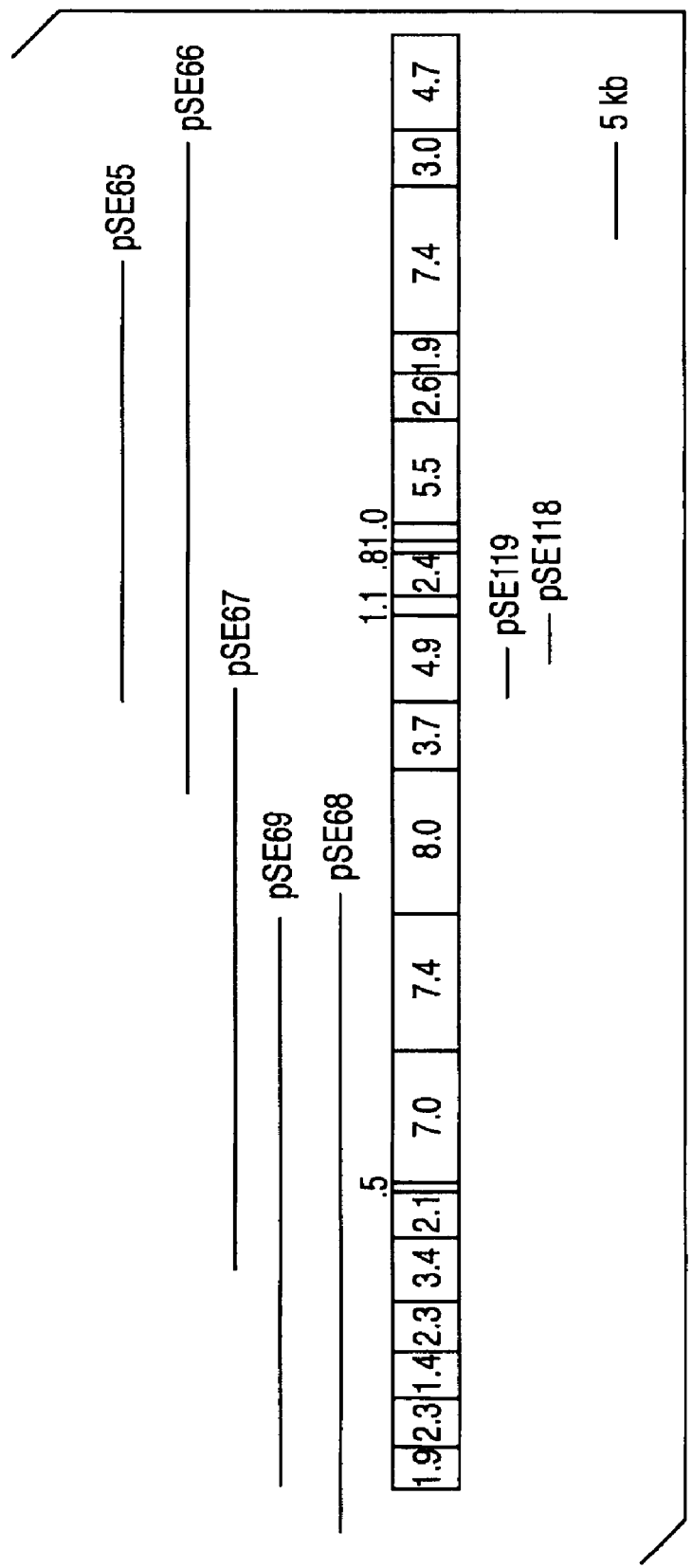
FIG. 4. BamHI restriction map of the avermectin polyketide synthase gene cluster from *S. avermitilis* with five overlapping cosmid clones identified (i.e., pSE65, pSE66, pSE67, pSE68, pSE69). The relationship of pSE118 and pSE119 is also indicated.

Approximately 1,800 cosmid clones were screened by colony hybridization. Ten clones were identified that hybridized strongly to the *Sacc. erythraea* KS probe. *E. coli* colonies containing cosmid DNA were grown in LB liquid medium and cosmid DNA was isolated from each culture in the Auto-Gen 540™ automated nucleic acid isolation instrument using Cycle 3 (equipment software) according to manufacturer's instructions. Restriction endonuclease mapping and Southern blot hybridization analyses revealed that five of the clones contained overlapping chromosomal regions. An *S. avermitilis* genomic BamHI restriction map of the five cosmids (i.e., pSE65, pSE66, pSE67, pSE68, pSE69) was constructed by analysis of overlapping cosmids and hybridizations (FIG. 4).

7.1.9. Identification of DNA that Modulates

Avermectin B2:B1 Ratios and

Identification of an aveC ORF

The following methods were used to test subcloned fragments derived from the pSE66 cosmid clone for their ability to modulate avermectin B2:B1 ratios in AveC mutants. pSE66 (5 µg) was digested with SacI and BamHI. The reaction mixture was loaded on a 0.8% SeaPlaque™ GTG agarose gel (FMC BioProducts), a 2.9 Kb SacI/BamHI fragment was excised from the gel after electrophoresis, and the DNA was recovered from the gel using GELase™ (Epicentre Technologies) using the Fast Protocol. Approximately 5 μg of the shuttle vector pWHM3 (Vara et al., 1989, J. Bacteriol. 171: 5872-5881) was digested with SacI and BamHI. About 0.5 μL of the 2.9 Kb insert and 0.5 μg of digested pWHM3 were mixed together and incubated overnight with 1 unit of ligase (New England Biolabs, Inc., Beverly, Mass.) at 15° C., in a total volume of 20 μl, according to supplier's instructions. After incubation, 5 μl of the ligation mixture was incubated at 70° C. for 10 min, cooled to rm temp, and used to transform competent *E. coli* DH5α cells (BRL) according to manufacturer's instructions. Plasmid DNA was isolated from ampicillin resistant transformants and the presence of the 2.9 Kb SacI/BamHI insert was confirmed by restriction analysis. This plasmid was designated as pSE119.

Protoplasts of *S. avermitilis* strain 1100-SC38 (Pfizer in-house strain) were prepared and transformed with pSE119 as described in Section 7.1.5 above. Strain 1100-SC38 is a mutant that produces significantly more of the avermectin cyclohexyl-B2 form compared to avermectin cyclohexyl-B1 form when supplemented with cyclohexane carboxylic acid (B2:B1 of about 30:1). pSE119 used to transform *S. avermitilis* protoplasts was isolated from either *E. coli* strain GM2163 (obtained from Dr. B. J. Bachmann, Curator, *E. coli* Genetic Stock Center, Yale University), *E. coli* strain DM1 (BRL), or *S. lividans* strain TK64. Thiostrepton resistant transformants of strain 1100-SC38 were isolated and analyzed by HPLC analysis of fermentation products. Transformants of *S. avermitilis* strain 1100-SC38 containing pSE119 produced an altered ratio of avermectin cyclohexyl-B2:cyclohexyl-B1 of about 3.7:1 (TABLE 2).

Having established that pSE119 was able to modulate avermectin B2:B1 ratios in an AveC mutant, the insert DNA was sequenced. Approximately 10 μg of pSE119 were isolated using a plasmid DNA isolation kit (Qiagen, Valencia, Calif.) following manufacturer's instructions, and sequenced using an ABI 373A Automated DNA Sequencer (Perkin Elmer, Foster City, Calif.). Sequence data was assembled and edited using Genetic Computer Group programs (GCG, Madison, Wis.). The DNA sequence and the aveC ORF are presented in FIG. 1 (SEQ ID NO:1).

A new plasmid, designated as pSE118, was constructed as follows. Approximately 5 μg of pSE66 was digested with SphI and BamHI. The reaction mixture was loaded on a 0.8% SeaPlaque GTG agarose gel (FMC BioProducts), a 2.8 Kb SphI/BamHI fragment was excised from the gel after electrophoresis, and the DNA was recovered from the gel using GELase™ (Epicentre Technologies) using the Fast Protocol. Approximately 5 μg of the shuttle vector pWHM3 was digested with SphI and BamHI. About 0.5 μg of the 2.8 Kb insert and 0.5 μg of digested pWHM3 were mixed together and incubated overnight with 1 unit of ligase (New England Biolabs) at 15° C. in a total volume of 20 μl according to supplier's instructions. After incubation, 5 μl of the ligation mixture was incubated at 70° C. for 10 min, cooled to rm temp, and used to transform competent *E. coli* DH5α cells according to manufacturer's instructions. Plasmid DNA was isolated from ampicillin resistant transformants, and the presence of the 2.8 Kb SphI/BamHI insert was confirmed by restriction analysis. This plasmid was designated as pSE118. The insert DNA in pSE118 and pSE119 overlap by approximately 838 nucleotides (FIG. 4).

Protoplasts of *S. avermitilis* strain 1100-SC38 were transformed with pSE118 as above. Thiostrepton resistant transformants of strain 1100-SC38 were isolated and analyzed by HPLC analysis of fermentation products. Transformants of *S. avermitilis* strain 1100-SC38 containing pSE118 were not altered in the ratios of avermectin cyclohexyl-B2: avermectin cyclohexyl-B1 compared to strain 1100-SC38 (TABLE 2).

7.1.10. PCR Amplification of the aveC Gene from *S. avermitilis* Chromosomal DNA A ~1.2 Kb fragment containing the aveC ORF was isolated from *S. avermitilis* chromosomal DNA by PCR amplification using primers designed on the basis of the aveC nucleotide sequence obtained above. The PCR primers were supplied by Genosys Biotechnologies, Inc. (Texas). The rightward primer was: 5'-TCACGAAACCGGACACAC-3' (SEQ ID NO:6); and the leftward primer was: 5'-CATGATCGCTGAACCGAG-3' (SEQ ID NO:7). The PCR reaction was carried out with Deep Vent™ polymerase (New England Biolabs) in buffer provided by the manufacturer, and in the presence of 300 μM dNTP, 10% glycerol, 200 pmol of each primer, 0.1 μg template, and 2.5 units enzyme in a final volume of 100 μl, using a Perkin-Elmer Cetus thermal cycler. The thermal profile of the first cycle was 95° C. for 5 min (denaturation step), 60° C. for 2 min (annealing step), and 72° C. for 2 min (extension step). The subsequent 24 cycles had a similar thermal profile except that the denaturation step was shortened to 45 sec and the annealing step was shortened to 1 min.

The PCR product was electrophoresed in a 1% agarose gel and a single DNA band of ~1.2 Kb was detected. This DNA was purified from the gel, and ligated with 25 ng of linearized, blunt pCR-Blunt vector (Invitrogen) in a 1:10 molar vector-to-insert ratio following manufacturer's instructions. The ligation mixture was used to transform One Shot™ Competent *E. coli* cells (Invitrogen) following manufacturer's instructions. Plasmid DNA was isolated from ampicillin resistant transformants, and the presence of the ~1.2 Kb insert was confirmed by restriction analysis. This plasmid was designated as pSE179.

The insert DNA from pSE179 was isolated by digestion with BamHI/XbaI, separated by electrophoresis, purified from the gel, and ligated with shuttle vector pWHM3, which had also been digested with BamHI/XbaI, in a total DNA concentration of 1 μg in a 1:5 molar vector-to-insert ratio. The ligation mixture was used to transform competent *E. coli* DH5α cells according to manufacturer's instructions. Plasmid DNA was isolated from ampicillin resistant transformants and the presence of the ~1.2 Kb insert was confirmed by restriction analysis. This plasmid, which was designated as pSE186 (FIG. 2, ATCC 209604), was transformed into *E. coli* DM1, and plasmid DNA was isolated from ampicillin resistant transform ants.

7.2. Results

A 2.9 Kb SacI/BamHI fragment from pSE119 was identified that, when transformed into *S. avermitilis* strain 1100-SC38, significantly altered the ratio of B2:B1 avermectin production. *S. avermitilis* strain 1100-SC38 normally has a B2:B1 ratio of about 30:1, but when transformed with a vector comprising the 2.9 Kb SacI/BamHI fragment, the ratio of B2:B1 avermectin decreased to about 3.7:1. Post-fermentation analysis of transformant cultures verified the presence of the transforming DNA.

The 2.9 Kb pSE119 fragment was sequenced and a ~0.9 Kb ORF was identified (FIG. 1) (SEQ ID NO:1), which encompasses a PstI/SphI fragment that had previously been mutated elsewhere to produce B2 products only (Ikeda et al., 1995, above). A comparison of this ORF, or its corresponding deduced polypeptide, against known databases (GenEMBL, SWISS-PROT) did not show any strong homology with known DNA or protein sequences.

TABLE 2 presents the fermentation analysis of *S. avermitilis* strain 1100-SC38 transformed with various plasmids.

TABLE 2

| S. avermitilis strain (transforming plasmid) | No. Transformants Tested | Avg. B2:B1 Ratio |
| --- | --- | --- |
| 1100-SC38 (none) | 9 | 30.66 |
| 1100-SC38 (pWHM3) | 21 | 31.3 |
| 1100-SC38 (pSE119) | 12 | 3.7 |
| 1100-SC38 (pSE118) | 12 | 30.4 |
| 1100-SC38 (pSE185) | 14 | 27.9 |

8. Example

Construction of

S. avermitilis AveC Mutants

This example describes the construction of several different *S. avermitilis* AveC mutants using the compositions and methods described above. A general description of techniques for introducing mutations into a gene in *Streptomyces* is described by Kieser and Hopwood, 1991, Meth. Enzym. 204:430-458. A more detailed description is provided by Anzai et al., 1988, J. Antibiot. XLI (2):226-233, and by Stutzman-Engwall et al., 1992, J. Bacteriol. 174(1):144-154. These references are incorporated herein by reference in their entirety.

8.1. Inactivation of the *S. avermitilis* aveC Gene

AveC mutants containing inactivated aveC genes were constructed using several methods, as detailed below.

Figure 5A:
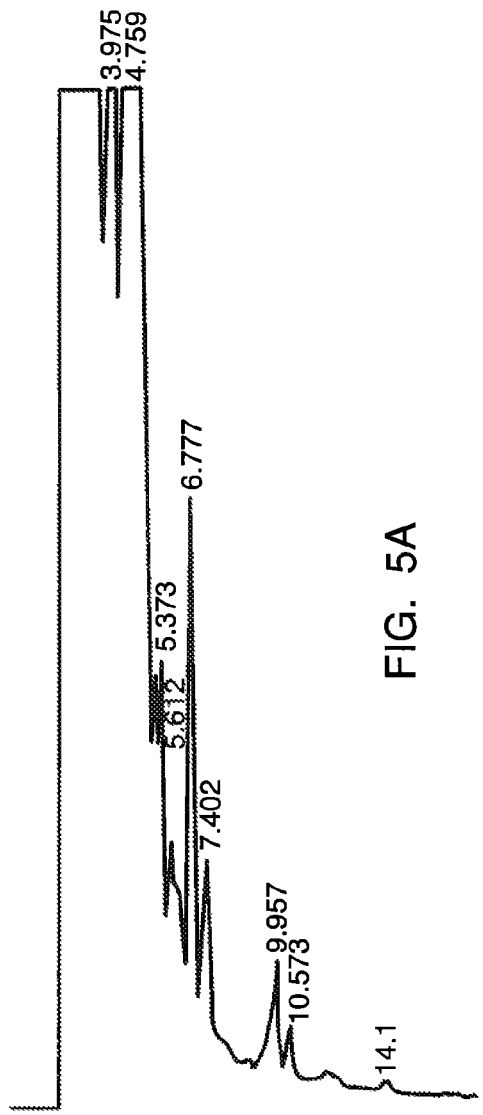
FIG. 5A. *S. avermitilis* strain SE180-11 with an inactivated aveC ORF.

In the first method, a 640 bp SphI/PstI fragment internal to the aveC gene in pSE119 (plasmid described in Section 7.1.9, above) was replaced with the ermE gene (for erythromycin resistance) from *Sacc. erythraea*. The ermE gene was isolated from pIJ4026 (provided by the John Innes Institute, Norwich, U.K.; see also Bibb et al., 1985, *Gene* 41:357-368) by restriction enzyme digestion with Bg/II and EcoRI, followed by electrophoresis, and was purified from the gel. This ~1.7 Kb fragment was ligated into pGEM7Zf (Promega) which had been digested with BamHI and EcoRI, and the ligation mixture transformed into competent *E. coli* DH5α cells following manufacturer's instructions. Plasmid DNA was isolated from ampicillin resistant transformants, and the presence of the ~1.7 Kb insert was confirmed by restriction analysis. This plasmid was designated as pSE27.

pSE118 (described in Section 7.1.9, above) was digested with SphI and BamHI, the digest electrophoresed, and the ~2.8 Kb SphI/BamHI insert purified from the gel. pSE119 was digested with PstI and EcoRI, the digest electrophoresed, and the ~1.5 Kb PstI/EcoRI insert purified from the gel. Shuttle vector pWHM3 was digested with BamHI and EcoRI. pSE27 was digested with PstI and SphI, the digest electrophoresed, and the ~1.7 Kb PstI/SphI insert purified from the gel. All four fragments (i.e., ~2.8 Kb, ~1.5 Kb, ~7.2 Kb, ~1.7 Kb) were ligated together in a 4-way ligation. The ligation mixture was transformed into competent *E. coli* DH5α cells following manufacturer's instructions. Plasmid DNA was isolated from ampicillin resistant transformants, and the presence of the correct insert was confirmed by restriction analysis. This plasmid was designated as pSE180 (FIG. 3; ATCC 209605).

pSE180 was transformed into *S. lividans* TK64 and transformed colonies identified by resistance to thiostrepton and erythromycin. pSE180 was isolated from *S. lividans* and used to transform *S. avermitilis* protoplasts. Four thiostrepton resistant *S. avermitilis* transformants were identified, and protoplasts were prepared and plated under non-selective conditions on RM14 media. After the protoplasts had regenerated, single colonies were screened for the presence of erythromycin resistance and the absence of thiostrepton resistance, indicating chromosomal integration of the inactivated aveC gene and loss of the free replicon. One Erm$^r$ Thio$^s$ transformant was identified and designated as strain SE180-11. Total chromosomal DNA was isolated from strain SE180-11, digested with restriction enzymes BamHI, HindIII, PstI, or SphI, resolved by electrophoresis on a 0.8% agarose gel, transferred to nylon membranes, and hybridized to the ermE probe. These analyses showed that chromosomal integration of the ermE resistance gene, and concomitant deletion of the 640 bp PstI/SphI fragment had occurred by a double crossover event. HPLC analysis of fermentation products of strain SE180-11 showed that normal avermectins were no longer produced (FIG. 5A).

In a second method for inactivating the aveC gene, the 1.7 Kb ermE gene was removed from the chromosome of *S. avermitilis* strain SE180-11, leaving a 640 bp PstI/SphI deletion in the aveC gene. A gene replacement plasmid was constructed as follows: pSE180 was partially digested with XbaI and an ~11.4 Kb fragment purified from the gel. The ~11.4 Kb band lacks the 1.7 Kb ermE resistance gene. The DNA was then ligated and transformed into *E. coli* DH5α cells. Plasmid DNA was isolated from ampicillin resistant transformants and the presence of the correct insert was confirmed by restriction analysis. This plasmid, which was designated as pSE184, was transformed into *E. coli* DM1, and plasmid DNA isolated from ampicillin resistant transformants. This plasmid was used to transform protoplasts of *S. avermitilis* strain SE180-11. Protoplasts were prepared from thiostrepton resistant transformants of strain SE180-11 and were plated as single colonies on RM14. After the protoplasts had regenerated, single colonies were screened for the absence of both erythromycin resistance and thiostrepton resistance, indicating chromosomal integration of the inactivated aveC gene and loss of the free replicon containing the ermE gene. One Erm$^s$ Thio$^s$ transformant was identified and designated as SE184-1-13. Fermentation analysis of SE184-1-13 showed that normal avermectins were not produced and that SE184-1-13 had the same fermentation profile as SE180-11.

In a third method for inactivating the aveC gene, a frameshift was introduced into the chromosomal aveC gene by adding two G's after the C at nt position 471 using PCR, thereby creating a BspE1 site. The presence of the engineered BspE1 site was useful in detecting the gene replacement event. The PCR primers were designed to introduce a frameshift mutation into the aveC gene, and were supplied by Genosys Biotechnologies, Inc. The rightward primer was: 5'-GGTTCCGGATGCCGTTCTCG-3' (SEQ ID NO:8) and the leftward primer was: 5'-AACTCCGGTCGACTC-CCCTTC-3' (SEQ ID NO:9). The PCR conditions were as described in Section 7.1.10 above. The 666 bp PCR product was digested with SphI to give two fragments of 278 bp and 388 bp, respectively. The 388 bp fragment was purified from the gel.

The gene replacement plasmid was constructed as follows: shuttle vector pWHM3 was digested with EcoRI and BamHI. pSE119 was digested with BamHI and SphI, the digest electrophoresed, and a ~840 bp fragment was purified from the gel. pSE119 was digested with EcoRI and XmnI, the digest was resolved by electrophoresis, and a ~1.7 Kb fragment was purified from the gel. All four fragments (i.e., ~7.2 Kb, ~840 bp, ~1.7 Kb, and 388 bp) were ligated together in a 4-way ligation. The ligation mixture was transformed into competent E. coli DH5α cells. Plasmid DNA was isolated from ampicillin resistant transformants and the presence of the correct insert was confirmed by restriction analysis and DNA sequence analysis. This plasmid, which was designated as pSE185, was transformed into E. coli DM1 and plasmid DNA isolated from ampicillin resistant transformants. This plasmid was used to transform protoplasts of S. avermitilis strain 1100-SC38. Thiostrepton resistant transformants of strain 1100-SC38 were isolated and analyzed by HPLC analysis of fermentation products. pSE185 did not significantly alter the B2:B1 avermectin ratios when transformed into S. avermitilis strain 1100-SC38 (TABLE 2).

pSE185 was used to transform protoplasts of S. avermitilis to generate a frameshift mutation in the chromosomal aveC gene. Protoplasts were prepared from thiostrepton resistant transformants and plated as single colonies on RM14. After the protoplasts had regenerated, single colonies were screened for the absence of thiostrepton resistance. Chromosomal DNA from thiostrepton sensitive colonies was isolated and screened by PCR for the presence of the frameshift mutation integrated into the chromosome. The PCR primers were designed based on the aveC nucleotide sequence, and were supplied by Genosys Biotechnologies, Inc. (Texas). The rightward PCR primer was: 5'-GCAAGGATACGGGGAC-TAC-3' (SEQ ID NO:10) and the leftward PCR primer was: 5'-GAACCGACCGCCTGATAC-3' (SEQ ID NO:11), and the PCR conditions were as described in Section 7.1.10 above. The PCR product obtained was 543 bp and, when digested with BspE1, three fragments of 368 bp, 96 bp, and 79 bp were observed, indicating chromosomal integration of the inactivated aveC gene and loss of the free replicon.

Fermentation analysis of S. avermitilis mutants containing the frameshift mutation in the aveC gene showed that normal avermectins were no longer produced, and that these mutants had the same fermentation HPLC profile as strains SE180-11 and SE184-1-13. One Thio$^s$ transformant was identified and designated as strain SE185-5a.

Additionally, a mutation in the aveC gene that changes nt position 520 from G to A, which results in changing the codon encoding a tryptophan (W) at position 116 to a termination codon, was produced. An S. avermitilis strain with this mutation did not produce normal avermectins and had the same fermentation profile as strains SE180-11, SE184-1-13, and SE185-5a.

Additionally, mutations in the aveC gene that change both: (i) nt position 970 from G to A, which changes the amino acid at position 266 from a glycine (G) to an aspartate (D), and (ii) nt position 996 from T to C, which changes the amino acid at position 275 from tyrosine (Y) to histidine (H), were produced. An S. avermitilis strain with these mutations (G266D/Y275H) did not produce normal avermectins and had the same fermentation profile as strains SE180-11, SE184-1-13, and SE185-5a.

Figure 5B:
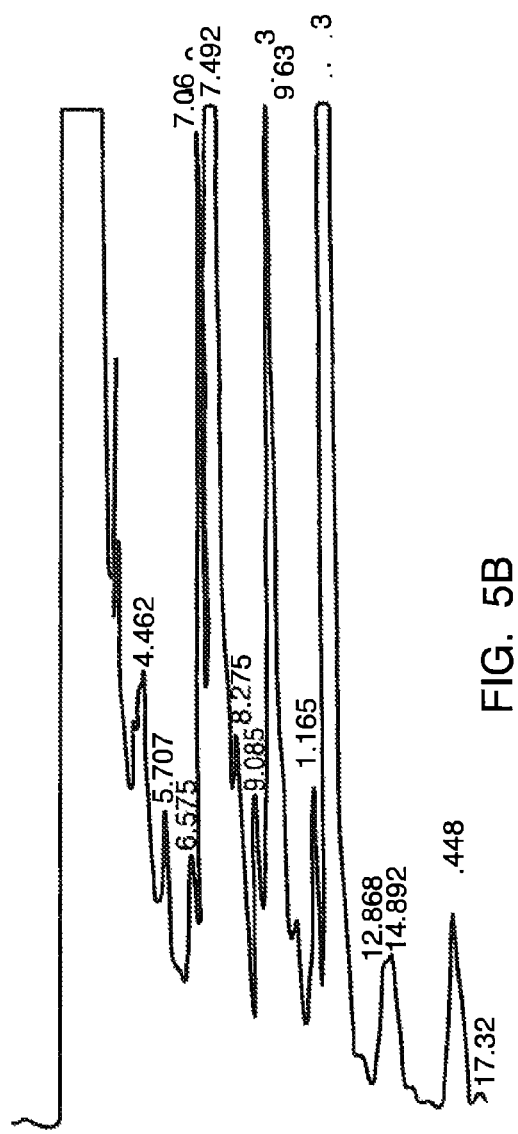
FIG. 5B. *S. avermitilis* strain SE180-11 transformed with pSE186 (ATCC 209604).

The S. avermitilis aveC inactivation mutant strains SE180-11, SE184-1-13, SE185-5a, and others provided herewith, provide screening tools to assess the impact of other mutations in the aveC gene. pSE186, which contains a wild-type copy of the aveC gene, was transformed into E. coli DM1, and plasmid DNA was isolated from ampicillin resistant transformants. This pSE186 DNA was used to transform protoplasts of S. avermitilis strain SE180-11. Thiostrepton resistant transformants of strain SE180-11 were isolated, the presence of erythromycin resistance was determined, and Thio$^r$ Erm$^r$ transformants were analyzed by HPLC analysis of fermentation products. The presence of the functional aveC gene in trans was able to restore normal avermectin production to strain SE180-11 (FIG. 5B).

8.2. Analysis of Mutations in the aveC

Gene that Ater Class B2:B1 Ratios

As described above, S. avermitilis strain SE180-11 containing an inactive aveC gene was complemented by transformation with a plasmid containing a functional aveC gene (pSE186). Strain SE180-11 was also utilized as a host strain to characterize other mutations in the aveC gene, as described below.

Figure 5C:
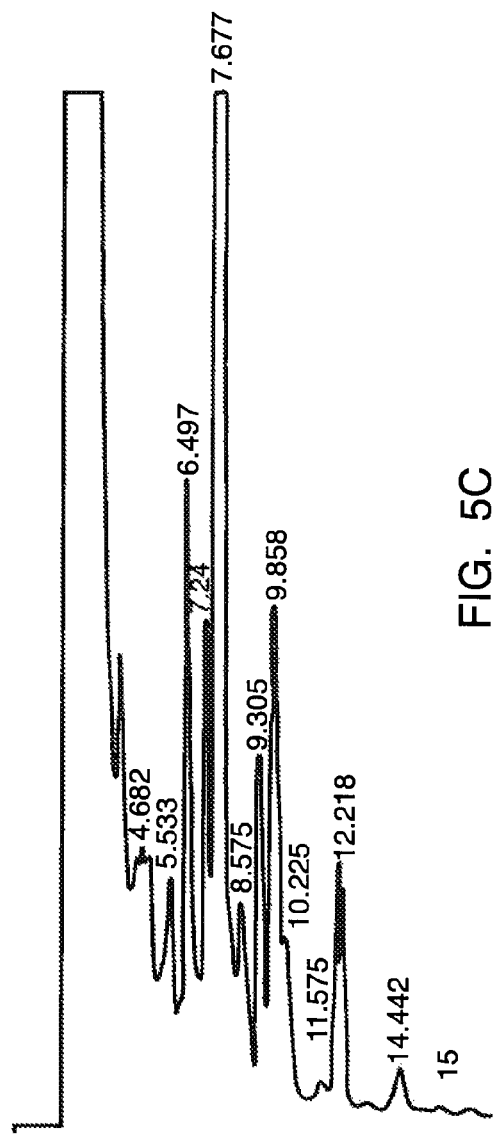
FIG. 5C. *S. avermitilis* strain SE180-11 transformed with pSE187.

Chromosomal DNA was isolated from strain 1100-SC38, and used as a template for PCR amplification of the aveC gene. The 1.2 Kb ORF was isolated by PCR amplification using primers designed on the basis of the aveC nucleotide sequence. The rightward primer was SEQ ID NO:6 and the leftward primer was SEQ ID NO:7 (see Section 7.1.10, above). The PCR and subcloning conditions were as described in Section 7.1.10. DNA sequence analysis of the 1.2 Kb ORF shows a mutation in the aveC gene that changes nt position 337 from C to T, which changes the amino acid at position 55 from serine (S) to phenylalanine (F). The aveC gene containing the S55F mutation was subcloned into pWHM3 to produce a plasmid which was designated as pSE187, and which was used to transform protoplasts of S. avermitilis strain SE180-11 Thiostrepton resistant transformants of strain SE180-11 were isolated, the presence of erythromycin resistance was determined, and Thio$^r$ Erm$^r$ transformants were analyzed by HPLC analysis of fermentation products. The presence of the aveC gene encoding a change at amino acid residue 55 (S55F) was able to restore normal avermectin production to strain SE180-11 (FIG. 5C); however, the cyclohexyl B2:cyclohexyl B1 ratio was about 26:1, as compared to strain SE180-11 transformed with pSE186, which had a ratio of B2:B1 of about 1.6:1 (TABLE 3), indicating that the single mutation (S55F) modulates the amount of cyclohexyl-B2 produced relative to cyclohexyl-B1.

Another mutation in the aveC gene was identified that changes nt position 862 from G to A, which changes the amino acid at position 230 from glycine (G) to aspartate (D). An S. avermitilis strain having this mutation (G230D) produces avermectins at a B2:B1 ratio of about 30:1.

8.3. Mutations that Reduce the B2:B1 Ratio

Several mutations were constructed that reduce the amount of cyclohexyl-B2 produced relative to cyclohexyl-B1, as follows.

Figure 5D:
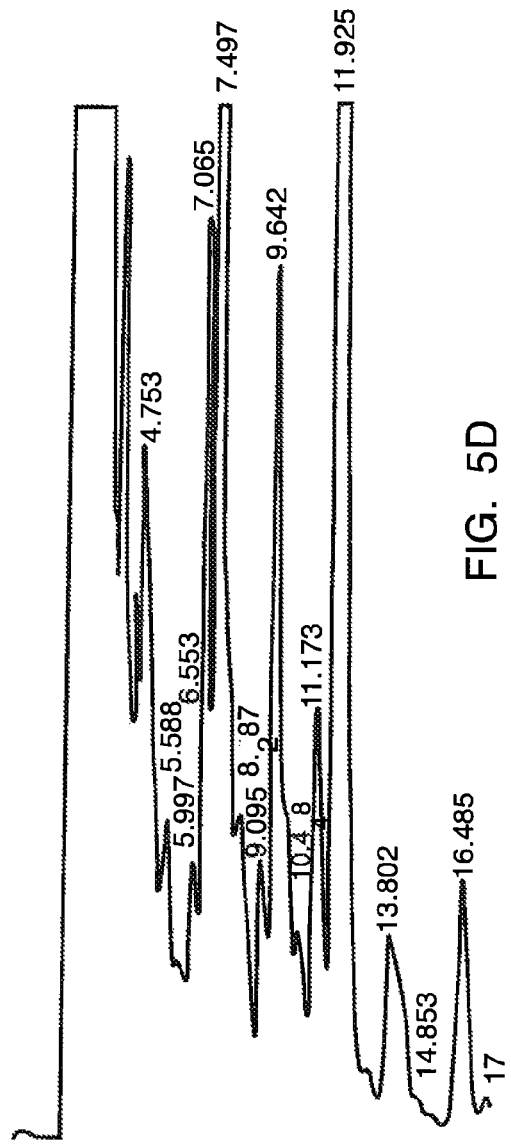
FIG. 5D. *S. avermitilis* strain SE180-11 transformed with pSE188.

A mutation in the aveC gene was identified that changes nt position 588 from G to A, which changes the amino acid at position 139 from alanine (A) to threonine (T). The aveC gene containing the A139T mutation was subcloned into pWHM3 to produce a plasmid which was designated pSE188, and which was used to transform protoplasts of S. avermitilis strain SE180-11. Thiostrepton resistant transformants of strain SE180-11 were isolated, the presence of erythromycin resistance was determined, and Thio^r Erm^r transformants were analyzed by HPLC analysis of fermentation products. The presence of the mutated aveC gene encoding a change at amino acid residue 139 (A139T) was able to restore avermectin production to strain SE180-11 (FIG. 5D); however, the B2:B1 ratio was about 0.94:1, indicating that this mutation reduces the amount of cyclohexyl-B2 produced relative to cyclohexyl-B1. This result was unexpected because published results, as well as the results of mutations described above, have only demonstrated either inactivation of the aveC gene or increased production of the B2 form of avermectin relative to the B1 form (TABLE 3).

Because the A139T mutation altered the B2:B1 ratios in the more favorable B1 direction, a mutation was constructed that encoded a threonine instead of a serine at amino acid position 138. Thus, pSE186 was digested with EcoRI and cloned into pGEM3Zf (Promega) which had been digested with EcoRI. This plasmid, which was designated as pSE186a, was digested with ApaI and KpnI, the DNA fragments separated on an agarose gel, and two fragments of ~3.8 Kb and ~0.4 Kb were purified from the gel. The ~1.2 Kb insert DNA from pSE186 was used as a PCR template to introduce a single base change at nt position 585. The PCR primers were designed to introduce a mutation at nt position 585, and were supplied by Genosys Biotechnologies, Inc. (Texas). The rightward PCR primer was: 5'-GGGGGCGGGCCCGGGT-GCGGAGGCGGAAATGCCCCTGGCGACG-3' (SEQ ID NO:12); and the leftward PCR primer was: 5'-GGAAC-CGACCGCCTGATACA-3' (SEQ ID NO:13). The PCR reaction was carried out using an Advantage GC genomic PCR kit (Clonetech Laboratories, Palo Alto, Calif.) in buffer provided by the manufacturer in the presence of 200 µM dNTPs, 200 pmol of each primer, 50 ng template DNA, 1.0 M GC-Melt and 1 unit KlenTaq Polymerase Mix in a final volume of 50 µl. The thermal profile of the first cycle was 94° C. for 1 min; followed by 25 cycles of 94° C. for 30 sec and 68° C. for 2 min; and 1 cycle at 68° C. for 3 min. A PCR product of 295 bp was digested with ApaI and KpnI to release a 254 bp fragment, which was resolved by electrophoresis and purified from the gel. All three fragments (~3.8 Kb, ~0.4 Kb and 254 bp) were ligated together in a 3-way ligation. The ligation mixture was transformed into competent E. coli DH5α cells. Plasmid DNA was isolated from ampicillin resistant transformants, and the presence of the correct insert was confirmed by restriction analysis. This plasmid was designated as pSE198.

pSE198 was digested with EcoRI, cloned into pWHM3, which had been digested with EcoRI, and transformed into E. coli DH5α cells. Plasmid DNA was isolated from ampicillin resistant transformants and the presence of the correct insert was confirmed by restriction analysis and DNA sequence analysis. This plasmid DNA was transformed into E. coli DM1, plasmid DNA was isolated from ampicillin resistant transformants, and the presence of the correct insert was confirmed by restriction analysis. This plasmid, which was designated as pSE199, was used to transform protoplasts of S. avermitilis strain SE180-11. Thiostrepton resistant transformants of strain SE180-11 were isolated, the presence of erythromycin resistance was determined, and ThIo^r Erm^r transformants were analyzed by HPLC analysis of fermentation products. The presence of the mutated aveC gene encoding a change at amino acid residue 138 (S138T) was able to restore normal avermectin production to strain SE180-11; however, the B2:B1 ratio was 0.88:1 indicating that this mutation reduces the amount of cyclohexyl-B2 produced relative to cyclohexyl-B1 (TABLE 3). This B2:B1 ratio is even lower than the 0.94:1 ratio observed with the A139T mutation produced by transformation of strain SE180-11 with pSE188, as described above.

Another mutation was constructed to introduce a threonine at both amino acid positions 138 and 139. The ~1.2 Kb insert DNA from pSE186 was used as a PCR template. The PCR primers were designed to introduce mutations at nt positions 585 and 588, and were supplied by Genosys Biotechnologies, Inc. (Texas). The rightward PCR primer was: 5'-GGGGGCGGGCCCGGGTGCGGAGGCG-GAAATGCCGCTGGCGACGACC-3' (SEQ ID NO:14); and the leftward PCR primer was: 5'-GGAACATCACG-GCATTCACC-3' (SEQ ID NO:15). The PCR reaction was performed using the conditions described immediately above in this Section. A PCR product of 449 bp was digested with ApaI and KpnI to release a 254 bp fragment, which was resolved by electrophoresis and purified from the gel. pSE186a was digested with ApaI and KpnI, the DNA fragments separated on an agarose gel, and two fragments of ~3.8 Kb and ~0.4 Kb were purified from the gel. All three fragments (~3.8 Kb, ~0.4 Kb and 254 bp) were ligated together in a 3-way ligation, and the ligation mixture was transformed into competent E. coli DH5α cells. Plasmid DNA was isolated from ampicillin resistant transformants, and the presence of the correct insert was confirmed by restriction analysis. This plasmid was designated as pSE230.

pSE230 was digested with EcoRI, cloned into pWHM3, which had been digested with EcoRI, and transformed into E. coli DH5α cells. Plasmid DNA was isolated from ampicillin resistant transformants and the presence of the correct insert was confirmed by restriction analysis and DNA sequence analysis. This plasmid DNA was transformed into E. coli DM1, plasmid DNA isolated from ampicillin resistant transformants, and the presence of the correct insert was confirmed by restriction analysis. This plasmid, which was designated as pSE231, was used to transform protoplasts of S. avermitilis strain SE180-11. Thiostrepton resistant transformants of SE180-11 were isolated, the presence of erythromycin resistance was determined, and Thio^r Erm^r transformants were analyzed by fermentation. The presence of the double mutated aveC gene, encoding S138T/A139T, was able to restore normal avermectin production to strain SE180-11; however, the B2:B1 ratio was 0.84:1 showing that this mutation further reduces the amount of cyclohexyl-B2 produced relative to cyclohexyl-B1 (TABLE 3), over the reductions provided by transformation of strain SE180-11 with pSE188 or pSE199, as described above.

Another mutation was constructed to further reduce the amount of cyclohexyl-B2 produced relative to cyclohexyl-B1. Because the S138T/A139T mutations altered the B2:B1 ratios in the more favorable B1 direction, a mutation was constructed to introduce a threonine at amino acid position 138 and a phenylalanine at amino acid position 139. The ~1.2 Kb insert DNA from pSE186 was used as a PCR template. The PCR primers were designed to introduce mutations at nt positions 585 (changing a T to A), 588 (changing a G to T), and 589 (changing a C to T), and were supplied by Genosys Biotechnologies, Inc. (Texas). The rightward PCR primer was: 5'-GGGGGCGGGCCCGGGTGCGGAGGCG-GAAATGCCGC TGGCGACGTTC-3' (SEQ ID NO:16); and the leftward PCR primer was: 5'-GGAACATCACG-GCATTCACC-3' (SEQ ID NO:15). The PCR reaction was carried out using an Advantage GC genomic PCR kit (Clonetech Laboratories, Palo Alto, Calif.) in buffer provided by the manufacturer in the presence of 200 µM dNTPs, 200 pmol of each primer, 50 ng template DNA, 1.1 mM Mg acetate, 1.0 M GC-Melt and 1 unit Tth DNA Polymerase in a final volume of 50 µl. The thermal profile of the first cycle was 94° C. for 1 min; followed by 25 cycles of 94° C. for 30 sec and 68° C. for 2 min; and 1 cycle at 68° C. for 3 min. A PCR product of 449 bp was digested with ApaI and KpnI to release a 254 bp fragment, which was resolved by electrophoresis and purified from the gel. All three fragments (~3.8 Kb, ~0.4 Kb and 254 bp) were ligated together in a 3-way ligation. The ligation mixture was transformed into competent E. coli DH5α cells. Plasmid DNA was isolated from ampicillin resistant transformants, and the presence of the correct insert was confirmed by restriction analysis. This plasmid was designated as pSE238.

pSE238 was digested with EcoRI, cloned into pWHM3, which had been digested with EcoRI, and transformed into E. coli DH5α cells. Plasmid DNA was isolated from ampicillin resistant transformants and the presence of the correct insert was confirmed by restriction analysis and DNA sequence analysis. This plasmid DNA was transformed into E. coli DM1, plasmid DNA was isolated from ampicillin resistant transformants, and the presence of the correct insert was confirmed by restriction analysis. This plasmid, which was designated as pSE239, was used to transform protoplasts of S. avermitilis strain SE180-11. Thiostrepton resistant transformants of strain SE180-11 were isolated, the presence of erythromycin resistance was determined, and Thio$^r$ Erm$^r$ transformants were analyzed by HPLC analysis of fermentation products. The presence of the double mutated aveC gene encoding S138T/A139F was able to restore normal avermectin production to strain SE180-11; however, the B2:B1 ratio was 0.75:1 showing that this mutation further reduced the amount of cyclohexyl-B2 produced relative to cyclohexyl-B1 (TABLE 3) over the reductions provided by transformation of strain SE180-11 with pSE188, pSE199, or pSE231 as described above.

TABLE 3

| S. avermitilis strain (transforming plasmid) | No. Transformants Tested | Relative B2 Conc. | Relative B1 Conc. | Avg. B2:B1 Ratio |
| --- | --- | --- | --- | --- |
| SE180-11 (none) | 30 | 0 | 0 | 0 |
| SE180-11 (pWHM3) | 30 | 0 | 0 | 0 |
| SE180-11 (pSE186) | 26 | 222 | 140 | 1.59 |
| SE180-11 (pSE187) | 12 | 283 | 11 | 26.3 |
| SE180-11 (pSE188) | 24 | 193 | 206 | 0.94 |
| SE180-11 (pSE199) | 18 | 155 | 171 | 0.88 |
| SE180-11 (pSE231) | 6 | 259 | 309 | 0.84 |
| SE180-11 (pSE239) | 20 | 184 | 242 | 0.75 |

Additional mutations were constructed to further reduce the amount of cyclohexyl-B2 produced relative to cyclohexyl-B1 using the technique of DNA shuffling as described in Stemmer, 1994, Nature 370:389-391; and Stemmer. 1994, Proc. Natl. Acad. Sci. USA 91:10747-10751; and further described in U.S. Pat. Nos. 5,605,793; 5,811,238; 5,830,721; and 5,837,458.

DNA shuffled plasmids containing mutated aveC genes were transformed into competent dam dcm E. coli cells. Plasmid DNA was isolated from ampicillin resistant transformants, and used to transform protoplasts of S. avermitilis strain SE180-11. Thiostrepton resistant transformants of strain SE180-11 were isolated and screened for the production of avermectins with a cyclohexyl-B2:cyclohexyl-B1 ratio of 1:1 or less. The DNA sequence of plasmid DNA from SE180-11 transformants producing avermectins with a B2:B1 ratio of 1:1 or less was determined.

Eight transformants were identified that produced reduced amounts of cyclohexyl-B2 relative to cyclohexyl-B1. The lowest B2:B1 ratio achieved among these transformants was 040:1 (TABLE 4). Plasmid DNA was isolated from each of the eight transformants and the DNA sequence determined to identify the mutations in the aveC gene. The mutations are as follows.

pSE290 contains 4 nucleotide mutations at nt position 317 from T to A, at nt position 353 from C to A, at nt position 438 from G to A, and at nt position 1155 from T to A. The nucleotide change at nt position 317 changes the amino acid at AA position 48 from D to E and the nucleotide change at nt position 438 changes the amino acid at AA position 89 from A to T. The B2:B1 ratio produced by cells carrying this plasmid was 0.42:1 (TABLE 4).

pSE291 contains 4 nucleotide mutations at nt position 272 from G to A, at nt position 585 from T to A, at nt position 588 from G to A, and at nt position 708 from G to A. The nucleotide change at nt position 585 changes the amino acid at M position 138 from S to T, the nucleotide change at nt position 588 changes the amino acid at M position 139 from A to T, and the nucleotide change at nt position 708 changes the amino acid at AA position 179 from G to S. The B2:B1 ratio produced by cells carrying this plasmid was 0.57:1 (TABLE 4).

pSE292 contains the same four nucleotide mutations as pSE290. The B2:B1 ratio produced by cells carrying this plasmid was 0.40:1 (TABLE 4).

pSE293 contains 6 nucleotide mutations at nt 24 from A to G, at nt position 286 from A to C, at nt position 497 from T to C, at nt position 554 from C to T, at nt position 580 from T to C, and at nt position 886 from A to T. The nucleotide change at nt position 286 changes the amino acid at AA position 38 from Q to P, the nucleotide change at nt position 580 changes the amino acid at AA position 136 from L to P, and the nucleotide change at nt position 886 changes the amino acid at M position 238 from E to D. The B2:B1 ratio produced by cells carrying this plasmid was 0.68:1 (TABLE 4).

pSE294 contains 6 nucleotide mutations at nt 469 from T to C, at nt position 585 from T to A, at nt position 588 from G to A, at nt position 708 from G to A, at nt position 833 from C to T, and at nt position 1184 from G to A. In addition, nts at positions 173, 174, and 175 are deleted. The nucleotide change at nt position 469 changes the amino acid at AA position 99 from F to S, the nucleotide change at nt position 585 changes the amino acid at AA position 138 from S to T, the nucleotide change at nt position 588 changes the amino acid at AA position 139 from A to T, and the nucleotide change at nt position 708 changes the amino acid from AA position 179 from G to S. The B2:B1 ratio produced by cells carrying this plasmid was 0.53:1 (TABLE 4).

pSE295 contains 2 nucleotide mutations at nt 588 from G to A and at nt 856 from T to C. The nucleotide change at nt position 588 changes the amino acid at AA position 139 from A to T and the nucleotide change at nt position 856 changes the amino acid at AA position 228 from M to T. The B2:B1 ratio produced by cells carrying this plasmid was 0.80:1 (TABLE 4).

pSE296 contains 5 nucleotide mutations at nt position 155 from T to C, at nt position 505 from G to T, at nt position 1039 from C to T, at nt position 1202 from C to T, and at nt position 1210 from T to C. The nucleotide change at nt position 505 changes the amino acid at M position 111 from G to V and the nucleotide change at nt position 1039 changes the amino acid at AA position 289 from P to L. The B2:B1 ratio produced by cells carrying this plasmid was 0.73:1 (TABLE 4).

pSE297 contains 4 nucleotide mutations at nt position 377 from G to T, at nt position 588 from G to A, at nt position 633 from A to G, and at nt position 1067 from A to T. The nucleotide change at nt position 588 changes the amino acid at AA position 139 from A to T, the nucleotide change at nt position 633 changes the amino acid at AA position 154 from K to E, and the nucleotide change at nt position 1067 changes the amino acid at AA position 298 from Q to H. The B2:B1 ratio produced by cells carrying this plasmid was 0.67:1 (TABLE 4).

TABLE 4

| S. avermitilis strain (transforming plasmid) | No. Transformants Tested | Relative B2 Conc. | Relative B1 Conc. | Avg. B2:B1 Ratio |
|---|---|---|---|---|
| SE180-11 (none) | 4 | 0 | 0 | 0 |
| SE180-11 (pWHM3) | 4 | 0 | 0 | 0 |
| SE180-11 (pSE290) | 4 | 87 | 208 | 0.42 |
| SE180-11 (pSE291) | 4 | 106 | 185 | 0.57 |
| SE180-11 (pSE292) | 4 | 91 | 231 | 0.40 |
| SE180-11 (pSE293) | 4 | 123 | 180 | 0.68 |
| SE180-11 (pSE294) | 4 | 68 | 129 | 0.53 |
| SE180-11 (pSE295) | 4 | 217 | 271 | 0.80 |
| SE180-11 (pSE296) | 1 | 135 | 186 | 0.73 |
| SE180-11 (pSE297) | 1 | 148 | 221 | 0.67 |

Additional rounds of DNA shuffling were conducted to further reduce the amount of cyclohexyl-B2 avermectin produced relative to cyclohexyl-B1 avermectin as follows.

Semi-Synthetic Shuffling

The best clone was shuffled using the method described in PCT International Publication WO 97/20078 by Maxygen Inc. Individual oligonucleotides encoding beneficial substitutions best corresponding to decreased B2:B1 ratio were added to the shuffling reaction at 5 molar excess over the aveC template strands. Each nucleotide mismatch of the oligonucleotide was flanked by 20 nucleotides of perfect identity to ensure proper incorporation during the shuffling reaction. Oligonucleotides were purchased from Operon Technologies (Alameda, Calif.).

HTP Growth of S. avermitilis

Independent clones were picked from the transformation plates and inoculated into 200 µl R5 medium (Kieser, T., et al., "Practical Streptomyces Genetics", 2000, Norwich, U.K., John Innes Foundation) in deep 96-well seed plates and grown at 30° C. with shaking. In each well, a glass-bead was dispensed for dispersion of mycelia and agitation of the culture. During this time, the cultures attained even and dense growth. After 4-5 days, 20 µl of the seed medium culture was dispensed to production plates and the remaining volume was frozen as master plates at −80° C. after the addition of glycerol to the final concentration of 20%. The production plates were incubated at 30° under humidity for 12-14 days. Sporulation of the strains occurred after 5-8 days of incubation. The production plates were made essentially as described in PCT International Publication WO 99/41389 by Pfizer Inc., with the exception of adding 1% agarose to ensure a solid surface.

Extraction and ESI-MS/MS Screening

A total of 1 ml ethyl acetate was added to each well and incubated shaking at room temperature for 20 minutes. Approximately 750 µl of the ethyl acetate-phase was recovered, transferred to a 96-well plate and set to evaporate over night. The precipitate was resuspended in 100 µl methanol 1 mM NaCl of which 5 µl solution was injected into mass spectrometer by an autosampler in a 96-well format and analyzed directly in the flow injection phase without liquid chromatography or other separation. The compounds were ionized by electrospray ionization and two separate channels were monitored on two MS/MS transitions. The MS/MS transition for B1 sodiated ion is from m/z 921 to m/z 777 and for B2 sodiated ion is from m/z 939 to m/z 795 in positive mode. A Finnigan TSQ-7000, Micromass Quattro-LC mass spectrometer and a Leap Technology Twin-Pal autosampler were used for this high throughput screening. Integration of the separate B1 and B2 chromatograms for each well location identified the hits.

Eighty-eight (88) new combinations of amino acid substitutions were identified that can produce ratios of cyclohexyl B2:cyclohexyl B1 avermectins of 0.35:1 or less (FIG. 6). Several of these new mutations can produce ratios of cyclohexyl B2:cyclohexyl B1 avermectins of about 0.30:1 or less; several can produce ratios of cyclohexyl B2:cyclohexyl B1 avermectins of about 0.25:1 or less, and several can produce ratios of cyclohexyl B2:cyclohexyl B1 avermectins of about 0.20:1 or less, and several can produce ratios of cyclohexyl B2:cyclohexyl B1 of about 0.1:1 or less. Two (2) new mutations were identified that can produce ratios of cyclohexyl B2:cyclohexyl B1 avermectins of 0.37 or 0.38. Eighteen (18) new mutations were identified that can produce ratios of cyclohexyl B2:cyclohexyl B1 between 0.58:1 and 1.17:1.

Deposit of Biological Materials

The following plasmids were deposited with the American Type Culture Collection (ATCC) at 12301 Parklawn Drive, Rockville, Md., 20852, USA, on Jan. 29, 1998, and were assigned the following accession numbers:

| Plasmid | Accession No. |
|---|---|
| plasmid pSE180 | 209605 |
| plasmid pSE186 | 209604 |

The current address of the American Type Culture Collection is 10801 University Blvd, Manassas, Va., 20110, USA.

All patents, patent applications, and publications cited above are incorporated herein by reference in their entirety.

The present invention is not to be limited in scope by the specific embodiment described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

The invention claimed is:

1. An isolated *Streptomyces avermitilis* cell which produce a cyclohexyl B2:cyclohexyl B1 avermectin ratio of about 0.35:1 or less, comprising a nucleotide sequence that is otherwise the same as the *S. avermitilis* aveC allele, the *S. avermitilis* AveC gene product-encoding sequence of plasmid pSE 186 (ATCC 209604) or the nucleotide sequence of the aveC ORF of *S.avermitilis* of SEQ ID NO:1, or a degenerate variant thereof, which nucleotide encodes a functionally equivalent aveC gene product and which nucleotide sequence further comprises mutations encoding one or more amino acid substitutions in the amino acid sequence of SEQ. ID. NO:2 wherein said amino acid substitution is selected from the group consisting of:

(a) D48E, A61T, A89T, S138T, A139T, G179S, A198G, P289L;
(b) G40S, D48E, L136P, G179S, E238D;
(c) D48E, L136P, R163Q, G179S;
(d) D48E, L136P, R163Q, G179S, E238D;
(e) D48E, L136P, R163Q, G179S, A200G, E238D;
(f) D48E, L136P, G179S, E238D;
(g) D48E, A61T, L136P, G179S, E238D;
(h) D48E, A61T, L136P, G179S;
(j) D48E, A61T, L136P, G179S, A198G, P202S, E238D, P289L;
(k) D48E, A61T, L136P, S138T, A139F, G179S, E238D, P289L;
(l) D48E, L136P, G179S, A198G, E238D, P289L;
(m) D48E, A61T, S138T, A139F, G179S, A198G, P289L;
(n) D48E, L84P, G111V, S138T, A139T, G179S, A198G, P289L;
(o) Y28C, D48E, A61T, A89T, S138T, A139T, G179S, E238D;
(p) D48E, A61T, A107T, S108G, L136P, G179S, S192A, E238D, P289L;
(q) D48E, L136P, G179S, R250W;
(r) D48E, A89T, S138T, A139T, R163Q, G179S;
(s) D48E, L136P, G179S, A198G, P289L;
(t) D48E, F78L, A89T, L136P, G179S;
(u) D48E, A89T, S138T, A139T, G179S, E238D, F278L;
(v) D48E, A89T, L136P, R163Q, G179S;
(w) D48E, A61T, A89T, G111V, S138T, A139F, G179S, E238D, P289L;
(x) D25G, D48E, A89T, L136P, S138T, A139T, V141A, I159T, R163Q, G 179S;
(y) D48E, A89T, S90G, L136P, R163Q, G179S, E238D;
(z) D48E, A61T, A89T, G111V, S138T, A139T, G179S, E238D, P289L;
(ab) D48E, L136P, R163Q, G179S, S231L;
(ac) D48E, L136P, S138T, A139F, G179S, V196A, E238D;
(ad) D48E, A61T, A89T, F99S, S138T, A139T, G179S, E238D;
(ae) G35S, D48E, A89T, S138T, A139T, G179S, P289L;
(af) D48E, A61T, A89T, S138T, A139T, G179S, V196A, E238D;
(ag) D48E, A89T, G111V, S138T, A139T, G179S, A198G, E238D;
(ah) S41G, D48E, A89T, L136P, G179S;
(ai) D48E, A89T, L136P, R163Q, G179S, P252S;
(aj) D48E, A89T, L136P, G179S, F234S;
(ak) D48E, A89T, L136P, R163Q, G179S, E238D;
(al) Q36R, D48E, A89T, L136P, G179S, E238D;
(am) D48E, A89T, L136P, R163Q, G179S;
(an) D48E, A89T, S138T, G179S;
(ao) D48E, A89T, L136P, G179S, E238D;
(ap) D48E, A89T, L136P, K154E, G179S, E238D;
(aq) D48E, A89T, S138T, A139T, K154R, G179S, V196A, P289L;
(ar) D48E, A89T, S138T, A139F, G179S, V196A, E238D;
(as) D48E, A61T, A89T, L136P, G179S, V196A, A198G, P289L;
(at) D48E, A61T, S138T, A139F, G179S, V196A, E238D, P289L;
(au) D48E, A89T, L136P, G179S;
(av) D48E, A89T, V120A, L136P, G179S;
(aw) D48E, A61T, A89T, S138T, A139F, G179S, V196A, A198G, E238D;
(ax) D48E, A61T, A89T, G111V, S138T, A139F, G179S, V196A, E238D;
(ay) D48E, A61T, A89T, S138T, A139T, G179S, V196A, E238D, P289L;
(az) D48E, A61T, A89T, L136P, S138T, A139F, G179S, A198G, E238D;
(ba) D48E, A89T, S138T, A139F, G179S, A198G, V220A;
(bb) D48E, A61T, A89T, S138T, A139T, G179S, V196A, E238D, R239H, P289L;
(bc) D48E, A61T, A89T, L136P, G179S, P289L;
(bd) D48E, A89T, S138T, A139T, G179S, V196A, E238D, P289L;
(be) D48E, A61T, A89T, S138T, A139F, G179S, V196A, E238D;
(da) S41G, D48E, A61T, R71L, A89T, L136M, S138T, A139T, T149S, G179S, V196A, E238D, F278L, P289L;
(db) S41G, D48E, A61T, R71L, A89T, L136M, S138T, A139T, T149S, F176C, G179S, V196A, E238D, P289L;
(de) D48E, R71L, A89T, L136P, T149S, F176C, G179S, E238D, I280V;
(dd) D48E, A61T, R71L, W110L, T149S, G179S, V196A, L206M, E238D, V271A, I280V;
(de) D48E, A61T, R71L, A89T, L136M, S138T, A139T, T149S, G179S, V196A, E238D, H279Q, P289L;
(df) D48E, A61T, R71L, A89T, L136M, S138T, A139T, T149S, G179S, V196A, E238D, G287E, P289Q;
(dg) D48E, A61T, R71L, A89T, L136M, S138T, A139T, T149S, G179S, V196A, E238D, P289L;
(dh) D48E, A61T, R71L, A89T, A139T, T149S, F176C, G179S, V196A, E238D, V285G, P289L;
(di) Q38R, D48E, A61T, R71L, L87V, A89T, L136M, S138T, A139T, T149S, G179S, V196A, E238D, P289L;
(dj) D48E, A61T, L87V, A89T, W110L, S138T, A139T, T149S, G179S, V196A, E238D, P289L;

(dk) D48E, A61T, R71L, A89T, L136M, S138T, A139T, T149S, G179S, V196A, E238D, P289L;
(dl) D48E, A89T, L136P, K154E, G179S, S231L, E238D;
(ea) D48E, A61T, R71L, A89T, L136P, T149S, F176C, G179S, V196A, E238D, I280V;
(eb) D48E, R71L, A89T, L136P, T149S, F176C, G179S, E238D, I280V;
(ec) Q36P, D48E, A61T, R71L, A89T, L136P, T149S, F176C, G179S, V196A, E238D, I280V;
(ed) D48E, A61T, R71L, A89T, A139T, T149S, F176C, G179S, V196A, E238D, I280V;
(ee) V2M, D48E, A61T, R71L, A89T, L136P, T149S, F176C, G179S, V196A, E238D, I280V;
(ef) D48E, A61T, R71L, A89T, L136P, T149S, F176C, G179S, V196A, E238D, I280V, A302T;
(eg) D48E, R71L, A89T, L136P, T149S, F176C, G179S, E238D, P289L;
(eh) D48E, R71L, A89T, L136P, T149S, F176C, G179S, E238D, A302T;
(ei) D48E, R71L, A89T, L136P, T149S, F176C, G179S, V196A, E238D, I280V;
(ej) D48E, A61T, R71L, A89T, L136P, T149S, F176C, G179S, V196A, E238D;
(ek) V2M, D48E, A61T, R71L, A89T, L136P, T149S, F176C, G179S, V196A, E238D, I280V;
(el) D48E, A61T, R71L, A89T, L136P, T149S, R162H, F176C, G179S, V196A, E238D, I280V;
(em) D48E, R71L, A89T, V120A, L136P, T149S, K154E, G179S, S231L, E238D;
(en) D48E, R71L, A89T, V120A, L136P, T149S, F176C, G179S, S231L, E238D, I280V;
(eo) D48E, A61T, R71L, L87V, A89T, S90N, A139T, T149S, F176C, G179S, V196A, E238D, V285G, P289L;
(ep) D48E, A61T, R71L, L87V, A89T, A139T, T149S, F176C, G179S, V196A, E238D, V285G, P289L;
(eq) D48E, R71L, A89T, L136P, K154E, G179S, S231L, E238D;
(er) D48E, R71L, A89T, V120A, L136P, K154E, F176C, G179S, S231L, E238D; and
(es) D48E, R71L, A89T, V120A, L136P, T149S, K154E, F176C, G179S, S231L, E238D.

2. The isolated *S.avermitilis* cell of claim 1 wherein said amino acid substitution is selected from the group consisting of:
(g) D48E, A61T, L136P, G179S, E238D;
(h) D48E, A61T, L136P, G179S;
(j) D48E, A61T, L136P, G179S, A198G, P202S, E238D, P289L;
(k) D48E, A61T, L136P, S138T, A139F, G179S, E238D, P289L;
(l) D48E, L136P, G179S, A198G, E238D, P289L;
(m) D48E, A61T, S138T, A139F, G179S, A198G, P289L;
(n) D48E, L84P, G111V, S138T, A139T, G179S, A198G, P289L;
(o) Y28C, D48E, A61T, A89T, S138T, A139T, G179S, E238D;
(p) D48E, A61T, A107T, S108G, L136P, G179S, S192A, E238D, P289L;
(q) D48E, L136P, G179S, R250W;
(r) D48E, A89T, S138T, A139T, R163D, G179S;
(s) D48E, L136P, G179S, A198G, P289L;
(t) D48E, F78L, A89T, L136P, G179S;
(u) D48E, A89T, S138T, A139T, G179S, E238D, F278L;
(v) D48E, A89T, L136P, R163Q, G179S;
(w) D48E, A89T, G111V, S138T, A139F, G179S, E238D, P289L;
(x) D25G, D48E, A89T, L136P, S138T, A139T, V141A, I159T, R163Q, G179S;
(y) D48E, A89T, 590G, L136P, R163D, G179S, E238D;
(z) D48E, A61T, A89T, G111V, S138T, A139T, G179S, E238D, P289L;
(ab) D48E, L136P, R163Q, G179S, S231L;
(ac) D48E, L136P, S138T, A139F, G179S, V196A, E238D;
(ad) D48E, A61T, A89T, F99S, S138T, A139T, G179S, E238D;
(ae) G35S, D48E, A89T, S138T, A139T, G179S, P289L;
(af) D48E, A61T, A89T, S138T, A139T, G179S, V196A, E238D;
(ag) D48E, A89T, G111V, S138T, A139T, G179S, A198G, E238D;
(ah) S41G, D48E, A89T, L136P, G179S;
(ai) D48E, A89T, L136P, R163Q, G179S, P252S;
(aj) D48E, A89T, L136P, G179S, F234S;
(ak) D48E, A89T, L136P, R163Q, G179S, E238D;
(al) Q36R, D48E, A89T, L136P, G179S, E238D;
(am) D48E, A89T, L136P, R163Q, G179S;
(an) D48E, A89T, S138T, G179S;
(ao) D48E, A89T, L136P, G179S, E238D;
(ap) D48E, A89T, L136P, K154E, G179S, E238D;
(aq) D48E, A89T, S138T, A139T, K154R, G179S, V196A, P289L;
(ar) D48E, A89T, S138T, A139F, G179S, V196A, E238D;
(as) D48E, A61T, A89T, L136P, G179S, V196A, A198G, P289L;
(at) D48E, A61T, S138T, A139F, G179S, V196A, E238D, P289L;
(au) D48E, A89T, L136P, G179S;
(av) D48E, A89T, V120A, L136P, G179S;
(aw) D48E, A61T, A89T, S138T, A139F, G179S, V196A, A198G, E238D;
(ax) D48E, A61T, A89T, G111V, S138T, A139F, G179S, V196A, E238D;
(ay) D48E, A61T, A89T, S138T, A139T, G179S, V196A, E238D, P289L;
(az) D48E, A61T, A89T, L136P, S138T, A139F, G179S, A198G, E238D;
(ba) D48E, A89T, S138T, A139F, G179S, A198G, V220A;
(bb) D48E, A61T, A89T, S138T, A139T, G179S, V196A, E238D, R239H, P289L;
(bc) D48E, A61T, A89T, L136P, G179S, P289L;
(bd) D48E, A89T, S138T, A139T, G179S, V196A, E238D, P289L;
(be) D48E, A61T, A89T, S138T, A139F, G179S, V196A, E238D;
(da) S41G, D48E, A61T, R71L, A89T, L136M, S138T, A139T, T149S, G179S, V196A, E238D, F278L, P289L;
(db) S41G, D48E, A61T, R71L, A89T, L136M, S138T, A139T, T149S, F176C, G179S, V196A, E238D, P289L;
(dc) D48E, R71L, A89T, L136P, T149S, F176C, 0179S, E238D, I280V;
(dd) D48E, A61T, R71L, W110L, T149S, G179S, V196A, L206M, E238D, V271A, I280V;
(de) D48E, A61T, R71L, A89T, L136M, S138T, A139T, T149S, G179S, V196A, E238D, H279Q, P289L;
(df) D48E, A61T, R71L, A89T, L136M, S138T, A139T, T149S, G179S, V196A, E238D, G287E, P289Q;
(dg) D48E, A61T, R71L, A89T, L136M, S138T, A139T, T149S, G179S, V196A, E238D, P289L;
(dh) D48E, A61T, R71L, A89T, A139T, T149S, F176C, G179S, V196A, E238D, V285G, P289L;
(di) Q38R, D48E, A61T, R71L, L87V, A89T, L136M, S138T, A139T, T149S, G179S, V196A, E238D, P289L;

(dj) D48E, A61T, L87V, A89T, W110L, S138T, A139T, T149S, G179S, V196A, E238D, P289L;
(dk) D48E, A61T, R71L, A89T, L136M, S138T, A139T, T149S, G179S, V196A, E238D, P289L;
(dl) D48E, A89T, L136P, K154E, G179S, S231L, E238D;
(ea) D48E, A61T, R71L, A89T, L136P, T149S, F176C, G179S, V196A, E238D, I280V;
(eb) D48E, R71L, A89T, L136P, T149S, F176C, G179S, E238D, I280V;
(ec) Q36P, D48E, A61T, R71L, A89T, L136P, T149S, F176C, G179S, V196A, E238D, I280V;
(ed) D48E, A61T, R71L, A89T, A139T, T149S, F176C, G179S, V196A, E238D, I280V;
(ee) V2M, D48E, A61T, R71L, A89T, L136P, T149S, F176C, G179S, V196A, E238D, I280V;
(ef) D48E, A61T, R71L, A89T, L136P, T149S, F176C, G179S, V196A, E238D, I280V, A302T;
(eg) D48E, R71L, A89T, L136P, T149S, F176C, G179S, E238D, P289T;
(eh) D48E, R71L, A89T, L136P, T149S, F176C, G179S, E238D, A302T;
(ei) D48E, R71L, A89T, L136P, T149S, F176C, G179S, V196A, E238D, I280V;
(ej) D48E, A61T, R71L, A89T, L136P, T149S, F176C, G179S, V196A, E238D;
(ek) V2M, D48E, R71L, A89T, L136P, T149S, F176C, G179S, V196A, E238D, I280V;
(el) D48E, A61T, R71L, A89T, L136P, T149S, R162H, F176C, G179S, V196A, E238D, I280V;
(em) D48E, R71L, A89T, V120A, L136P, T149S, K154E, G179S, S231L, E238D;
(en) D48E, R71L, A89T, V120A, L136P, T149S, F176C, G179S, S231L, E238D, I280V;
(eo) D48E, A61T, L87V, A89T, S90N, A139T, T149S, F176C, G179S, V196A, E238D, V285G, P289L;
(ep) D48E, A61T, R71L, L87V, A89T, A139T, T149S, F176C, G179S, V196A, E238D, V285G, P289L;
(eq) D48E, R71L, A89T, L136P, K154E, G179S, S231L, E238D;
(er) D48E, A89T, V120A, L136P, K154E, F176C, G179S, S231L, E238D; and
(es) D48E, R71L, A89T, V120A, L136P, K154E, F176C, G179S, S231L, E238D.

3. The isolated S.avermitilis cell of claim 1 wherein said amino acid substitution is selected from the group consisting of:
(w) D48E, A61T, A89T, G111V, S138T, A139F, G179S, E238D, P289L;
(x) D25G, D48E, A89T, L136P, S138T, A139T, V141A, I159T, R163Q, G179S;
(y) D48E, A89T, S90G, L136P, R163Q, G179S, E238D;
(z) D48E, A61T, A89T, G111V, S138T, A139T, G179S, E238D, P289L;
(ab) D48E, L136P, R163Q, G179S, S231L,
(ac) D48E, L136P, S138T, A139F, G179S, V196A, E238D;
(ad) D48E, A61T, A89T, F99S, S138T, A139T, G179S, E238D;
(ae) G35S, D48E, A89T, S138T, A139T, G179S, P289L;
(af) D48E, A61T, A89T, S138T, A139T, G179S, V196A, E238D;
(ag) D48E, A89T, G111V, S138T, A139T, G179S, A198G, E238D;
(ah) S41G, D48E, A89T, L136P, G179S;
(ai) D48E, A89T, L136P, R163Q, G179S, P252S;
(aj) D48E, A89T, L136P, G179S, F234S;
(ak) D48E, A89T, L136P, R163Q, G179S, E238D;
(al) Q36R, D48E, A89T, L136P, G179S, E238D;
(am) D48E, A89T, L136P, R163Q, G179S;
(an) D48E, A89T, S138T, G179S;
(ao) D48E, A89T, L136P, G179S, E238D;
(ap) D48E, A89T, L136P, K154E, G179S, E238D;
(aq) D48E, A89T, S138T, A139T, K154R, G179S, V196A, P289L;
(ar) D48E, A89T, S138T, A139F, G179S, V196A, E238D;
(as) D48E, A61T, A89T, L136P, G179S, V196A, A198G, P289L;
(at) D48E, A61T, S138T, A139F, G179S, V196A, E238D, P289L;
(au) D48E. A89T, L136P, G179S;
(av) D48E, A89T, V120A, L136P, G179S;
(aw) D48E, A61T, A89T, S138T, A139F, G179S, V196A, A198G, E238D;
(ax) D48E, A61T, A89T, G111V, S138T, A139F, G179S, V196A, E238D;
(ay) D48E, A61T, A89T, S138T, A139T, G179S, V196A, E238D, P289L;
(az) D48E, A61T, A89T, L136P, S138T, A139F, G179S, A198G, E238D;
(ba) D48E, A89T, S138T, A139F, G179S, A198G, V220A;
(bb) D48E, A61T, A89T, S138T, A139T, G179S, V196A, E238D, R239H, P289L;
(bc) D48E, A61T, A89T, L136P, G179S, P289L;
(bd) D48E, A89T, S138T, A139T, G179S, V196A, E238D, P289L;
(be) D48E, A61T, A89T, S138T, A139F, G179S, V196A, E238D;
(da) S41G, D48E, A61T, R71L, A89T, L136M, S138T, A139T, T149S, G179S, V196A, E238D, F278L, P289L;
(db) S41G, D48E, A61T, R71L, A89T, L136M, S138T, A139T, T149S, F176C, G179S, V196A, E238D, P289L;
(dc) D48E, R71L, A89T, L136P, T149S, F176C, G179S, E238D, I280V;
(dd) D48E, A61T, R71L, W110L, T149S, G179S, V196A, L206M, E238D, V271A, I280V;
(de) D48E, A61T, R71L, A89T, L136M, S138T, A139T, T149S, G179S, V196A, E238D, H279Q, P289L;
(df) D48E, A61T, R71L, A89T, L136M, S138T, A139T, T149S, G179S, V196A, E238D, G287E, P289Q;
(dg) D48E, A61T, R71L, A89T, L136M, S138T, A139T, T149S, G179S, V196A, E238D, P289L;
(dh) D48E, A61T, R71L, A89T, A139T, T149S, F176C, G179S, V196A, E238D, V285G, P289L;
(di) Q38R, D48E, A61T, R71L, L87V, A89T, L136M, S138T, A139T, T149S, G179S, V196A, E238D, P289L;
(dj) D48E, A61T, L87V, A89T, W110L, S138T, A139T, T149S, G179S, V196A, E238D, P289L;
(dk) D48E, A61T, R71L, A89T, L136M, S138T, A139T, T149S, G179S, V196A, E238D, P289L;
(dl) D48E, A89T, L136P, K154E, G179S, S231L, E238D;
(ea) D48E, A61T, R71L, A89T, L136P, T149S, F176C, G179S, V196A, E238D, I280V;
(eb) D48E, R71L, A89T, L136P, T149S, F176C, G179S, E238D, I280V;
(ec) Q36P, D48E, A61T, R71L, A89T, L136P, T149S, F176C, G179S, V196A, E238D, I280V;
(ed) D48E, A61T, R71L, A89T, A139T, T149S, F176C, G179S, V196A, E238D, I280V;
(ee) V2M, D48E, A61T, R71L, A89T, L136P, T149S, F176C, G179S, V196A, E238D, I280V;
(ef) D48E, A61T, R71L, A89T, L136P, T149S, F176C, G179S, V196A, E238D, I280V, A302T;

(eg) D48E, R71L, A89T, L136P, T149S, F176C, G179S, E238D, P289L;
(eh) D48E, R71L, A89T, L136P, T149S, F176C, G179S, E238D, A302T;
(ei) D48E, R71L, A89T, L136P, T149S, F176C, G179S, V196A, E238D, I280V;
(ej) D48E, A61T, R71L, A89T, L136P, T149S, F176C, G179S, V196A, E238D;
(ek) V2M, D48E, R71L, A89T, L136P, T149S, F176C, G179S, V196A, E238D, I280V;
(el) D48E, A61T, R71L, A89T, L136P, T149S, R162H, F176C, G179S, V196A, E238D, I280V;
(em) D48E, R71L, A89T, V120A, L136P, T149S, K154E, G179S, S231L, E238D;
(en) D48E, R71L, A89T, V120A, L136P, T149S, F176C, G179S, S231L, E238D, I280V;
(eo) D48E, A61T, R71L, L87V, A89T, S90N, A139T, T149S, F176C, G179S, V196A, E238D, V285G, P289L;
(ep) D48E, A61T, R71L, L87V, A89T, A139T, T149S, F176C, G179S, V196A, E238D, V285G, P289L;
(eq) D48E, R71L, A89T, L136P, K154E, G179S, S231L, E238D;
(er) D48E, R71L, A89T, V120A, L136P, K154E, F176C, G179S, S231L, E238D; and
(es) D48E, R71L, A89T, V120A, L136P, T149S, K154E, F176C, G179S, S231L, E238D.

4. The isolated *S.avermitilis* cell of claim 1 wherein said amino acid substitution is selected from the group consisting of:
(as) D48E, A61T, A89T, L136P, G179S, V196A, A198G, P289L;
(at) D48E, A61T, S138T, A139F, G179S, V196A, E238D, P289L;
(au) D48E, A89T, L136P, G179S;
(av) D48E, A89T, V120A, L136P, G179S;
(aw) D48E, A61T, A89T, S138T, A139F, G179S, V196A, A198G, E238D;
(ax) D48E, A61T, A89T, G111V, S138T, A139F, G179S, V196A, E238D;
(ay) D48E, A61T, A89T, S138T, A139T, G179S, V196A, E238D, P289L;
(az) D48E, A61T, A89T, L136P, S138T, A139F, G179S, A198G, E238D;
(ba) D48E, A89T, S138T, A139F, G179S, A198G, V220A;
(bb) D48E, AGIT, A89T, S138T, A139T, G179S, V196A, E238D, R239H, P289L;
(bc) D48E, A61T, A89T, L136P, G179S, P289L;
(bd) D48E, A89T, S138T, A139T, G179S, V196A, E238D, P289L;
(be) D48E, A61T, A89T, S138T, A139F, G179S, V196A, E238D;
(da) S41G, D48E, A61T, R71L, A89T, L136M, S138T, A139T, T149S, G179S, V196A, E238D, F278L, P289L;
(db) S41G, D48E, A61T, R71L, A89T, L136M, S138T, A139T, T149S, F176C, G179S, V196A, E238D, P289L;
(dc) D48E, R71L, A89T, L136P, T149S, F176C, G179S, E238D,
(dd) D48E, A61T, R71L, W110L, T149S, G179S, V196A, L206M, E238D, V271A, I280V;
(de) D48E, A61T, R71L, A89T, L136M, S138T, A139T, T149S, G179S, V196A, E238D, H279Q, P289L;
(df) D48E, A61T, R71L, A89T, L136M, S138T, A139T, T149S, G179S, V196A, E238D, G287E, P289Q;
(dg) D48E, A61T, R71L, A89T, L136M, S138T, A139T, T149S, G179S, V196A, E238D, P289L;
(dh) D48E, A61T, R71L, A89T, A139T, T149S, F176C, G179S, V196A, E238D, V285G, P289L;
(di) Q38R, D48E, A61T, R71L, L87V, A89T, L136M, S138T, A139T, T149S, G179S, V196A, E238D, P289L;
(dj) D48E, A61T, L87V, A89T, W110L, S138T, A139T, T149S, G179S, V196A, E238D, P289L;
(dk) D48E, A61T, R71L, A89T, L136M, S138T, A139T, T149S, G179S, V196A, E238D, P289L;
(dl) D48E, A89T, L136P, K154E, G179S, S231L, E238D;
(ea) D48E, A61T, R71L, A89T, L136P, T149S, F176C, G179S, V196A, E238D, I280V;
(eb) D48E, R71L, A89T, L136P, T149S, F176C, G179S, E238D, I280V;
(ec) Q36P, D48E, A61T, R71L, A89T, L136P, T149S, F176C, G179S, V196A, E238D, I280V;
(ed) D48E, A61T, R71L, A89T, A139T, T149S, F176C, G179S, V196A, E238D, I280V;
(ee) V2M, D48E, A61T, R71L, A89T, L136P, T149S, F176C, G179S, V196A, E238D, I280V;
(ef) D48E, A61T, R71L, A89T, L136P, T149S, F176C, G179S, V196A, E238D, I280V, A302T;
(eg) D48E, R71L, A89T, L136P, T149S, F176C, G179S, E238D, P289L;
(eh) D48E, R71L, A89T, L136P, T149S, F176C, G179S, E238D, A302T;
(ei) D48E, R71L, A89T, L136P, T149S, F176C, G179S, V196A, E238D, I280V;
(ej) D48E, A61T, R71L, A89T, L136P, T149S, F176C, G179S, V196A, E238D;
(ek) V2M, D48E, R71L, A89T, L136P, T149S, F176C, G179S, V196A, E238D, I280V;
(el) D48E, A61T, R71L, A89T, L136P, T149S, R162H, F176C, G179S, V196A, E238D, I280V;
(em) D48E, R71L, A89T, V120A, L136P, T149S, K154E, G179S, S231L, E238D;
(en) D48E, R71L, A89T, V120A, L136P, T149S, F176C, G179S, S231L, E238D, I280V;
(ed) D48E, AGIT, R71L, L87V, A89T, S90N, A139T, T149S, F176C, G179S, V196A, E238D, V285G, P289L;
(ep) D48E, A61T, R71L, L87V, A89T, A139T, T149S, F176C, G179S, V196A, E238D, V285G, P289L;
(eq) D48E, R71L, A89T, L136P, K154E, G179S, S231L, E238D;
(er) D48E, R71L, A89T, V120A, L136P, K154E, F176C, G179S, S231L, E238D; and
(es) D48E, R71L, A89T, V120A, L136P, T149S, K154E, F176C, G179S, S231L, E238D.

5. The isolated *S.avermitilis* cell of claim 1 wherein said amino acid substitution is selected from the group consisting of:
(ea) D48E, A61T, R71L, A89T, L136P, T149S, F176C, G179S, V196A, E238D, I280V;
(eb) D48E, R71L, A89T, L136P, T149S, F176C, G179S, E238D, I280V;
(ec) Q36P, D48E, A61T, R71L, A89T, L136P, T149S, F176C, G179S, V196A, E238D, I280V;
(ed) D48E, A61T, R71L, A89T, A139T, T149S, F176C, G179S, V196A, E238D, I280V;
(ee) V2M, D48E, A61T, R71L, A89T, L136P, T149S, F176C, G179S, V196A, E238D, I280V;
(ef) D48E, A61T, R71L, A89T, L136P, T149S, F176C, G179S, V196A, E238D, I280V, A302T;
(eg) D48E, R71L, A89T, L136P, T149S, F176C, G179S, E238D, P289L;
(eh) D48E, R71L, A89T, L136P, T149S, F176C, G179S, E238D, A302T;

(ei) D48E, R71L, A89T, L136P, T149S, F176C, G179S, V196A, E238D, I280V;
(ej) D48E, A61T, R71L, A89T, L136P, T149S, F176C, G179S, V196A, E238D;
(ek) V2M, D48E, R71L, A89T, L136P, T149S, F176C, G179S, V196A, E238D, I280V;
(el) D48E, A61T, R71L, A89T, L136P, T149S, R162H, F176C, G179S, V196A, E238D, I280V;
(em) D48E, R71L, A89T, V120A, L136P, T149S, K154E, G179S, S231L, E238D;
(en) D48E, R71L, A89T, V120A, L136P, T149S, F176C, G179S, S231L, E238D, I280V;
(eo) D48E, A61T, R71L, L87V, A89T, S90N, A139T, T149S, F176C, G179S, V196A, E238D, V285G, P289L;
(ep) D48E, A61T, R71L, L87V, A89T, A139T, T149S, F176C, G179S, V196A, E238D, V285G, P289L;
(eq) D48E, R71L, A89T, L136P, K154E, G179S, S231L, E238D;
(er) D48E, R71L, A89T, V120A, L136P, K154E, F176C, G179S, S231L, E238D; and
(es) D48E, R71L, A89T V120A, L136P, T149S, K154E, F176C, G179S, S231L, E238D.

\* \* \* \* \*

UNITED STATES PATENT AND TRADEMARK OFFICE
CERTIFICATE OF CORRECTION

PATENT NO. : 8,008,078 B2
APPLICATION NO. : 12/107949
DATED : August 30, 2011
INVENTOR(S) : Stutzman-Engwall et al.

It is certified that error appears in the above-identified patent and that said Letters Patent is hereby corrected as shown below:

Column 63, line 17, at the beginning of the line, "mititis" should read --mitilis--.

Column 64, line 16, at the end of the line, "F2345" should read --F234S--.

Column 65, line 61, "R163D" should read --R163Q--.

Column 66, line 3, "590G" should read --S90G-- and "R163D" should read --R163Q--; line 54, "0179S" should read --G179S--.

Column 68, line 28, beginning of the line, "(be)" should read --(bc)--; line 37, beginning of the line, "(de)" should read --(dc)--; line 51, beginning of the line, "(di)" should read --(dj)--.

Column 69, line 47, "AG1T" should read --AG1T--; line 59, --I280V;-- missing from end of line.

Column 70, line 5, beginning of the line, "(di)" should read --(dj)--; line 26, beginning of the line, "(el)" should read --(ei)--; line 38, beginning of the line, "(ed)" should read --(eo)--.

Column 72, line 10, --,-- should be inserted between "A89T V120A".

Signed and Sealed this
Eighth Day of November, 2011

David J. Kappos
*Director of the United States Patent and Trademark Office*